(12) United States Patent
Kumar-Singh et al.

(10) Patent No.: US 8,778,886 B2
(45) Date of Patent: Jul. 15, 2014

(54) METHODS OF MAKING AND USING A CELL PENETRATING PEPTIDE FOR ENHANCED DELIVERY OF NUCLEIC ACIDS, PROTEINS, DRUGS, AND ADENOVIRUS TO TISSUES AND CELLS, AND COMPOSITIONS AND KITS

(75) Inventors: Rajendra Kumar-Singh, Boston, MA (US); Siobhan M. Cashman, Boston, MA (US); Sarah Parker Read, Cambridge, MA (US)

(73) Assignee: Tufts University, Boston, MA (US)

( * ) Notice: Subject to any disclaimer, the term of this patent is extended or adjusted under 35 U.S.C. 154(b) by 177 days.

(21) Appl. No.: 12/714,106

(22) Filed: Feb. 26, 2010

(65) Prior Publication Data

US 2010/0209447 A1 Aug. 19, 2010

Related U.S. Application Data

(63) Continuation-in-part of application No. PCT/US2008/010179, filed on Aug. 28, 2008.

(60) Provisional application No. 60/966,591, filed on Aug. 29, 2007.

(51) Int. Cl.
| | | |
|---|---|---|
| A61K 38/00 | (2006.01) | |
| A61K 47/00 | (2006.01) | |
| A61K 38/16 | (2006.01) | |
| A61K 38/10 | (2006.01) | |
| A61K 38/08 | (2006.01) | |
| A61K 39/385 | (2006.01) | |
| A61K 38/04 | (2006.01) | |
| A61M 31/00 | (2006.01) | |
| A61P 9/10 | (2006.01) | |
| A61P 27/02 | (2006.01) | |
| C07K 5/00 | (2006.01) | |
| C07K 7/00 | (2006.01) | |
| C07K 16/00 | (2006.01) | |
| C07K 17/00 | (2006.01) | |

(52) U.S. Cl.
USPC .............. 514/20.8; 424/193.1; 424/195.11; 514/1.2; 514/21.3; 514/21.4; 514/21.6; 514/56; 530/324; 530/326; 530/327; 604/521

(58) Field of Classification Search
None
See application file for complete search history.

(56) References Cited

U.S. PATENT DOCUMENTS

| | | | |
|---|---|---|---|
| 2004/0176282 A1* | 9/2004 | Dalby et al. | 514/8 |
| 2005/0042603 A1* | 2/2005 | Wang | 435/5 |
| 2005/0175703 A1* | 8/2005 | Hunter et al. | 424/486 |
| 2006/0172931 A1 | 8/2006 | San Antonio et al. | |
| 2007/0105775 A1 | 5/2007 | Lee et al. | |
| 2009/0011040 A1* | 1/2009 | Naash et al. | 424/501 |

FOREIGN PATENT DOCUMENTS

| | | | | |
|---|---|---|---|---|
| WO | WO 9967284 A2 * | 12/1999 | | C07K 14/16 |
| WO | WO02060488 A1 * | 8/2002 | | A61K 47/48 |
| WO | WO 02067917 A1 * | 9/2002 | | A61K 31/155 |
| WO | WO03/106491 A2 | 12/2003 | | |
| WO | WO 2005014619 A2 * | 2/2005 | | |
| WO | WO2007/095152 A2 | 8/2007 | | |

OTHER PUBLICATIONS

Kilic et al., "The TAT Protein Transduction Domain Enhances the Neuroprotective Effect of Glial-Cell-Line-Derived Neurotrophic Factor after Optic Nerve Transduction," Neurodeg. Dis. 1:44-49 (2004).*
Verrecchio et al., "Design of Peptides with High Affinities for Heparin and Endotheial Cell Proteoglycans," J. Biol. Chem. 17:7701-7707 (2000).*
Read et al. "POD Nanoparticles Expressing GDNF Provide Structural and Functional Rescue of Light-induced Retinal Degeneration in an Adult Mouse" Mol Ther, 2010, vol. 18, pp. 1917-1926.
Schorderet et al. "D-TAT transporter as an ocular peptide delivery system" Clin Exp Opthalmol, 2005, vol. 33, pp. 628-635.

* cited by examiner

Primary Examiner — James H Alstrum Acevedo
Assistant Examiner — Thea D' Ambrosio
(74) Attorney, Agent, or Firm — Lawson & Weitzen LLP; Sonia K. Guterman; Preeti T. Arun

(57) ABSTRACT

A peptide-POD with ability to penetrate and deliver fluorophores, siRNA, DNA and quantum dots to cells in culture and retinal and ocular tissues in vivo is provided herein. POD couples to adenovirus vectors, enhancing tropism for certain cells, potentially providing a safer and more efficacious method to deliver molecules to ocular and other tissues in vivo. POD constructs are therapeutic delivery vehicles for treating cells and tissues, including ocular cells and tissues suffering from retinal degeneration.

10 Claims, 44 Drawing Sheets

METHODS OF MAKING AND USING A CELL PENETRATING PEPTIDE FOR ENHANCED DELIVERY OF NUCLEIC ACIDS, PROTEINS, DRUGS, AND ADENOVIRUS TO TISSUES AND CELLS, AND COMPOSITIONS AND KITS

RELATED APPLICATION

This application is a continuation-in-part of and claims the benefit of PCT/US2008/010179 filed Aug. 28, 2008 in the PCT Receiving Office of the U.S. Patent and Trademark Office, which claims the benefit of U.S. provisional application Ser. No. 60/966,591 filed Aug. 29, 2007 in the U.S. Patent and Trademark Office, both of which are hereby incorporated by reference herein in their entireties.

GOVERNMENT SUPPORT

This invention was made with government support under grant EY014991 awarded by the National Institutes of Health. The government has certain rights in the invention.

TECHNICAL FIELD

Compounds conjugated to peptides sequences are provided, for penetrating cells and tissues, to deliver the compounds for vaccines and other medicaments, and methods of synthesis and kits.

BACKGROUND

Ocular diseases and diseases of other tissues arising from infection, cancer, autoimmune and inflammatory conditions remain important medical issues in spite of advances in the pharmaceutical sector. In particular, blindness is among the most common disabilities in the U.S. The condition endophthalmitis is an infection within an eye, which is a complicating factor for accessibility of current anti-infective treatments.

For most drugs including those ranging from low molecular weight entities to proteins, the plasma membrane is an impermeable barrier. Protein transduction domains (PTDs) are known from viral genomes, however improved and optimized amino acid sequences and methods for intracellular delivery remain important issues limiting the use of these sequences for drug delivery into cells.

Improved drug delivery compositions and methods are an important medical need.

SUMMARY

An aspect of the invention herein provides a method for delivery of a compound to a cell or a tissue for transduction into the cell or cells of the tissue, the method comprising: providing a peptide for overall delivery (POD) composition operably linked to the compound to obtain a conjugated compound, such that the POD comprises a protein transduction domain (PTD); and contacting the cell or tissue with the conjugated compound, such that the conjugated compound is transduced into the cell or the cells of the tissue. The term, "POD" was originally conceived as a peptide for ocular delivery, however in view of data showing that the peptide enhances delivery of a variety of compounds to many types of cells and tissues, the meaning of the term as used herein is a peptide for overall delivery.

In general, the POD includes an amino acid sequence denoted by the expression $(12221121)_x$ or $111(12221121)_x$ represented by numerical symbols, in which neutral small residues are designated by the numeral 1, and positively charged residues are designated by the numeral 2, and x is a whole number integer from 1 to 8. The first number on the left indicates the nature of the amino acid sequence at the N-terminal of the amino acid sequence; the number on the right indicates the nature of the amino acid residue at the C-terminal of the amino acid sequence. The numeral, "1" indicates that a residue of the peptide is any of the following neutral (uncharged) small amino acids: alanine; glycine; serine; threonine, asparagine and the like; and the numeral, "2" indicates that a residue of the peptide is any of the following positively charged amino acids: lysine, arginine and the like.

In various embodiments of the method, the POD has an amino acid sequence $(ARKKAAKA)_x$ or $GGG(ARKKAAKA)_x$ in which each amino acid is represented by the standard one letter code for amino acids, and x is a whole number integer from 1 to 8. In certain embodiments x is a whole number integer from 1-3, from 3-5, from 5-7, or from 6-8. GGGARKKAAKA is SEQ ID NO: 2; $GGG(ARKKAAKA)_2$ is GGGARKKAAKAARKKAAKA, SEQ ID NO:12; $GGG(ARKKAAKA)_3$ is SEQ ID NO: 13; GGG $(ARKKAAKA)_3$ is SEQ ID NO:1; $GGG(ARKKAAKA)_5$ is SEQ ID NO: 14; $GGG(ARKKAAKA)_6$ is SEQ ID NO:15; $GGG(ARKKAAKA)_7$ is SEQ ID NO: 16; and $GGG(ARKKAAKA)_8$ is SEQ ID NO:17.

In general, the method further includes, following contacting, observing the conjugated compound entering the cell or cells of the tissue without disrupting cell membranes. In certain embodiments, the method further includes observing localizing of the conjugated compound in cytoplasm or the nucleus. Alternatively, the method includes observing localizing of the conjugated compound in other areas of the cells, e.g., mitochondria, golgi complex.

In other embodiments of the method, the method includes, prior to contacting, formulating the conjugated compound as a medicament for diagnosing, prognosing, or treating a condition in a mammalian subject.

In various embodiments of the method, the compound is a nucleic acid, for example, the nucleic acid is at least one selected from the group of a cDNA, an mRNA, a tRNA, and a small interfering RNA siRNA. Alternatively, the nucleic acid is miRNA.

In other embodiments of the method, the compound is selected from the group of: a low molecular weight drug, a peptide, a lipid, a carbohydrate, and a protein including an antibody. For example, the low molecular weight drug has a molecular weight range of about 100 to about 5,000; or about 200 to about 3,000; or about 300 to about 1,500; or about 400 to about 1,400.

In general, the "target" cells or cells of a tissue is selected from the group of: ocular, oral, genital, cartilaginous (chondrocyte), liver, kidney, nerve, brain, epithelium, cardiac and muscular. In certain embodiments of the method, the cell or tissue is in culture. Alternatively, the cell or tissue is in vivo.

Another embodiment of the method further includes prior to contacting, PEGylating the POD composition linked to the compound, such that PEGylating includes reacting with a PEG reagent for addition of polyethylene glycol of about 10,000 average molecular weight in size. In other embodiments, PEGylating includes reacting with a PEG reagent for addition of polyethylene glycol of about 1,000; about 2,000; about 4,000; about 6,000; about 8,000; about 12,000; about 15,000; about 20,000; or about 30,000.

In embodiments of the method, contacting further includes providing the cell or tissue about 1 micromolar of the conjugated compound, or about 40 µg of the conjugated compound.

In related embodiments of the method, contacting further includes providing the cell or tissue about 2 micromolar, about 3 micromolar, about 5 micromolar, about 7 micromolar, about 8 micromolar, about 10 micromolar, or about 50 micromolar of the conjugated compound. Alternatively, contacting further includes providing the cell or tissue about 5 µg of the conjugated compound, about 10 µg of the conjugated compound, about 20 µg of the conjugated compound, about 25 µg of the conjugated compound, about 30 µg of the conjugated compound, about 35 µg of the conjugated compound, or about 50 µg of the conjugated compound.

In general, contacting further includes administering the conjugated compound to the subject by a route selected from the group consisting of: trans-ocular, intravitreal, topical, transdermal, intra-peritoneal, subcutaneous and intravenous. For example, administering includes a trans-scleral trans-choroidal injection into the subretinal space.

An embodiment of the method provides the conjugated compound that is the protein further includes synthesizing a nucleic acid encoding a genetic fusion of the compound amino acid sequence to the sequence of amino acids of the POD.

In related embodiments of the method, delivering further includes contacting the cell or the cells of the tissue with the nucleic acid encoding the fusion by expressing the nucleic acid in the cell or cells of the tissue, or expressing the nucleic acid in an expression system cell, isolating fusion protein, and contacting the cell or the cells of the tissue with isolated fusion protein.

In alternative embodiments of the method, providing the conjugated protein compound that is protein further includes chemically conjugating the compound to at least one amino acid of the POD amino acid sequence, for example, conjugating the compound to the amino acid residue.

In embodiments of the method, the conjugated protein compound or the conjugated peptide compound includes an immunogen or a vaccine.

In embodiments of the method, providing the conjugated protein compound further involves chemically synthesizing an amino acid sequence encoding a fusion of the compound to the sequence of amino acids of the POD.

Another aspect of the invention provides a composition for conjugating to a compound for delivery to a tissue or cell, the composition including an amino acid sequence selected from the group of GGG(ARKKAAKA)$_4$ (SEQ ID NO: 1) and (ARKKAAKA)$_4$ (SEQ ID NO: 3) such that the composition conjugated to the compound is transduced into a cell or cells of a tissue. The transduction activity is directed into the cell or the cells of a tissue, for example, selected from the group of: ocular including retina, retinal pigment epithelium, retinal ganglion, cornea, optic nerve, and embryonic retina; oral; genital; nervous; cartilaginous (chondrocyte); liver; kidney; epithelium; Cardiac; and muscular. In general, the composition further includes polyethylene glycol (PEG).

Another aspect of the invention provides a composition for conjugating to a compound for delivery into a cell or cells of a tissue, the composition including the amino acid sequence ARKKAAKA (SEQ ID NO: 4) or GGG(ARKKAAKA) (SEQ ID NO: 2), and optionally PEGylated derivatives thereof.

Another aspect of the invention provides a kit for synthesizing a conjugate including a peptide having at least one iteration of the amino acid sequence GGG(ARKKAAKA) (SEQ ID NO: 2) or ARKKAAKA (SEQ ID NO: 4) in a container, in which the sequence is optionally PEGylated, and instructions for use in conjugating the peptide to a compound).

In related embodiments, the kit further includes reagents for cross linking the sequence and synthesizing the conjugate.

Another aspect of the invention provides a method for delivery of a therapeutic compound into cells or tissue of an eye, the method including: providing a PEGylated peptide for overall delivery (POD) composition operably linked to the therapeutic compound to obtain a conjugated compound, such that the POD includes a protein transduction domain (PTD); and contacting the cell or tissue of the eye with the conjugated compound, such that the conjugated compound is transduced into the cell or the cells of the tissue; and, observing retinal degeneration in the cells or tissue of the eye.

In general, the POD includes an amino acid sequence denoted by the expression $(12221121)_x$ or $111(12221121)_x$ represented by numerical symbols, in which neutral small residues are designated by the numeral 1, and positively charged residues are designated by the numeral 2, and x is a whole number integer from 1 to 8. In certain embodiments x is a whole number integer from 1-3, from 3-5, from 5-7, or from 6-8. The numeral, "1" indicates that a residue of the peptide is any of the following neutral (uncharged) small amino acids: alanine; glycine; serine, threonine, asparagine and the like; and the numeral, "2" indicates that a residue of the peptide is any of the following positively charged amino acids: lysine and arginine. In certain embodiments of the method, the POD has an amino acid sequence (ARKKAAKA)$_x$ or GGG(ARKKAAKA)$_x$ such that each amino acid is represented by the standard one letter code for amino acids, and x is a whole number integer from 1 to 8. In another related embodiment, the POD includes an amino acid sequence (ARKKAAKA)$_x$ or GGG(ARKKAAKA)$_x$ and x is a whole number integer from 3 to 5. In certain embodiments x is a whole number integer from 1-3, from 3-5, from 5-7, or from 6-8.

In general, contacting the cells or tissue of the eye includes contacting in vivo. Alternatively, contacting the cells or tissue of the eye includes contacting in vitro.

In embodiments of the method, the conjugated compound includes a nucleic acid selected from a group consisting of: cDNA, mRNA, tRNA, and a siRNA. Alternatively, the nucleic acid is miRNA.

In related embodiments of the method, the nucleic acid encodes a protein. For example, the protein is a neurotrophic factor. In related embodiments of the method, the neutrophic factor is at least one selected from nerve growth factor (NGF), brain-derived neurotrophic factor (BDNF), neurotrophin-3 (NT-3), neurotrophin-4 (NT-4), glial cell line-derived neurotrophic Factor (GDNF), neurturin (NRTN), artemin (ARTN), and persephin (PSPN).

In general, observing reduced retinal degeneration further includes at least one method selected from a group consisting of determining: number of cells, eye function by electroretinography, cell activation, amount of apoptosis, and thickness of a tissue in the eye.

BRIEF DESCRIPTION OF THE DRAWINGS

FIG. 1 panel A shows that formalin-fixed human embryonic retinoblast cells after incubation with lissamine (Liss) conjugated POD (L-POD) for 1, 5 and 60 minutes aggregate L-POD on the cell surface within 1 minute and internalize within 5 min with a cytoplasmic (arrow) or punctate (arrowhead) pattern. Inset, lissamine only treated cells.

FIG. 1 Panel B shows that live cells exposed to L-POD have a pattern of localization different from formalin fixed cells, being mostly punctate, with no evidence of lissamine uptake.

FIG. 1 panel C shows treatment of HER cells with trypsin following incubation with L-POD, which did not reduce the number of lissamine-positive cells, indicating that L-POD is internalized and not simply membrane associated.

FIG. 1 panel D shows that uptake of L-POD is temperature dependent, and was substantially more efficient at 37° C. than at 4° C.

FIG. 1 panel E shows concentrations of FITC conjugated POD ranging from 0 to 2 nmol, which resulted in an increase in number of FITC-positive HER cells without an increase in propidium iodide-positive cells. TR, 1% Triton-X100.

FIG. 2 panel A shows that cysteine containing POD (C-POD) in $Na_2HPO_4$ buffer was capable of delivering plasmid DNA to human embryonic retinoblasts (HER).

FIG. 2 panel B shows electron microscopy of C-POD complexed with plasmid DNA in either 5% dextrose or $NazHPO_4$ buffer, horizontal bar equals 1 µm.

FIG. 2 panel C shows that C-POD delivered siRNA to HER cells and silenced GFP expression more efficiently than did siRNA alone.

FIG. 2 panel D shows that Biotin conjugated POD (B-POD) conjugated to quantum dots via a streptavidin bridge allowed uptake of the quantum dots within 15 minutes.

FIG. 2 panel E shows no evidence of quantum dot uptake at 120 min in HER cells was observed in the absence of B-POD.

FIG. 3 panel A shows that pre incubation of lissamine conjugated POD (L-POD) with either heparan sulfate or chondroitin sulfate reduced uptake of L-POD, and these same proteoglycans have little influence on uptake of an integrin-binding RGD-containing TRITC-labeled peptide.

FIG. 3 panel B shows that incubation of cysteine containing POD (C-POD) with *E. coli* prior to plating reduced number of colonies per plate in a concentration dependent manner.

FIG. 4 panel A shows that subretinal injection of lissamine conjugated POD (L-POD) into adult mice transduced approximately 40% of neural retina after 2 hours (4×) and was seen in several layers of the retina (20×). L-POD penetrated retinal pigment epithelium (RPE), inner and outer segments (IS, OS), cell bodies in the outer nuclear layer (ONL), cells in the inner nuclear layer (INL) and ganglion cells (GC)-40×.

FIG. 4 panel B shows that intravitreal injection of L-POD transduced approximately 85% of the neural retina within 2 hours (4×). Transduction was observed primarily of the GCL, INL (20×) and dendrites, with no significant transduction of RPE or ONL (40×).

FIG. 4 panel C shows delivery of biotin conjugated dots (QDPOD) to the subretinal space after 2 hrs permitted binding to rod outer segments and no significant uptake by the ONL. Longer incubation times of 20 hrs resulted in significant uptake by RPE and ONL. Insets are control quantum dots without POD at similar time points.

FIG. 4 panel D shows results obtained from intravitreal injection of QDPOD, with binding observed to inner limiting membrane and GCL after 2 hours and uptake within 20 hrs. Insets show results from control quantum dots without POD at similar time points. BF, brightfield.

FIG. 5 panel A shows data from incubation of lissamine conjugated POD (L-POD) with whole mouse eye in vivo for 45 min. The L-POD transduced most of the external ocular tissues including cornea, sclera and optic nerve. Lissamine only weakly stained cornea and sclera with no staining of optic nerve.

FIG. 5 panel B shows data from cross sections of eye in panel A observing that all of the outer surfaces of the eye were transduced by L-POD.

FIG. 5 panel C shows close examination of regions marked. A and B in panel B concluding that L-POD was taken up by corneal epithelium and sclera/choroid.

FIG. 5 panel D shows longitudinal and cross sections of optic nerve that indicate that outer layers of optic nerve were transduced by L-POD and not by lissamine at the 45 min time point. Insets are lissamine only controls.

FIG. 6 panel A is a set of drawings showing comparison of adenovirus serotype pIX C terminus and the pIX fusion protein containing G11(ARKKAAKA)$_3$ or pIX-PODs and schematic representation of the location of pIX-PODs trimers between the hexons.

FIG. 6 panel B is a set of bar graphs showing protein transduction following infection of Chang C or HER 911 cells by the viruses shown in FIG. 6 panel A, with or without pre incubation with chondroitin sulfate or heparan sulfate.

FIG. 7 panel A shows HER cells transfected with control pGFPHis.

FIG. 7 panel B shows HER cells transfected with pPODG-FPHis. These plasmids express control of His-tagged GFP or POD-GFP respectively. The data show that GFP localizes to the cytoplasm and nucleus (FIG. 7 panel A), and that POD-GFP localizes primarily to the nucleus (FIG. 7 panel B). Furthermore, POD-GFP appears to be concentrated in sub nuclear compartments (FIG. 7, panel B, arrowheads). BF, brightfield.

FIG. 8 panel B, left photograph, shows silver staining of purified protein indicated major bands of the predicted molecular weights for POD-GFP and GFP following analyses by PAGE. Anti-GFP Western blot confirmed that these proteins contained GFP (panel B, right photograph). CMV, cytomegalovirus; 6×His, His tag; BGH pA, bovine growth hormone polyadenylation signal; ITR, inverted terminal repeat; MLT, major late transcription unit; E1-E4; early regions 1-4 respectively.

FIG. 9 panel A is a bar graph showing POD-GFP or control GFP protein that was incubated with HER cells for 2 hours and the GFP-positive cells that were counted by FACS.

FIG. 9 panel B shows that POD-GFP entered cells and colocalized in part with Lysotracker, a red colored marker of late endosomes.

FIG. 10 panel A data show that control GFP was barely detectable above background auto fluorescence.

FIG. 10 panel B shows and that POD-GFP entered the RPE and photoreceptor cell bodies in the ONL. POD-GFP localized to photoreceptor nuclei in both a perinuclear and punctate manner (arrowheads). ONL, Outer nuclear Layer; INL, Inner Nuclear Layer; GCL, Ganglion Cell Layer; RPE, Retinal Pigment Epithelium

FIG. 11 panel A data show that control GFP could not be detected above background autofluorescence.

FIG. 11 panel B shows that POD-GFP was detected in the ganglion cells and a subset of cells in the inner nuclear layer (INL; arrowhead) and dendrites in the inner retina (arrow). ONL, Outer nuclear Layer; INL, inner Nuclear Layer; GCL, Ganglion Cell Layer; RPE, Retinal Pigment Epithelium

FIG. 12 panel A shows POD-GFP or control GFP protein that was injected into the intravitreal space of adult mice and eyes harvested after 6 hours and frozen sections prepared from lens revealed significant binding of POD-GFP to the lens capsule. Recombinant POD-GFP or control GFP proteins was applied to the eyes of anesthetized adult mice and eyes were washed and harvested 45 minutes later. The data show that control GFP does not substantially bind to ocular tissues and is not internalized, and POD-GFP binds to the entire corneal surface and can be readily detected in corneal wholemounts.

FIG. 12 panel B data from transverse sections of cornea indicate that POD-GFP localizes to the corneal epithelium.

FIG. 13 panel A data show that control GFP does not bind skin beyond that of auto fluorescence.

FIG. 13 panel B data show that POD-GFP binds to the epidermis. Although hair and papilla of the hair were also GFP-positive in sections exposed to POD-GFP, a significant portion of this signal was due to auto fluorescence. E, Epidermis; P, Papilla.

FIG. 14 panel A shows A549 cells which were transfected with C-POD/pCMVGFP complexes with or without prior serum-starvation for 48 hours, followed by FACS counting of the number of GFP-positive cells. The number of cells and the total GFP-intensity is substantially reduced in conditions inhibiting mitosis.

FIG. 14 panel B is a bar graph of relative light units (RLU) from A549 cells which were transfected with a C-POD/pCA-GLuc complex as in panel A, to quantitate protein levels. While expression increased after compaction in serum-starved cells ($p<0.05$), significantly less was observed than expression in dividing cells ($p<0.005$).

FIG. 14 panel C is a bar graph that shows that C-POD is able to deliver a luciferase transgene to primary cells in explants but not when injected into quiescent ocular tissue in vivo, pCAGLuc was added to explants of ocular tissue at two different N:P ratios. Compaction significantly increased luciferase expression relative to plasmid alone in RPE/sclera explants at an N:P ratio of 8.6 ($p<0.05$) but not at an N:P of 4.3 ($p>0.05$). In vivo assay for transfection was done by injection of 0.2 µg of pCAGLuc subretinally in 2 µl. There was no significant increase in luciferase expression in vivo using compacted plasmid.

FIG. 15 panel A shows that C-POD/DNA complexes form large aggregates in cell culture. Rhodamine labeled DNA was complexed with C-POD and added to HER cells in culture and observed after 24 hours.

FIG. 15 panel B shows that PEGylation of C-POD results in a gel shift of the protein band. C-POD was observed to be about a 3.5 kD peptide that migrated as a pentamer at about 17.5 kD. The addition of a 10 kD PEG increased the molecular weight to primarily 27.5 kD, with higher species also seen, indicating that a PEG molecule is predominantly added to only one C-POD peptide in a pentamer.

FIG. 15 panel C shows that PEGylated C-POD (PEG-POD) was able to compact DNA and this compaction was relieved upon prior degradation of the peptide with trypsin.

FIG. 15 panel D shows that PEG-POD/Rhodamine labeled DNA nanoparticles formed a diffuse stain across cells, and that PEGylation reduced formation of large aggregates. Scale bar=50 µm.

FIG. 18 panel A shows results for each individual injection, expressed in RLU/mg. Dotted line is equal to mean+3 SD.

FIG. 18 panel B shows the averages of the injections, expressed as RLU/mg. Data from PEG-CK30 injection fell below mean+3SD was not included.

FIG. 18 panel C shows the fold increase of nanoparticle injections compared to 1.2 μg naked DNA.

FIG. 20 panel A shows that PEG-POD protected DNA from DNAse I digestion. Serum nuclease activity decreases the half-life of plasmid DNA. In the absence of pronase only pCAGLuc, the naked plasmid, was able to migrate into the agarose gel while the nanoparticles PEG-POD~Luc remained compacted within the well. After a ten minute incubation with pronase each of pCAGLuc and PEG-POD~Luc DNA was observed to migrate in the gel. DNA or nanoparticles were incubated for 15 minutes with DNase I followed by a 10-minute incubation with pronase, which allowed visualization of the compacted DNA by degrading. PEG-POD. After the addition of 0.25 U DNase I, pCAGLuc has started to show signs of degradation, while pPOD~Luc is still intact. At a higher concentration with 2.5 U DNase I added, the pCAGLuc was completely degraded and was no longer visible, while pPOD~Luc showed only minor degradation.

FIG. 20 panel B shows that PEG-POD~Luc increased transfection efficiency in the lung. BALB/C mice were injected with 150 μL of 5% dextrose buffer containing either 40 μg pCAGLuc, 10 μg PEG-POD~Luc, or 40 μg PEG-POD~Luc. Luciferase expression was observed to have increased significantly above background when 10 μg PEG-POD~Luc (p<0.05) or 40 μg PEG-POD~Luc was injected (p<0.0001). Increasing the quantity of PEG-POD~Luc injected from 10 μg to 40 μg resulted in a significant increase in luciferase expression (p<0.0001). Naked plasmid alone did not significantly express luciferase above uninjected mice lung (p>0.05).

FIG. 21 panel A representative tracings from mice after 48 hours at −0 Log Light Intensity.

FIG. 21 panel B shows data from the waves analyzed for A and B-wave amplitude and plotted by Log Light Intensity. There was no significant difference between nanoparticle and buffer injections under any of the test conditions (p>0.05). Data showed that PEG-POD nanoparticles were non-toxic.

FIG. 22 panel A shows in vitro GDNF mRNA expression (ordinate) of plasmids expressing pCAGGDNF and pCADGFP (abscissa), respectively. The plasmid containing an expression cassette for rat GDNF expressed GDNF mRNA in vitro. Each condition, n=3. Mean±SEM.

FIG. 22 panel B is a photograph of a electrophoresis gel showing that PEG-POD compaction of pCAGGDNF prevents electrophoretic migration of the plasmid (left column), which was relieved by trypsin-mediated digestion of the protein (right column).

FIG. 22 panel C shows that PEG-POD compacted pCAG-GDNF (PEG-POD~GDNF) formed discrete spherical particles as examined by transmission electron microscopy (TEM). These particles were similar to other nanoparticles shown in previous figures herein. Analysis of the TEM images showed that the particles have a mean particle diameter of 175.9±28.6 nm. Scale bar=200 nm. The left and right microphotographs are 25,000 magnification and 64,000 magnification, respectively, of a representative TEM image.

FIG. 22 panel D shows data of in vivo GDNF mRNA expression (ordinate) for eyes injected in the subretinal space with PEG-POD nanoparticles compacted with pCAGGDNF or buffer, respectively (abscissa). Data show that injection of PEG-POD~GDNF resulted in a detectable level of rat GDNF mRNA expression (p>0.05). Each condition, n=9. Mean±SEM.

FIG. 23 panel D is a timeline of the procedure employed in Examples herein.

FIG. 23 panel A shows relative Caspase-3/7 activity data (ordinate) that was measured at various time points (hours, abscissa) following light exposure. Relative to the tissues of non-light treated mice, a 2.9-fold increase in Caspase-3/7 activity was observed in retina 48-hours post-light exposure (p<0.05), and a 1.9-fold increase in activity was observed in the RPE 24 hours post-light exposure (p<0.05). Data at two hours and 48-hours, n=4; 6 and 24-hours, 16-hours, n=7. Mean±SEM.

FIG. 23 panel B shows data for eye photoreceptor degeneration evaluated by measuring the thickness (μm) of the outer nuclear layer (ONL) for eyes having no light exposure (square), eyes injected subretinally with buffer and exposed to light (-x-), and uninjected eyes exposed to light (circle). ONL thickness (ordinate) was measured at distances (μm) extending from the optic nerve (abscissa). The ONL of uninjected eyes that were then exposed to light were observed to have fewer photoreceptor nuclei than unexposed and uninjected mice. Partial rescue was observed following subretinal injection eyes with buffer before light treatment. ONH is optic nerve head.

FIG. 23 panel C shows quantified wave amplitudes (μV, ordinate) for a-wave or b-wave amplitudes (abscissa) of mice eyes 7 days after performing each of the following: eyes exposed not exposed to light (open), eyes injected with buffer and exposed to light (cross-hatch), and eyes that were not injected and then were exposed to light (closed). In eyes absent injection and exposed to light, a significant decrease in the amplitudes of both the a-wave (p<0.005) and the b-wave (p<0.001) was observed. Impairment in light-response was partially prevented by subretinal injection of a buffer solution, although both the a- and b-waves were significantly lower in amplitude than those of control light untreated eyes (open bar, p<0.0001). Buffer, n=11; uninjected, n=3; non-light treated, n=4. Mean±SEM.

FIG. 23 panel D shows a timeline in days (d) for a procedure for examining effects of injections of nanoparticles into eyes and exposure to light. Subjects were injected into the superior hemisphere with either PEG-POD~GDNF nanoparticles, PEG-POD~Lux (sham nanoparticles) or buffer alone. Retinal degeneration was induced four days following subretinal injection by exposure to 4 hours of bright blue light. Following light exposure, effects of the treatment were assessed by measuring Müller cell activation (GFAP), apoptosis (TUNEL and nucleosome release assay), and ONL thickness and functional response (ERG) at two, seven and 14 days (d) post-light-treatment as indicated.

FIG. 24 panel A shows a set of photomicrographs of TUNEL stained retinal sections. Eyes were injected, exposed to light, sectioned, and stained 48 hours after light exposure. A significant reduction in apoptotic photoreceptors was observed in PEG-POD~GDNF-injected eyes (right column) compared to eyes injected with buffer (left column) or PEG-POD~Lux (middle column). C and S are the central and superior parts of the tissue. First row: cells visualized by DAPI; second row: cells stained with TUNEL; third row: merge of cells stained with TUNEL and cells stained with DAPI; and fourth row: magnification of the third row.

FIG. 24 panel B is a bar graph showing number of TUNEL-positive nuclei in the ONL including the superior hemisphere (left), the inferior hemisphere (middle), both the superior and inferior hemispheres (total, right). Eyes were injected with each of PEG-POD~GDNF (third, sixth, and ninth bars from left), PEG-POD~Lux (second, fifth, and eighth bars from left), and buffer (first, fourth, and seventh bars from left). Eyes injected with PEG-POD~GDNF were observed to have a significant decrease in the number of TUNEL positive nuclei in the ONL of the superior hemisphere (31.00±8.5 nuclei/section) compared to PEG-POD~Lux injected eyes (241.2±77.6 nuclei/section, p<0.005) and buffer injected eyes (197.9±39.7, p<0.0005). A similar trend in ONL thickness, in the inferior hemisphere, was observed to result for the different injections, i.e., injections of PEG-POD~GDNF had the largest thickness and injections of buffer had the smallest thickness. PEG-POD~GDNF, n=10; PEG-POD~Lux, n=5; Buffer, n=7. Mean±SEM.

FIG. 24 panel C shows quantification of absorbance at 405 mm (ordinate) of retinal tissue that was harvested 48 hours after treatment and/or injection or untreated control (abscissa). The retinal tissue was evaluated for apoptosis by a nucleosome release ELISA. Lower absorbance in the assay correlates with less nucleosome release, and is an indicator of decreased apoptosis. Eyes injected with PEG-POD~GDNF and exposed to light (second bar from left) showed 2.3-fold lower absorbance than PEG-POD~Lux injected eyes exposed to light (p<0.05, third bar from the left), 3.9-fold lower absorbance than buffer injected eyes exposed to light (p<0.05, fourth bar from the left), and 7.4-fold lower absorbance than uninjected eyes that had no light exposure (p<0.0005, first bar from the left). The data show that eyes injected with PEG-POD~GDNF and exposed to light had decreased apoptosis of photoreceptors and retinal tissue than untreated controls. Non-light treated and PEG-POD~GDNF, n=5; PEG-POD~Lux, Buffer, and uninjected, n=6. Mean±SEM. INL=Inner Nuclear Layer; ONL=Outer Nuclear Layer.

FIG. 25 panels A and B show that injecting eyes with PEG-POD~GDNF resulted in significant increases in the average ONL thickness, comparing both hemispheres in the retina to PEG-POD~Lux (p<0.01) or buffer (p<0.001)-injected eyes 7 days post-light treatment, and comparing to buffer (p<0.0001) 14 days post-light treatment. Representative images of the superior hemisphere adjacent to the ONH are shown at 20× magnification (left column) or 40× magnification (right column) for retinas injected with either PEG-POD~GDNF (first row), PEG-POD~Lux (second row), or buffer (third row). ONH=Optic Nerve Head; INL=Inner Nuclear Layer; ONL=Outer Nuclear Layer; DAPI=4',6-diamidino-2-phenylindole. 7 days: PEG-POD~GDNF and PEG-POD~Lux, n=6; Buffer, n=4. 14 days: PEG-POD~GDNF, n=4; PEG-POD~Lux, n=7; Buffer, n=6. Mean±SEM.

FIG. 26 panel A shows that injecting eyes with PEG-POD~GDNF significantly increased the ONL/INL ratio 7 days post-light treatment compared to PEG-POD~Lux- (p<0.05) or buffer-injected eyes (p<0.005). Limited or no difference was observed 7 days after light treatment between PEG-POD~Lux- and buffer-injected eyes (p>0.05). ONH, Optic Nerve Head; INL, Inner Nuclear Layer; ONL, Outer Nuclear Layer. PEG-POD~GDNF and PEG-POD~Lux, n=6; Buffer, n=4. Mean±SEM.

FIG. 26 panel. B shows that the ONL/INL ratio of PEG-POD~GDNF-injected eyes 14 days after light treatment was greater than eyes injected with PEG-POD~Lux- (p<0.05) or buffer (p<0.0001). Data demonstrates a significant difference between the overall thickness of PEG-POD~Lux- and buffer-injected eyes (p<0.05) at time 14 d after light exposure, and no significant difference for data comparing the ONL/INL ratio of the superior hemispheres only (p>0.05). ONH, Optic Nerve Head; INL, Inner Nuclear Layer; ONL, Outer Nuclear Layer. PEG-POD~GDNF, n=4; PEG-POD~Lux, n=7; Buffer, n=6. Mean±SEM.

FIG. 27 panel A shows thickness of the ONL (μm, ordinate) of eyes injected with materials (abscissa). Eyes were injected with PEG-POD~GDNF (first and fourth bars from left), PEG-POD~Lux (second and fifth bars from left), or buffer (third and sixth bars from the left). The average ONL thickness of PEG-POD~GDNF-injected retinas 7 days after light exposure was 24.5% greater than PEG-POD~LUX injected eyes (p<0.01) and 39.3% greater buffer injected eyes (p<0.0005). The average ONL thickness of PEG-POD~GDNF-injected retinas 14 days after light exposure was 23.6% greater than PEG-POD~Lux injected eyes (p<0.05), and 27.7% greater than buffer injected eyes (p<0.05). There was no significant difference observed in ONL thickness between eyes injected with buffer at seven days after light exposure and eyes injected with buffer 14 days after light exposure (p>0.05). Seven days: PEG-POD~GDNF and PEG-POD~Lux, n=6; Buffer, n=4. 14 days: PEG-POD~GDNF, n=4; PEG-POD~Lux, n=7; Buffer, n=6. Mean±SEM.

FIG. 27 panel B shows the ratio of average ONL thickness to average INL thickness (ordinate) of groups of eyes injected as follows (abscissa). Eyes were injected with PEG-POD~GDNF (first and fourth bars from left), PEG-POD~Lux (second and fifth bars from left), and buffer (third and sixth bars from the left), then exposed to light to analyze extent of degeneration. The calculated ONL/INL ratio of eyes injected with PEG-POD~GDNF was 38.5% greater than the ratio for eyes injected with PEG-POD~Lux (p<0.001) and 47.3% greater than the ratio for eyes injected with buffer (p<0.0005). The ONL/INL ratio remained higher for PEG-POD~GDNF-injected eyes at 14 days post-light exposure in comparison to the ratio for eyes injected with either PEG-POD~Lux or buffer. Injection of PEG-POD~GDNF correlated with an increased ONL/INL ratio at 14 days of 30.4% compared to injection of PEG-POD~Lux (p<0.05) and of 33.9% compared to injection of buffer (p<0.005). Seven days: PEG-POD~GDNF and PEG-POD~Lux, n=6; Buffer, n=4. Fourteen days: PEG-POD~GDNF, n=4; PEG-POD~Lux, n=7; Buffer, n=6. Mean±SEM.

FIG. 28 panel A shows averages of scotopic ERG voltages of a-amplitude waves for eyes injected with each of PEG-POD~GDNF, PEG-POD~Lux, or buffer. The voltages are shown in two views, with the right most readout (FIG. 28 panel B, right) showing an expanded view of the left readout (FIG. 28 panel A, left).

FIG. 28 panel B shows wave amplitude (μV) of the a-waves and b-waves measured for eyes injected as follows: PEG-POD~GDNF (open), PEG-POD~Lux (cross-hatched), and buffer (closed). It was observed that PEG-POD~GDNF injected eyes had 39% greater amplitude in the a-wave compared to PEG-POD~Lux (p<0.05) and 32% great amplitude compared to buffer injected eyes (p<0.05). The b-wave amplitude was increased in PEG-POD~GDNF injected eyes by 31% compared to PEG-POD~Lux (p<0.05) and by 27% compared to buffer injected eyes (p<0.05). There was no significant difference observed in the amplitude of either the a- or b-wave between PEG-POD~Lux- and buffer-injected eyes (p>0.05). PEG-POD~GDNF, n=12; PEG-POD~Lux, n=9; Buffer, n=11. Mean±SEM.

FIG. 30 panel A shows GFAP stained sections from control eyes not exposed to light (first row), and sections of retinas from eyes exposed to light and either injected with buffer (second row), or with PEG-POD~Lux (third row), or PEG-POD~GDNF (fourth row). It was observed that eyes exposed to light have a redistribution of GFAP (arrows) regardless of injection condition. Light treated eyes were observed to have GFAP localization restricted to astrocytes and the ends/feet of Müller cells at the inner limiting membrane. Eyes injected with PEG-POD~GDNF were observed to have an increased level of GFAP staining throughout the Müller cell extending towards the outer limiting membrane (arrows) compared eyes that received control injections.

FIG. 30 panel B shows relative GFAP fluorescence (ordinate) of groups of eyes injected and/or treated as follows (abscissa): retinas exposed to light and not injected, and retinas injected with PEG-POD~GDNF, PEG-POD~Lux, or buffer and exposed to light. A significant increase in GFAP staining was Observed in the inner retina in PEG-POD~GDNF injected eyes compared to that of control eyes (p<0.05). PEG-POD~GDNF, n=7; PEG-POD~Lux and Buffer, n=6; uninfected, n=3. Mean±SEM.

DETAILED DESCRIPTION

Figure 1A:
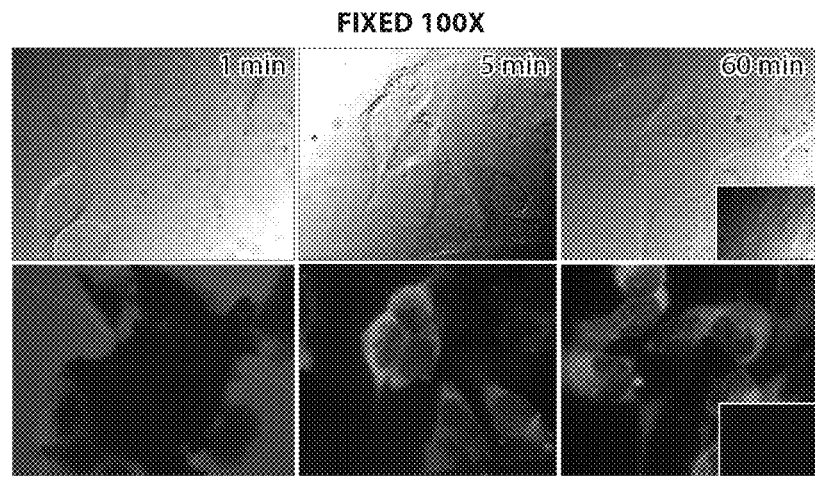
FIG. 1 is a set of photomicrographs and line graphs that show that POD is cell penetrating, non membrane-permeabilizing peptide.
Figure 1B:
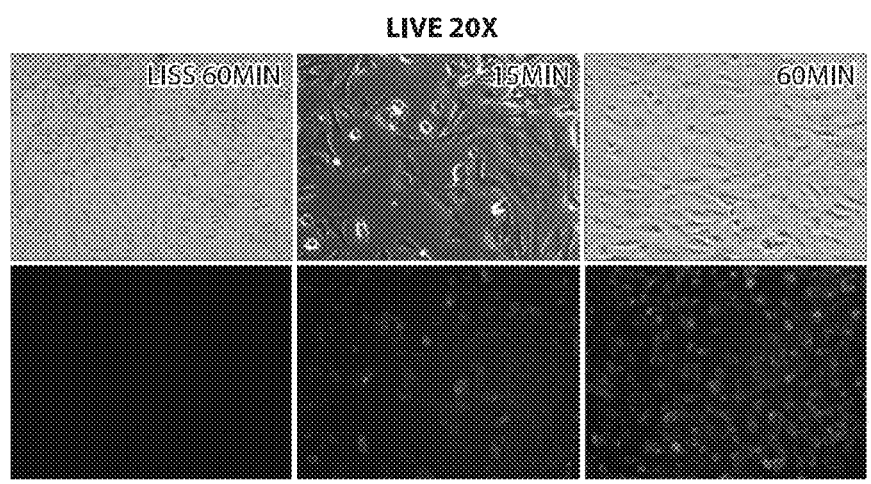
Figure 1C:
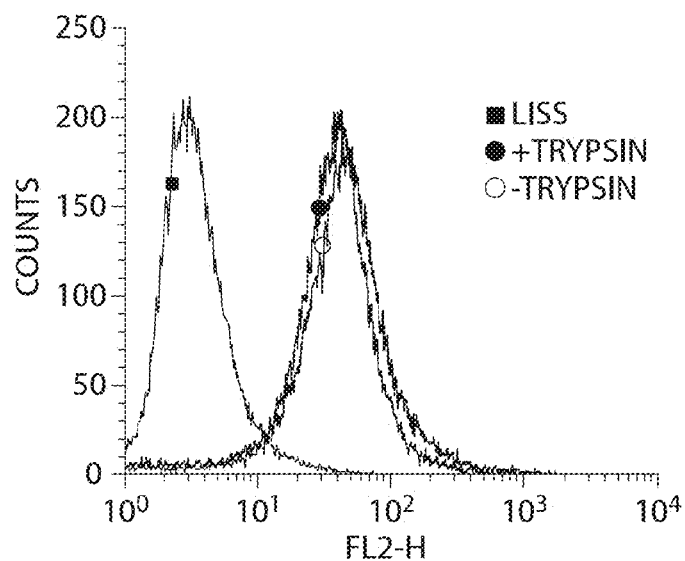
Figure 1D:
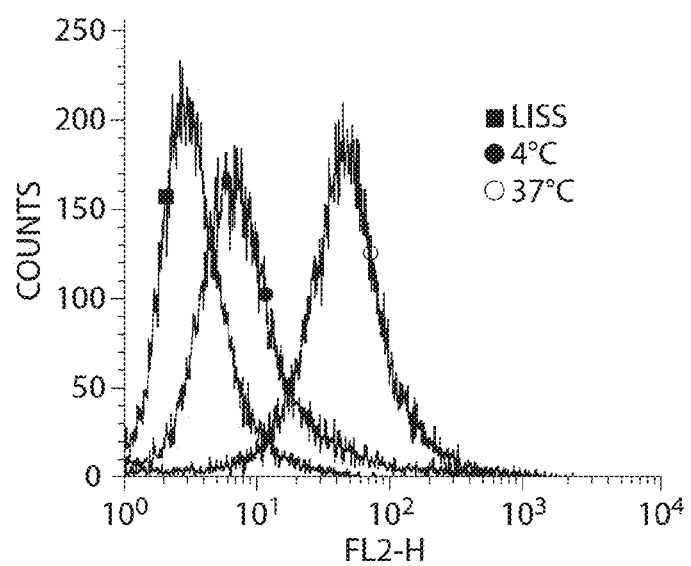
Figure 1E:
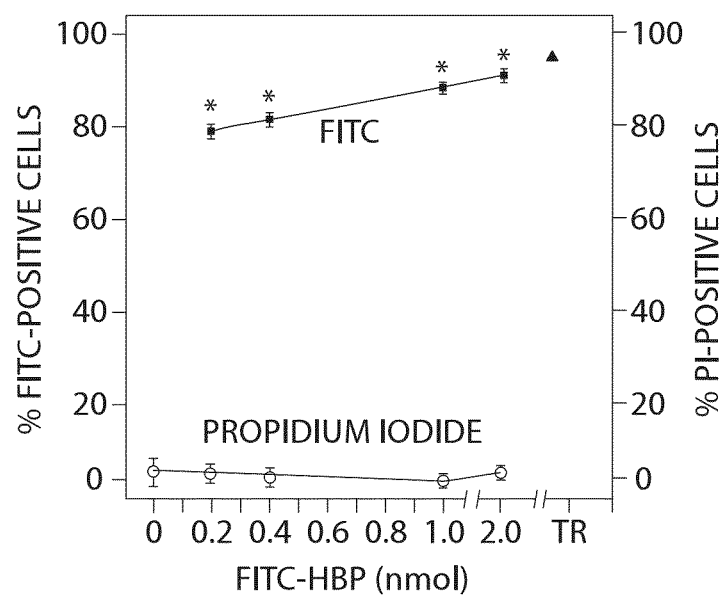
Figure 2A:
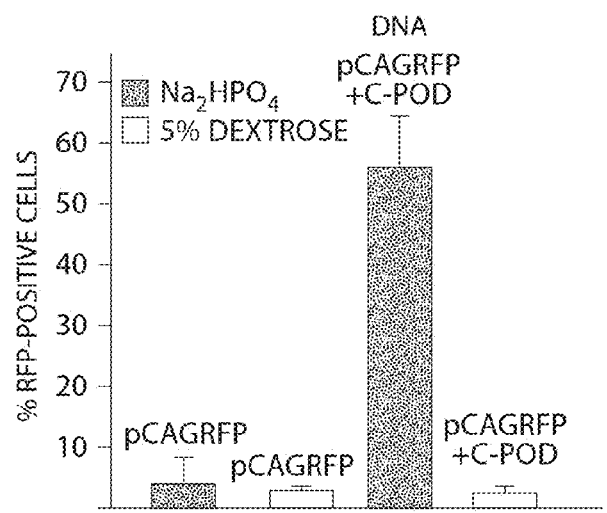
FIG. 2 is a set of bar graphs and photomicrographs showing POD-mediated delivery of small and large molecules in cell culture.
Figure 2B:
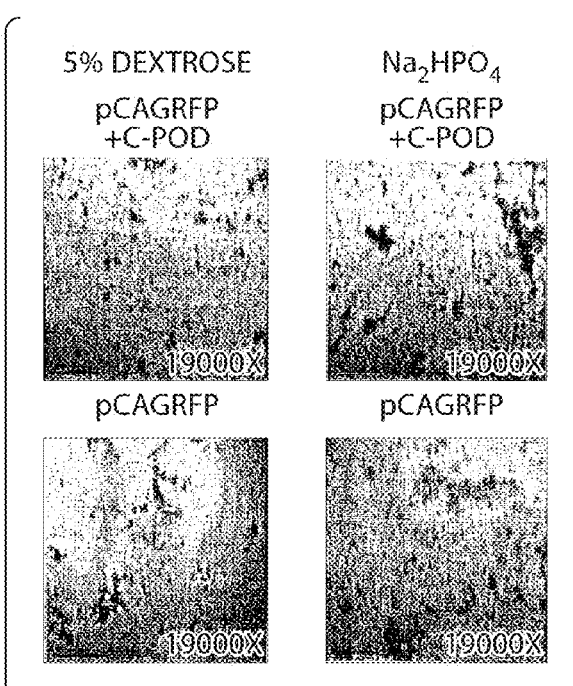
Figure 2C:
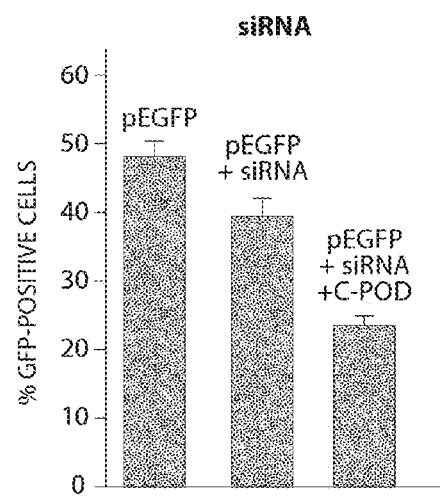
Figure 2D:
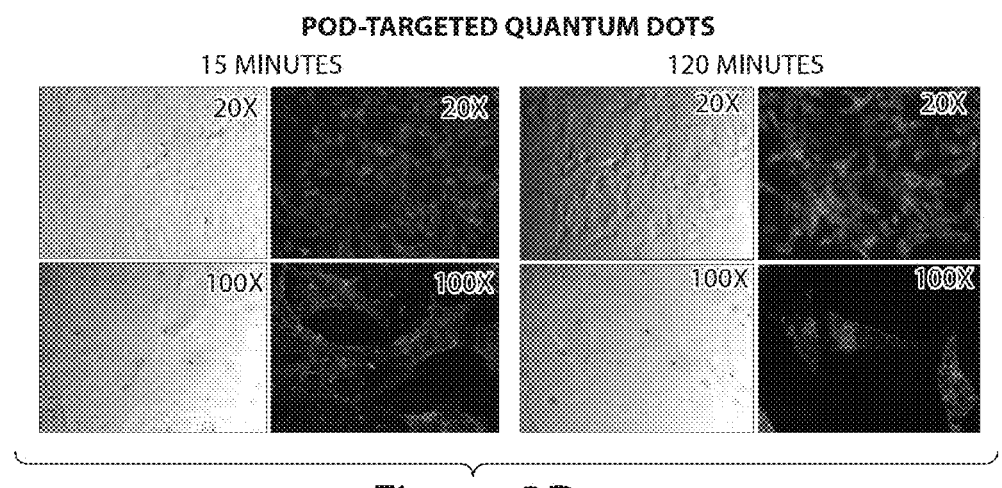
Figure 2E:
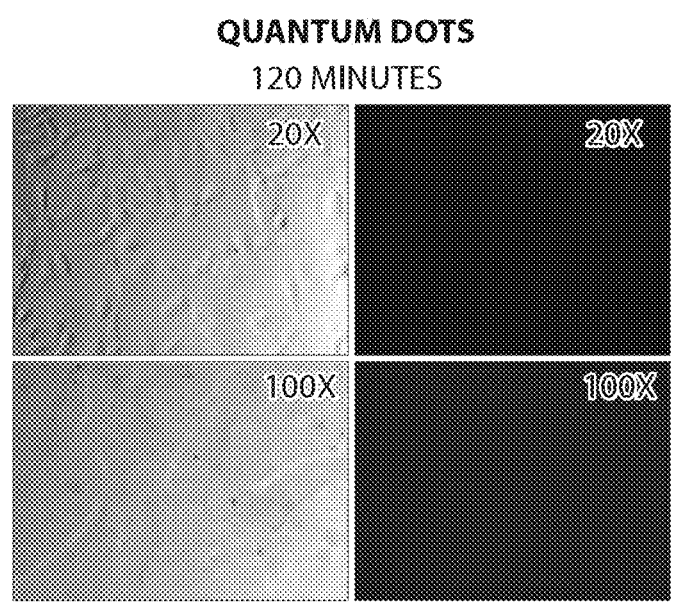

According to the National Institute of Health, ocular diseases that lead to blindness are one of the most common causes of disability in the United States [National Eye Institute (1999-2003). A Report of the National Eye Council, National Institutes of Health]. Some common diseases of the retina include age-related macular degeneration (AMD), retinitis pigmentosa (RP) and glaucoma, which are associated with degeneration of the retinal pigment epithelium, photoreceptors and retinal ganglion cells respectively Hartong, D T et al. 2006 Lancet 368:1795-1809; Rattner A et al. 2006 Nat Rev Neurosci 7: 860-872]. Infections, dystrophies or rejection of transplanted corneas are also amongst common causes of vision loss [Moffatt S L et al. 2005 Clin Experiment Opthalmol 33: 642-657]. Improvements in healthcare that have increased human life expectancy ironically result in a prediction of a significant increase in the frequency of diseases such as AMD or extend the burden associated with currently untreatable diseases such as RP [National Eye Institute (1999-2003). A Report of the National Eye Council, National Institutes of Health]. Therefore, the need to develop gene and drug delivery technologies for treatment of genetic and acquired ocular disorders is considerable.

As in other tissues, proteins or drugs directed at intracellular ocular targets need to be sufficiently polar to be easily administered [Kelder J et al. 1999 Pharm Res 16: 1514-1519]. However, for the majority of such molecules, the plasma membrane represents an impermeable barrier. Remarkably, a few select proteins such as the human immunodeficiency virus (HIV) Tat [Frankel A D et al. 1988 Cell 55: 1189-1193], herpes simplex virus (HSV) VP22 [Phelan A et al. 1998 Nat Biotechnol 16: 440-443], and the *Drosophila melanogaster* Antennapedia homeodomain [Derossi D et al. 1994 J Biol Chem 269: 10444-10450] possess the ability to traverse intact biological membranes. Interrogation of the structures of such proteins has led to the hypothesis that these proteins contain modules that confer the property of protein transduction and hence such sequences are generally referred to as protein transduction domains (PTD) as reviewed in [Dietz G P et al. 2004 Mol Cell Neurosci 27: 85-131]. PTDs can be isolated and incorporated into heterologous proteins and peptides, conferring protein transduction properties to such recombinant molecules. Initial experiments by several groups on the use of PTDs generated conflicting data and substantial debate regarding their properties and mode of action [Lundberg M et al. 2001 Nat Biotechnol 19: 713-714; Falnes P O et al. 2001 Biochemistry 40: 4349-4358]. Some of the issues addressed were whether the phenomenon of protein transduction was in fact real or only an artifact of fixation and whether the transduction was receptor, energy and/or temperature dependent [Richard J P et al. 2003 J Biol Chem 278: 585-590]. The PTD of both HIV Tat [Cashman S M et al. 2003 Mol Ther 8: 130-142] and HSV VP22 [Cashman S M et al. 2002 Mol Ther 6: 813-823] have valid transduction properties, as shown for ocular cell lines and tissues.

The examples herein were motivated to determine whether the peptide $GGG(ARKKAAKA)_4$, mw=3.5 Kd that has not previously been shown to have PTD properties can efficiently deliver small molecules including fluorescent probes and siRNA and large molecules including plasmid DNA and quantum dots to cells in culture and to murine ocular tissues in vivo. The results of Examples herein show that $GGG(ARKKAAKA)_4$ is an efficient peptide for ocular delivery (POD)' of small and large molecules across the plasma membrane, both in vitro and in vivo and hence have potential for the delivery of genes and drugs to human ocular tissues.

Almost 200 different loci and 130 different genes responsible for inherited retinal degeneration have thus far been identified, making retinal degeneration one of the most heterogeneous genetic disorders in humans (www.retnet.org). A large number of these genes are expressed exclusively in the photoreceptors or retinal neurons. Efficient delivery of therapeutic proteins into retinal cells is currently limited to the use of recombinant viruses for delivery of DNA expression cassettes—a potentially harmful approach that can in some cases lead to irreversible rearrangement of the host genome [Donsante A et al. 2007 Science 317: 477]. Hence, relatively intensive and significantly protracted preclinical studies need to be performed prior to the use of gene delivery in humans. Because of the large number of genes involved in retinal degeneration, preclinical testing of gene therapy approaches for every gene is cost and time prohibitive. Hence, accelerated progress towards the development of therapies for many retinal degenerations are achieved by the theoretically less risky approach of protein delivery—administration of which can be readily terminated upon the initial observation of any adverse events.

For example, although viral-mediated gene transfer of ciliary neurotrophic factor (CNTF) to animal models of retinal degeneration has been documented to be deleterious [Buch P K et al. 2006 Mol Ther 14: 700-709], phase I trials have been safely completed by use of encapsulated CNTF-producing cells that could be readily removed from the ocular compartment of retinitis pigmentosa patients [Sieving P A et al. 2006 Proc Natl Acad Sci USA 103: 3896-3901]. Should viral gene transfer of CNTF have been undertaken in those trials, the presumed risk to patients is greater and irreversible. For some retinal degenerations such as rhodopsin or peripherin/RDS—associated retinitis pigmentosa (RP), over-expression of therapeutic gene product is deleterious, as has been observed for both viral gene transfer [Sarra G M et al. 2001 Hum Mol Genet 10: 2353-2361] and in transgenic mice [Tan E et al. 2001 Invest Opthalmol Vis Sci 42: 589-600]. Hence, attempts at gene delivery to treat RP patients could theoretically promote a more rapid rate of photoreceptor degeneration than the absence of any therapy. Such a condition is not readily reversible with the majority of gene therapy approaches that typically rely on strong viral promoters or truncated cell-specific promoters. In the context of retinal degeneration, which is typically a slow progressive disease, it is envisaged herein that the use of slow release formulations or depots for long-term delivery of therapeutic proteins. However, the majority of macromolecules involved in retinal degeneration, or for that matter any disease, do not readily cross the plasma membrane and do not penetrate neural tissues such as the retina very efficiently.

Proteins exhibiting the unusual property of traversing lipid bilayers contain PTDs that can be chemically cross-linked to heterologous proteins, antibodies and enzymes and facilitate their transport across the plasma membrane [Fawell S et al. 1994 Proc Natl Acad Sci USA 91: 664-668; Anderson D C et al. 1993 Biochem Biophys Res Commun 194: 876-884]. Protein transduction was first reported a decade ago by Green and Frankel who independently demonstrated that the Human Immunodeficiency Virus (HIV) TAT protein was able to enter cells when added to the surrounding media [Frankel A D et al. 1988 Cell 55: 1189-1193; Green M et al. 1988 Cell 55: 1179-1188]. The most intensively studied PTDs are the *Drosophila* homeotic transcription factor ANTP (encoded by the antennapedia gene) and the Herpes Simplex Virus (HSV) VP22 [Joliot A et al. 1991 Proc Natl Acad Sci USA 88: 1864-1868; Joliot A H et al. 1991 New Biol 3: 1121-1134; Elliott G et al. 1997 Cell 88: 223-233]. A variety of additional cell penetrating peptides have since been discovered [Vives E et al. 2008. Biochim Biophys Acta 1786:126-138]. Apart from HIV TAT, there is very limited information available on the performance of PTDs in neuronal tissues in vivo.

A purpose of the Examples herein is to examine the potential of genetically fusing biologically relevant macromolecules such as whole proteins to POD to determine whether transduction properties are conferred upon the recombinant fusion protein in terms of delivery into the retinal photoreceptors and interneurons. For proof-of-principle, delivery of a POD-GFP fusion protein to retinal cells was examined in vitro and in vivo. Examples herein show that POD-fusion proteins allow the penetration and dispersion of macromolecules into retinal cells and tissues and hence have significant therapeutic applications for a variety of disorders of the CNS including blindness.

Figure 6A:
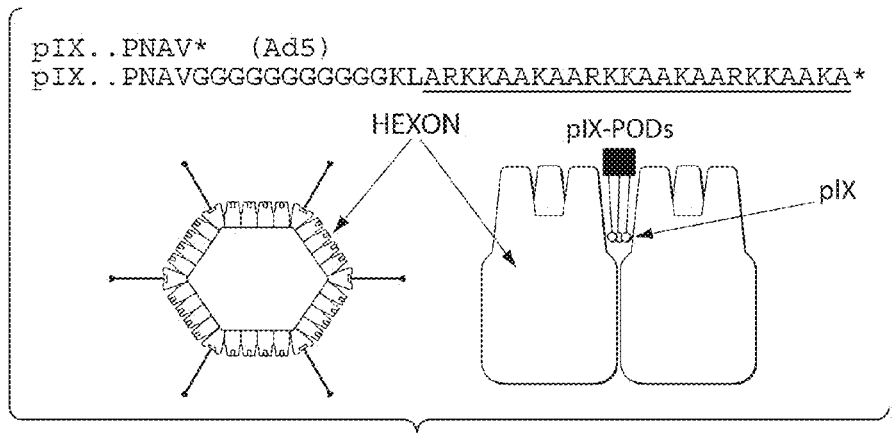
FIG. 6 is a set of drawings and bar graphs showing that adenovirus vectors pseudotyped with POD display altered tropism.
Figure 6B:
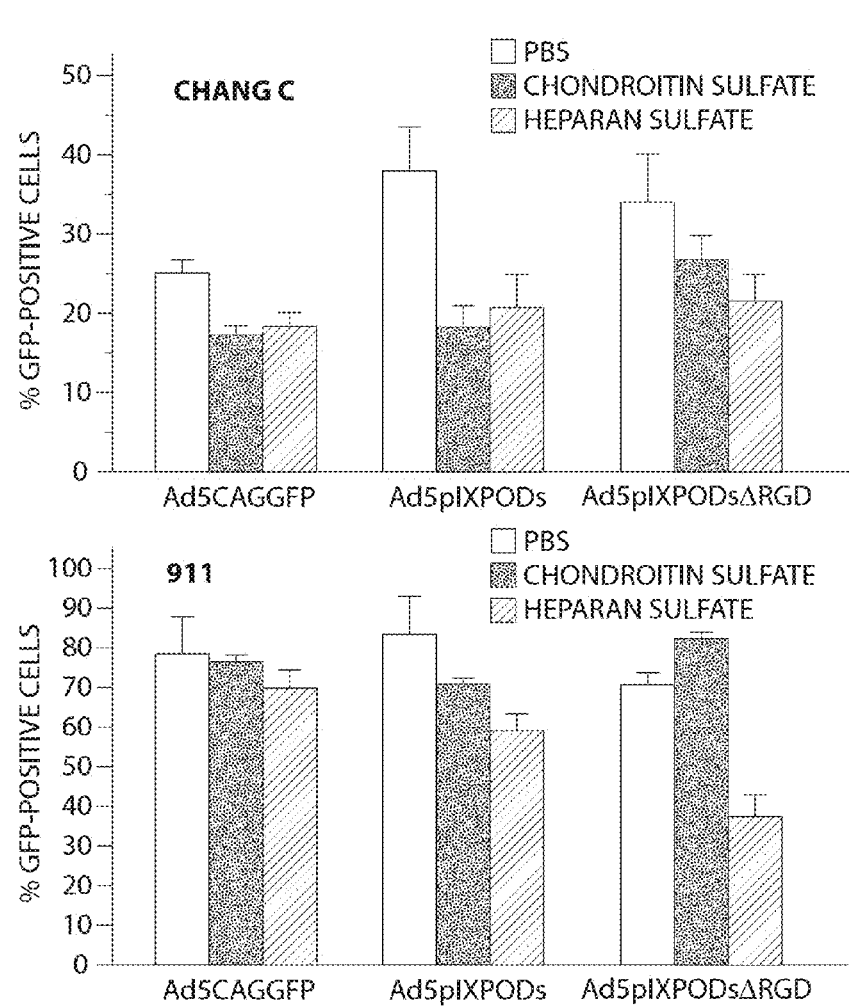

Examples herein show that POD is useful also to confer protein transduction properties to recombinant adenovirus vectors to enhance transduction of cells. Adenovirus entry is a two-step process, the first involving the binding of the knob domain of fiber to the coxsackie adenovirus receptor (CAR) [Bergelson J M et al. 1997 Science 275: 11320-1323]. The second step involves an interaction of cell surface $\alpha v \beta 5$ integrins with an RGD motif in the adenovirus penton base, allowing entry of the virus by receptor-mediated endocytosis [Wickham T J et al. 1993 Cell 73: 309-319]. To display POD on virion surfaces, genetically modified adenovirus backbone was obtained such that instead of expressing the coat protein IX (pIX), the recombinant virus instead expressed a fusion protein consisting of pIX and POD joined by a flexible polyglycine linker (FIG. 6 panel A). Since pIX is incorporated into virions as a trimer between each hexon, there are theoretically 240 PODs on the virion surface. Virions with full length pIX-POD fusion proteins i.e. pIX-G11(ARKKAAKA)$_4$ (SEQ ID NO: 3) were not rescued, however, virions displaying pIX-G11(ARKKAAKA)$_3$ (i.e. a plasmid carrying three iterations of SEQ ID NO: 4) were rescued. This recombinant virus also contained a GFP expression cassette regulated by the chicken βactin promoter in the deleted E1 region—Ad5pIXPODs.

To examine the potential role of POD on the virion coat in the absence of the RGD-avβ5 integrin interaction that is responsible for internalization of the virus by endocytosis, a virus was rescued with the above modification in combination with a deletion in the ROD domain of penton base-Ad5pIXPODsΔRGD. The parental control virus contains the same GFP expression cassette without any modifications to pIX or penton base (Ad5CAGGFP). As HER cells allow a productive viral infection and replication, transduction was examined of human conjunctival Chang C cells by each of the above viruses. Data show that whereas Ad5CAGGFP transduced 24.94±2.66% of Chang C cells, Ad5pIXPODs and Ad5pIXPODsΔRGD transduced 38.16±5.07 and 33.38±6.49% cells respectively at the same moi. It was concluded that PODs displayed on the surface of the adenovirus coat enhance transduction of Chang C cells by POD pseudotyped viruses. Pre-incubation of each virus with chondroitan sulfate reduced infection of Chang C cells by each of the viruses in a similar manner to the reduction seen with POD peptide. Pre incubation with chondroitan sulfate led to 17.19±1.13%, 16.65±0.61%, and 20.85±3.41% GFP-positive Chang C cells when infected with Ad5CAGGFP, Ad5pIXPODs, and Ad5pIXPODsΔRGD respectively. These data showed that these viruses are able to use POD during cell entry. Similarly, incubation with heparan sulfate also reduced infection of Chang C cells by each of the viruses by 29.12, 42.59, 34.04% for Ad5CAGGFP, Ad5pIXPODs and Ad5pIXPODsΔRGD respectively. The significant reduction in the rate of infection of all three viruses indicates that the proteoglycans play a greater role in viral infection than the integrins.

In HER cells, a cell line that allows viral replication, a greater rate of infection for each virus was observed. Ad5CAGGFP, Ad5pIXPODs and Ad5pIXPODsΔRGD infected 78.54±8.8%, 83.47±8.11%, and 69.67±3.86% of cells, respectively. The decrease in infection rate from the proteoglycans was less pronounced in HER cells when compared with Chang C cells. Pre-incubation with chondroitan sulfate reduced the number of infected cells to 75.73±1.88%, 69.82±0.61%, and 37.75±5.24% for Ad5CAGGFP, Ad5pIXPODs and Ad5pIXPODsΔRGD respectively. Only the Ad5pIXPODs and Ad5pIXPODsΔRGD results were significant and only the Ad5pIXPODsΔRGD was substantially inhibited. Heparin sulfate gave similar results for the Ad5CAGGFP and Ad5pIXPODs viruses with 69.46±5.18% (not significant) and 59.19±3.61% (p<0.05) of cells infected with virus. However, heparin sulfate appeared to enhance viral infection of Ad5pIXPODsΔRGD resulting in 81.02±2.58% positive cells.

A goal of Examples herein was to identify a peptide that would act efficiently as a PTD in ocular tissues such as the retina in vivo. Peptide design included selecting residues similar to that in the glycosaminoglycan binding regions of proteins abundantly observed in the retina. Two such proteins include acidic and basic fibroblast growth factors, aFGF and bFGF, respectively [Bugra K et al. 1997 J Mol Neurosci 9: 13-25]. The glycosaminoglycan chondroitan sulphate is known to be abundantly observed in adult retina. Heparan sulfate is abundantly expressed during development but its expression is substantially reduced in adult retina. Molecular modeling of protein-glycosaminoglycan interactions of aFGF and bFGF indicates that they contain basic heparin-binding regions of the form XBBBXXBX, where X and B are hydropathic and basic residues respectively [Cardin A D et al. 1989 Arteriosclerosis 9: 21-32]. Verrechio and colleagues [Verrecchio A et al. 2000 J Biol Chem 275: 7701-7707] have shown that peptides of the form (XBBBXXBX)n and (XB-BXBX)n where n=1 to 6, bind heparan. In addition, circular dichroism indicated that heparan-binding peptides converted from a charged coil to an alpha-helix upon heparan binding. Examples herein examine whether such peptides have protein transduction properties. A large number of different sequences were tested prior for protein transduction to the detailed examination of the exemplary POD presented in Examples herein.

U.S. Pat. No. 6,855,801 issued Feb. 15, 2005 (San Antonio et al.) shows peptides with strong affinity for glycosaminoglycans (GAGs) and proteoglycans (PGs) that interact with heparin. Sequences of peptides were based on consensus sequences XBBXBX and XBBBXXBX that were obtained from an analysis of a wide range of known heparin-binding proteins, using as many as 6 repeating units of these sequences. San Antonio et al. describe methods of using these peptides to provide cell adhesion to natural or synthetic surfaces, for heparin binding to block uptake and clearance of heparin, and to modulate actions of various PGs and GAGs.

U.S. Pat. No. 7,259,140 issued Aug. 21, 2007 (San Antonio et al.) describes additional peptides to 6,855,801 and having further residues such as cysteine and proline. These bind to heparin, and are used for example, in methods for reducing plasma heparin levels in a subject or to treat a mast cell serine protease-associated disorder.

Inconsistent findings characterize protein transduction. Therefore, Examples herein were designed to determine whether POD enters cells without using a method that involves fixation. Fixation leads to an artifact in terms of cellular localization of POD. While cytoplasmic localization was primarily observed in formalin fixed cells within 5 min, POD appeared punctate and localized perhaps to endocytic vesicles in live cells even after 60 min. Data herein show that at 1 min post incubation with POD, cells became opaque to 558 nm excitation, for examples as associated with aggregation or capping of cell-surface proteoglycans upon POD binding [Martinho R G et al. 1996 Mol Biol Cell 7: 1771-1788].

Evidence for uptake and not simply plasma membrane binding was demonstrated by treatment of live cells with trypsin, which failed to reduce the fluorescence associated with POD-transduced cells in Examples herein. Uptake was also shown to be temperature dependant.

A concern for a therapeutic agent for ocular delivery is potential toxicity during the process of traversing the cell membrane. To address this issue, uptake of propidium iodide by cells following incubation with POD was examined, and no increase in uptake was observed herein. These initial results show absence of indicia of toxicity. Data herein support a temperature-dependent mechanism, and no reduction in peptide uptake was observed in the presence of inhibitors of endocytosis. One such inhibitor, chlorpromazine, blocks clathrin coated pit-dependent endocytosis and genistein and filipin are known inhibitors of caveolae. As shown herein, no significant reduction in the uptake of L-POD was found with these inhibitors.

POD delivery of small molecules like siRNA efficiently across the plasma membrane has applications in treatment of ocular disease in humans. Currently several ongoing clinical trials target degradation of mRNA associated with either vascular endothelial growth factor (VEGF) or the receptor for the treatment of AMD [Michels S et al. 2006 Expert Opin Investig Drugs 15:779-793]. Indeed, use of siRNA for treatment of ocular disease in humans is at a particularly advanced stage of development relative to other diseases [Check E 2004 Nature 430:819]. Since the target of siRNAs is intracellular, efficient delivery across the plasma membrane in a non-toxic manner is highly desirable. POD potentially enhances siRNA delivery to the retina, allowing use of reduced concentrations of siRNA resulting in reduced toxic side effects associated with for example non-specific siRNA mediated silencing. Enhanced delivery of RNA molecules such as the aptamer macugen that is currently used to target VEGF in the treatment of AMD [Ng E W et al. 2006 Nat Rev Drug Discov 5: 123-132] is also be potentially achieved. POD as shown herein is useful to deliver siRNA and DNA in cell culture to study a variety of cellular processes.

Examples herein show that delivery of POD to the subretinal and intravitreal space resulted in penetration of a variety of cell types in the retina. Transduction of photoreceptors will have application in the treatment of diseases such as RP whereas transduction of RPE cells will have application in the treatment of AMD. Conversely, intravitreal injection allowed targeting of ganglion cells, degeneration of which is associated with glaucoma. POD-mediated delivery of growth factors or anti-apoptotic factors to the ganglion cells slows the rate of degeneration of such cells. While quantum dots took substantially longer to penetrate the retina than L-POD, perhaps due to their larger size, demonstration of the delivery of such large molecules is further support for the potential use of POD in the delivery of biologicals to the retina. Such biologicals include antibodies or antibody fragments such as avastin and lucentis respectively that are currently also used in the treatment of AMD [Pieramici D J et al. 2006 Expert Opin Biol Ther 6: 1237-1245]. It is envisioned herein that fusion proteins with POD are useful for rapid and enhanced penetration and delivery of therapeutic agents to retinal tissues.

Surprisingly, L-POD administered topically was found to reach the optic nerve within 45 min. This finding herein shows utility for treatment of diseases such as Leber's Hereditary Optic Neuropathy or Ischemic Optic Neuropathy. Penetration of the entire sclera and potentially the choroid allows non-invasive delivery of drugs or genes to choroidal blood vessels and endothelial cells, proliferation of which is involved in a variety of ocular diseases including AMD. Topical administration of POD-conjugated drugs to the cornea can enhance delivery of drugs to the corneal epithelium and into the anterior chamber. This is particularly useful as currently less than 1% of drug penetrates into ocular tissue following topical administration [Shell J W 1984 Surv Opthalmol 29: 117-128].

Examples herein show that adenovirus vectors can be modified by conjugation to POD to enhance uptake of adenovirus by human conjunctival Chang C cells. These examples have value in treatment of a variety of ocular and non-ocular diseases. Adenovirus vectors have been shown to be a viable and efficacious method of delivering genes to human ocular tissues in two clinical trials thus far [Campochiaro P A et al. 2006 Hum Gen Ther 17: 167-176; Chevez-Barrios P et al. 2005 J Clin Oncol 23: 7927-7935]. Since levels of heparan sulfate are increased in diseased retina [Landers R A et al. 1994 Neurochem 63: 737-750], the vectors described in this report have application for the treatment of a variety of retinal degenerations.

Cell-penetrating peptides have been shown to have microbicidal action, and those have structural and chemical similarities with naturally occurring antimicrobial peptides [Jung H J et al. 2006 Biochem Biophys Res Commun 345: 222-228; Zhu W L et al. 2006 Biochem Biophys Res Commun 349: 769-774; Palm C et al. 2006 Peptides 27: 1710-1716]. HIV TAT at concentrations of 3-24 µM has antifungal activity association with peptide binding nucleic acids and disrupting the cell cycle [Jung H J et al. 2006 Biochem Biophys Res Commun 345: 222-228]. Similarly, Pep-1-K, an analogue of Pep-1 designed specifically to target microbes, was shown to be strongly antibacterial in cultures of Gram-positive and Gram-negative bacteria with a minimal inhibitory concentration of 1-2 µM [Zhu W L et al. 2006 Biochem Biophys Res Commun 349: 769-774]. POD similar to Pep-1-K significantly reduced the number of gram-negative bacteria in culture, and significant reductions in colony number were seen herein with much lower concentrations of POD than was reported with the other peptides. A concentration as low as 0.3 µM was sufficient to reduce *E. coli* survival, a valuable finding as lower doses of POD are likely to be more clinically applicable injections of POD conjugated to therapeutic agents could possibly provide additional prophylaxis against infections resulting from invasive clinical procedures. Furthermore, POD antimicrobial activities indicate that POD is a therapeutic agent in an uncomplexed form.

Viral vectors for gene delivery have shown effective rescue of mouse models across a wide spectrum of disorders such as retinitis pigmentosa [Ali R R et al. 2000 Nat Genet 25: 306-310; Takahashi M et al. 1999 J Viral 73: 7812-7816; Bennett J 2000 Curr Opin Mol Ther 2: 420-425], Leber's congenital amaurosis (LCA) [Acland G M et al. 2001 Nat Genet 2001; 28: 92-95; Le Meur G et al. 2007 Gene Ther 14: 292-303; Narfstrom K et al. 2003 Invest Opthalmol Vis Sci 44: 1663-1672; Dejneka N S et al. 2003 Adv Exp Med Biol 533: 415-422] and age-related macular degeneration (AMD) [Reich S J et al. 2003 Curr Opin Genet Dev 13: 317-322]. However, adverse effects of viral application, including insertional mutagenesis and oncogenicity [Baum C et al. 2006 Hum Gene Ther 17: 253-263], as well as inflammation and immunogenicity [Muruve D A 2004 Hum Gene Ther 15: 1157-1166; Reichel M B et al. 1998 Gene Ther 5: 1038-1046], limit their application. Other concerns such as limitation of transgene size [Verma I M et al. 1997 Nature 389: 239-242] and the development of neutralizing antibodies [Bennett J et al. 1999 Proc Natl Mad Sci USA 96: 9920-9925] also restrict their use.

Previous efforts have been hampered by a lack of efficiency in vivo. The eye is an ideal organ for studying gene delivery vectors due to a wide variety of characterized diseases, compartmentalized structure and post-mitotic cell population [Bainbridge J W et al. 2006 Gene Ther 13: 1191-1197]. Cell culture transfection techniques such as electroporation [Bainbridge J W et al. 2006 Gene Ther 13: 1191-1197; Kachi S et al. 2005 Gene Ther 12: 843-851; Bejjani R A et al. 2007 Surv Ophthalmol 52: 196-208], cationic lipids [Kachi S et al. 2005 Gene Ther 12: 843-851; Brown M D et al. 2001 Int J Pharm 229: 1-21], and synthetic polymers such polyethylenimine [Godbey W T et al. 2001 Biomaterials 22: 471-480; Bieber T et al. 2002 J Control Release 82: 441-454] modified for ocular use in vivo have shown some evidence of efficacy but these techniques often result in significant toxicity.

Small positively charged peptides have been shown to bind DNA and to protect plasmids from degradation [Ziady A G et al. 2003 Mol Ther 8: 936-947; Thomas M et al. 2003 Appl Microbiol Biotechnol 62: 27-34]. A PEGylated lysine 30-mer (CK30PEG) transfects slowly dividing cells in the lung [Ziady A G et al. 2003 Mol Ther 8: 936-947] and has efficacy in post-mitotic ocular tissue [Farjo R et al. 2006 PLoS ONE 1: e38]. Short positively charged proteins, known as cell-penetrating peptides (CPPs), cross the plasma membrane and deliver biologically active molecules in vivo and in vitro [Lindgren M et al. 2000 Trends Pharmacol Sci 21: 99-103]. CPPs offer ease of preparation, rapid uptake, and low toxicity and immune response [Jones S W et al. 2005 Br J Pharmacol 145: 1093-1102]. HIV Tat is a CPP that compacts DNA and delivers it to cells in culture [Ignatovich I A et al. 2003 J Biol Chem 278: 42625-42636]. However, there has been little evidence of successful gene transfer using CPPs alone in vivo [Lindgren M et al. 2000 Trends Pharmacol Sci 21: 99-103].

Examples herein show that a synthetic cationic peptide referred to as POD, or "protein for ocular delivery," is able to penetrate the plasma membrane and deliver DNA and RNA in vitro [Johnson L N et al. 2008 Mol Ther 16: 107-114]. These results show that POD is able to deliver small and large molecules in vitro which could make it an ideal candidate for DNA delivery in vivo.

There are a number of barriers to gene delivery in vivo: stability in the extracellular space, transportation across the plasma membrane, escape from endosomes, and finally translocation across the nuclear pore. To this aim, POD was investigated for its ability to deliver DNA into the nucleus of post-mitotic cells in vivo by effectively overcoming these obstacles. Examples herein indicate that PEGylated POD, TAT, and polylysine can transfect cells in vivo at higher levels than plasmid alone and appear to show differential efficacies in vivo. Examples herein show that PEGylated cell penetrating peptides are gene delivery vectors.

A portion of the examples herein are in, "Cell Penetrating Peptide for Enhanced Delivery of Nucleic Acids, Drugs and Adenovirus to Ocular Tissues including Retina and Cornea", by Leslie N. Johnson, Siobhan M. Cashman and Rajendra Kumar-Singh, in the journal Molecular Therapy, 2007, 116: 107-114 subsequent to the filing of U.S. provisional application 60/966,591. A portion examples herein, "Cell. Penetrating Peptide POD Mediates Delivery of Recombinant Proteins to Retina, Cornea and Skin", submitted to the journal Molecular Therapy, and which is hereby incorporated by reference herein in its entirety.

Peptides used herein are synthesized or are obtained from a commercial supplier of custom peptides produced synthetically, e.g., by solid phase procedures. For example, peptide synthesis is performed using a solid-phase technique [Roberge et al. 995 Science 269:202] and automated synthesis is achieved, for example, using the 431A peptide synthesizer (available from Applied Biosystems of Foster City, Calif.).

As used herein, the phrase, "peptide for overall delivery" or POD, means a cationic peptide having a functional capability of penetrating a cell (CPP). POD peptide is linear or branched, and is synthesized as a sequence of amino acids. The amino acids in a POD include, (with one-letter symbols) naturally occurring amino acids glycine (G), alanine (A), valine (V), isoleucine (I), leucine (L), lysine (K), arginine (R), cysteine (C), methione (M), aspartic acid (D), glutamic acid (E), asparagine (N), glutamine (Q), serine (S), threonine (T), phenylalanine (F), tyrosine (T), proline (P), tryptophan (W), and histidine (H). Each of the naturally occurring amino acids each has a characteristic side chain or residue that confers properties including charge, i.e., neutral, positive charge, or negative, and hydrophobicity or hydrophilicity.

POD in certain embodiments has an amino acid sequence denoted by the expression $(12221121)_x$ or $111(12221121)_x$ represented by numerical symbols, in which residues of a certain class are designated by the numeral 1, residues of another class are designated by the numeral 2, and x is a whole number integer. The number on the left indicates the nature of the amino acid residue at the N-terminal of the amino acid sequence; the number on the right indicates the nature of the amino acid residue at the C-terminal of the amino acid sequence, and numbers thus designate the class of amino acid residue at each position in the sequence. Thus the expression represents a class of a plurality of specific amino acid sequences having characteristic amino acids at each position. The numeral, "1" indicates that a residue of the peptide in that location in the amino acid sequence is selected from among neutral (uncharged) small amino acids. The numeral, "2" indicates that a residue of the peptide in that location in the amino acid sequence is selected from among positively charged amino acids.

Neutral amino acids or uncharged amino acids include alanine, glycine, serine, threonine, asparagine and analogs and derivatives thereof and the like. Positively charged amino acids include lysine, arginine and analogs and derivatives thereof and the like.

The phrases "amino acid" and "amino acid sequence" include without limitation one or more components that are both naturally occurring and also that are non-naturally occurring, viz., amino acid derivatives and/or amino acid analogs structurally related to and substituted for one or more naturally occurring amino acids indicated according to that sequence. In an amino acid sequence having one or more alanine residues, a portion of one or more of those residues can be substituted with homoalanine. In an amino acid sequence having one or more arginine residues, a portion of one or more of those residues can be substituted with homoarginine. Further, an amino acid sequence having one or more non-peptide or peptidomimetic bonds between two adjacent residues, is included within this definition.

As used herein, the word "protein" means a naturally occurring amino acid sequence, generally encoded by a gene or portion thereof. As used herein, the terms "neurotrophic protein" or neurotrophins refer to a family of proteins that induce or influence the survival, development and function of neuronal cells. Neurotrophic proteins are growth factors and include nerve growth factor (NGF), brain-derived neurotrophic factor (BDNF), neurotrophin-3 (NT-3), neurotrophin-4 (NT-4), glial cell line-derived neurotrophic Factor (GDNF), neurturin (NRTN), artemin (ARTN), and persephin (PSPN). Major downstream pathways activated by neurotrophic proteins include the phosphatidylinositol-3-kinase-Akt pathway, PKC, and the mitogen-activated protein kinase pathway-14. These pathways generally activate one or more transcription factors including API, NF-κB and FOXOs. Classes of genes induced by neurotrophic proteins include those encoding anti-apoptotic proteins, antioxidant enzymes, and proteins involved in energy metabolism and ion homeostasis.

As used herein, the phrase "operably linked" means a juxtaposition wherein the components so described are in a structural proximal relationship resulting in function in an intended manner (e.g., relationships including covalent and ionic bonds, and genetic fusion).

As used herein, terms "PEGylating" and "PEGylation" means treatment, contact or attachment of a component or components to at least one molecule of the polymer polyethylene glycol (PEG), or a polyethylene glycol analog, such that the component and PEG are covalently bound. PEG is a polymer of ethylene oxide also known as poly(ethylene oxide), polyoxyethylene and sold under the trade name Carbowax (Dow). The polyethylene glycol or polyethylene glycol analog is not limited by any particular length or weight, and suitable PEG for PEGylation herein includes a molecular weight from about 300 to about 100,000 or larger. Preferable molecular weights include 2,500; 5,000; 7,500; 10,000; 15,000; 20,000; and 30,000. As used herein, the phrase "PEGylated peptide" means an amino acid sequence having at least one polyethylene glycol (PEG) molecule covalently bound to an atom of an amino acid or analog in the sequence.

As used herein, the phrase "conjugated compound" refers to at least two components, a first component and a second component, that are generally covalently bound. In particular, the conjugated compound has a component that is a CPP or POD, and accordingly is carried with the CPP or POD into a cell. For example, a first component is a PEGylated peptide for overall delivery (POD) and a second component that is a therapeutic compound. These are operably linked, e.g., covalently linked, to form a conjugated compound.

Pharmaceutical Compositions

Pharmaceutical compositions are provided herein, such that these compositions include a peptide covalently linked to a target molecule of choice, and optionally comprise a pharmaceutically acceptable carrier. In certain embodiments, these compositions optionally further comprise one or more additional therapeutic agents. In certain embodiments, the target of choice and/or the additional therapeutic agent or agents are selected from the group of growth factors, anti-inflammatory agents, vasopressor agents, collagenase inhibitors, topical steroids, matrix metalloproteinase inhibitors, ascorbates, angiotensin II, angiotensin calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), lieu differentiation factor (NDF), hepatocyte growth factor (HGF), B vitamins such as biotin, and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences Ed. by Gennaro, Mack Publishing, Easton, Pa., 1995 describes a variety of different carriers that are used in formulating pharmaceutical compositions and known techniques for the preparation thereof. Some examples of materials that are pharmaceutically acceptable carriers include, but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Therapeutically Effective Dose

In yet another aspect, the methods of treatment include the treatment of an ocular condition or a condition affecting another organ or tissue by contacting, for example, the eye with a pharmaceutical composition described herein. Thus, the invention provides methods for the treatment of the ocular condition comprising administering to a subject in need thereof, a therapeutically effective amount of a pharmaceutical composition comprising active agents that include the peptide conjugate, in such amounts and for such time as is necessary to achieve the desired result. It will be appreciated that this encompasses administering an inventive pharmaceutical as a therapeutic measure to promote the spreading of tear film Onto the corneal and conjunctival surface, or as a prophylactic measure to minimize complications associated with the ocular condition (e.g., as a wound irrigation solution during and/or following surgery or treatment of inflammatory conditions with anti-histamines). In certain embodiments, a "therapeutically effective amount" of the pharmaceutical composition is an amount effective for promoting healing and/or improvement of the condition. The compositions, according to the method, are administered using any amount and any route of administration effective for treating the cell, tissue or organ. Thus, the expression "amount effective for promoting the treating the condition", as used herein, refers to a sufficient amount of composition to promote the healing and return to normal of physiology of the cell, tissue or organ. The exact dosage is chosen by the individual physician in view of the patient to be treated. Dosage and administration are adjusted to provide sufficient levels of the active agent(s) or to maintain the desired effect. Additional factors which are taken into account include the severity of the disease state, e.g., extent of the condition, history of the condition; age, weight and gender of the patient; diet, time and frequency of administration; drug combinations; reaction sensitivities; and tolerance/response to therapy. Long acting pharmaceutical compositions might be administered several time points a day, every day, 3 to 4 days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions will be decided by the attending physician within the scope of sound medical judgment. For any active agent, the therapeutically effective dose can be estimated initially either in cell culture assays or in animal models, as shown in examples herein, usually mice, rabbits, dogs, or pigs. The animal model is also used to achieve a desirable concentration range and route of administration. While direct application to the eye is envisioned as the route of administration, such information can then be used to determine useful doses and additional routes for administration in humans. A therapeutically effective dose refers to that amount of active agent that ameliorates the symptoms or condition. Therapeutic efficacy and toxicity of active agents can be determined by standard pharmaceutical procedures in cell cultures or animals, e.g., ED50 (the dose that is therapeutically effective in 50% of the population) and LD50 (the dose that is lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies are used in formulating a range of dosages for human use.

Administration of Pharmaceutical Compositions

After formulation with an appropriate pharmaceutically acceptable carrier in a desired dosage, the pharmaceutical compositions herein are administered to humans and other mammals topically such as ocularly (as by powders, ointments, or drops), i.e., as applied directly to the eye. Alternative additional routes such as oral, rectal, parenteral, intracisternal, intravaginal, intraperitoneal, bucal, or nasal, depending on the severity of the condition being treated, are envisioned.

Liquid dosage forms for ocular administration include buffers and solubilizing agents, preferred diluents such as water, preservatives such as thymosol, and one or more biopolymers or polymers for conditioning the solution, such as polyethylene glycol, hydroxypropylmethylcellulose, sodium hyaluronate, sodium polyacrylate or tamarind gum.

Liquid dosage forms for oral administration include, without limitation, pharmaceutically acceptable emulsions, microemulsions, solutions, suspensions, syrups and elixirs. In addition to the active agent(s), the liquid dosage forms contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of the pharmaceutical compositions herein include ointments, pastes, creams, lotions, gels, powders, solutions, sprays, inhalants, or patches. The active agent is admixed under sterile conditions with a pharmaceutically acceptable carrier and preservatives or buffers as required. For example, ocular or cutaneous infections are treated with aqueous drops, a mist, an emulsion, or a cream. Administration is therapeutic or is prophylactic. Prophylactic formulations are applied to the site of potential wounds, or to sources of wounds, such as contact lenses, contact lens cleaning and rinsing solutions, containers for contact lens storage or transport, devices for contact lens handling, eye drops, surgical irrigation solutions, ear drops, eye patches, and cosmetics for the eye area, including creams, lotions, mascara, eyeliner, and eyeshadow, and to opthalmological devices, surgical devices, audiological devices or products that contain the compositions herein (e.g., gauze bandages or strips), and methods of making or using such devices or products. These devices are coated with, impregnated with, bonded to or otherwise treated with a composition herein.

The ointments, pastes, creams, and gels contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Powders and sprays can contain, in addition to the agents of this invention, excipients such as talc, silicic acid, aluminum hydroxide, calcium silicates, polyimide powder, or mixtures of these substances. Sprays can additionally contain customary propellants such as chlorofluorohydrocarbons.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions are formulated according to the known art using suitable dispersing or wetting agents and suspending agents. The sterile injectable preparation is also a sterile injectable solution, suspension or emulsion in a nontoxic parenterally acceptable diluent or solvent, for example, as a solution in 1,3-butanediol. Among the acceptable vehicles and solvents employed are water, Ringer's solution, U.S.P. and isotonic sodium chloride solution. In addition, sterile, fixed oils are conventionally employed as solvents or suspending media. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. To prolong the in vivo effect of an active agent, it is often desirable to slow the absorption of the agent from subcutaneous or intramuscular injection. Delayed absorption of a parenterally administered active agent is accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly (orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of compositions herein with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type are also employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) are admixed with at least one inert diluent such as sucrose or starch. Such dosage forms also include, as is normal practice, additional substances other than inert diluents, e.g., tableting lubricants and other tableting aids such a magnesium stearate and microcrystalline cellulose. In the case of capsules, tablets and pills, the dosage forms also include buffering agents. They optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

Examples herein show that a short positively-charged peptide referred to as POD (or peptide for ocular delivery) is capable of crossing the plasma membrane of cells in vitro, and crossing most ocular neuronal cell types in vivo, including RPE, photoreceptors and ganglion cells [Johnson L N, et al. 2009 Vision Res]. POD retains this cell penetrating ability when fused with much larger molecules, such as GRP and Quantum dots [Johnson L N, et al. 2009 Vision Res; Johnson L N, et al. 2008 Mol. Ther. 16(1): 107-114]. Analysis of data demonstrated that PEGylation of POD (PEG-POD) permits compaction of plasmid DNA into 120-150 nm nanoparticles [Read S P, et al. 2009 J Gene Med]. Upon ocular delivery, PEG-POD nanoparticles transfect the post-mitotic retinal pigment epithelium (RPE) approximately 200-fold more efficiently than plasmid. DNA [Read S P, et al. 2009 J Gene Med].

Over 40 different genes have been documented to cause RP, with over 100 mutations in the rhodopsin gene alone. Another retinal disease, AMD, is complex, involving a variety of genetic and environmental influences [Ambati J, et al. 2003 Surv Ophthalmol. 48(3): 257-293]. The broad etiological spectrum of retinal degeneration makes it practical to consider use of neurotrophic factors as therapeutic agents, for a mutation independent approach to treatment. Neutrophic factors rescue a number of animal models of retinal degeneration [Wenzel A, et al. 2005 Prog Retin Eye Res. 24(2): 275-306]. Data from a Phase II clinical trial in which RP patients received intravitreal implants of encapsulated cells secreting ciliary neurotrophic factor (CNTF) show that a subset of patients exhibited an improvement in visual acuity [Sieving P A, et al. 2006 Proc Natl Acad. Sci. 103(10): 3896-3901]. Glial Cell Line-Derived Neurotrophic Factor (GDNF) is a member of a family of neurotrophic factors, activity of which prevents photoreceptor cell loss in both inherited models of retinal degeneration [Frasson M, et al. 1999 Invest Ophthalmol Vis Sci. 40(11): 2724-2734; McGee Sanftner L H, et al. 2001 Mol Ther. 4(6): 622-629; Lawrence J M, et al. 2004 Invest Opthalmol Vis Sci. 45(1): 267-274], and in environmentally-induced models of retinal damage [Wu W C, et al. 2002 Invest Opthalmol Vis Sci. 43(11): 3480-3488; Wu W C, et al. 2004 Mol. Vis. 10: 93-102].

Apoptosis represents a final or late step in retinal degeneration for both RP [Wenzel A, et al. 2005 Prog Retin Eye Res. 24(2): 275-306; Chang G Q, et al. 1993 Neuron. 11(4): 595-605] and AMD [Dunaief J L, et al. 2002 Arch Opthalmol. 120(11): 1435-1442]. Apoptosis-mediated cell death has been induced in rodent retina by exposure to light causing synchronized and rapid cell death within the retina. Rats exposed to high levels of light have been observed to have morphological changes to both the RPE and photoreceptors, indicating that both of these cell types are affected by light exposure [Gorgels T G, et al. 1995 Invest Opthalmol Vis Sci. 36(5): 851-863]. The pathogenic effects of lipofuscin deposits, such as lipofuscin component A2E, observed in AMD patients could be attributable to blue and visible light exposure [Weale, R A. 1989 Photochem Photobiol. 50(3): 429-438]. Light per se is an accelerator of R P in patients [Heckenlively J R, et al. 1991 Arch Opthalmol. 109(1): 84-91; Paskowitz D M, et al. 2006 Br J. Opthalmol. 90(8): 1060-1066] and in animal models of RP [Wenzel. A, et al. 2005 Prog Retin Eye Res. 24(2): 275-306; Naash M L, et al. 1996 Invest Ophthalmol Vis Sci. 37(5): 775-782; Organisciak D T, et al. 2003 Invest Opthalmol Vis Sci. 44(2): 486-492; Vaughan D K, et al. 2003 Invest Opthalmol Vis Sci. 44(2): 848-855]. Thus, light induced retinal degeneration represents an in vivo model applicable across a wide spectrum of degenerative disorders.

To examine the efficiency of PEG-POD mediated gene therapy, PEG-POD nanoparticles were generated expressing GDNF (PEG-POD~GDNF) and investigated for their ability to rescue photoreceptor degeneration in adult mice exposed to bright blue light. Examples herein show that retinas treated with PEG-POD~GDNF nanoparticles exhibit significantly reduced photoreceptor loss, resulting in a significant increase in photoreceptor functional response measured by electroretinography (ERG). Without being limited to any particular theory or mechanism or action, it is envisioned that PEG-POD delivers genes to retina at therapeutic levels, sufficient to cause structural and functional rescue of acute retinal damage.

Examples herein demonstrate that PEGylated cell penetrating peptide (CPP) PEG-POD delivered a therapeutic transgene in vivo and partially rescued retinal degeneration both histologically and functionally. The synthetic peptide POD was a CPP with a high efficiency of uptake in the retina and delivered plasmid DNA in vitro. PEGylation of POD allowed for in vivo transfection of the retinal pigment epithelium (RPE) at levels significantly higher than other PEGylated CPPs, published as [9] "POD Nanoparticles Expressing GDNF Provide Structural and Functional Rescue of Light-Induced Retinal Degeneration in an Adult Mouse" by Sarah Parker Read, Siobhan M. Cashman, Rajendra Kumar-Singh: submitted to the journal Molecular Therapy, which is incorporated herein by reference in its entirety. To test the physiologic relevance of PEG-POD mediated gene transfer, a potential therapeutic transgene encoding rat GDNF was compacted and assessed for efficacy to slow the progression of photoreceptor cell death in a mouse model of light-induced retinal degeneration.

Effectors of photoreceptor apoptosis differ as a function of regimens of light stimuli, thus conditions that would mimic the apoptotic cascade in human RP were here investigated. Light-induced photoreceptor degeneration pathways including those induced either by short-term exposure to bright light, or by prolonged exposure to low light intensity [Hao W, et al. 2002 Nat. Genet. 32(2): 254-260]. Blue light is especially damaging due to its increased activation of rhodopsin, photobleaching both in vitro [Williams T P. 1964 J Gen Physiol. 47: 679-689] and in vivo [Grimm C, et al. 2000 Invest Ophthalmol Vis Sci. 41(12): 3984-3990].

Figure 24A:
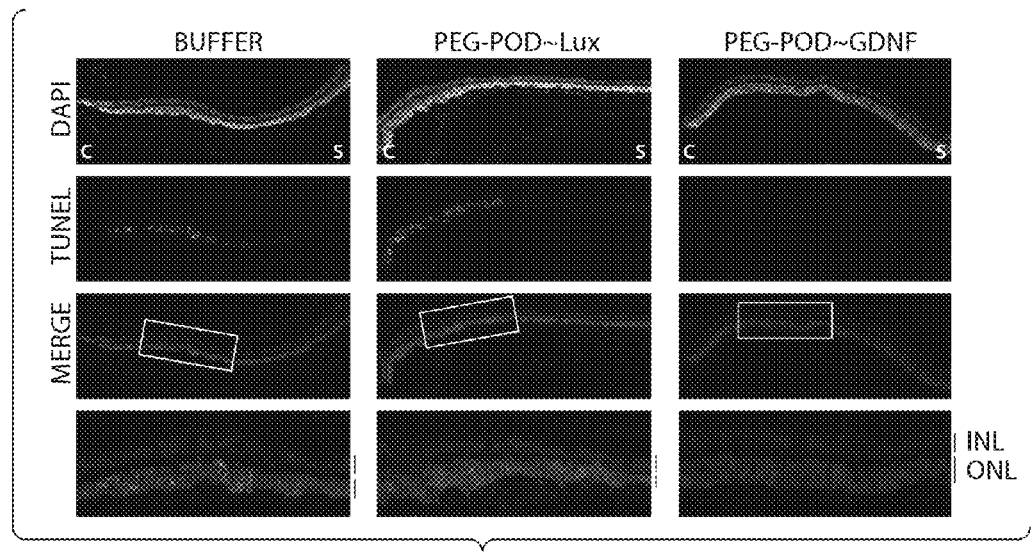
FIG. 24 is a set of photomicrographs and bar graphs showing that injecting PEG-POD~GDNF nanoparticles resulted in decreased apoptosis of photoreceptors.
Figure 24B:
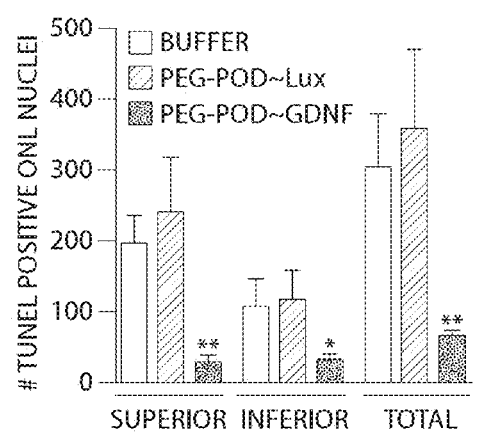
Figure 24C:
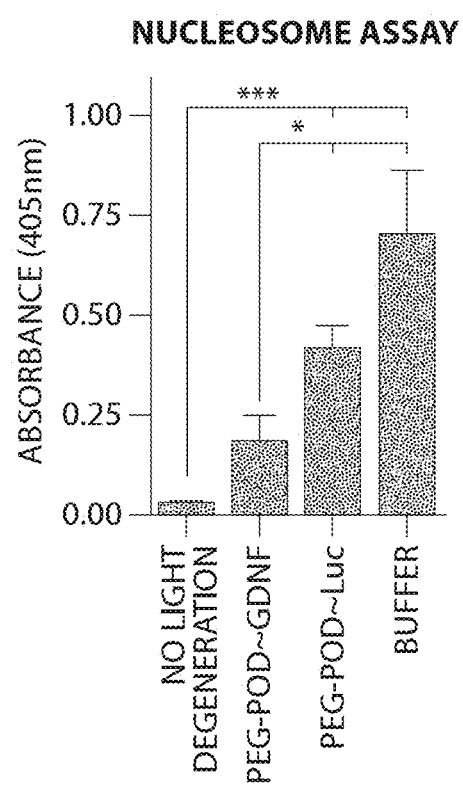

Activation of caspase-3 is an important mediator of apoptosis in inherited [Liu C, et al. 1999 J Neurosci. 19(12): 4778-4785; Yoshizawa K, et al. 2002 Graefes Arch Clin Exp Opthalmol. 240(3): 214-219] and acute [Chang C J, et al. 2005 Ophthalmic Res, 37(4): 202-213; Perche O, et al. 2007 Invest Ophthalmol Vis Sci. 48(6): 2753-2739] or blue light induced retinal degeneration [Wu J, et al. 2002 Invest Opthalmol Vis Sci. 43(10): 3349-3354]. Examples herein show that induction of caspase-3 activity in photoreceptors following acute exposure to bright blue light (FIG. 23 panel A). Rat RPE undergoes histological apoptosis in response to bright light at a later time point compared to that of photoreceptors [Hafezi F, et al. 1997 Exp Eye Res. 64(6): 963-970], and with transient morphological changes [Gorgels T O, et al. 1995 Invest Opthalmol Vis Sci. 36(5): 851-863]. RPE cells exposed to the lipofuscin fluorophore A2E were shown to initiate apoptosis in vitro after exposure to blue light in a caspase-3 dependent manner [Sparrow J R, et al. 2000 Invest Opthalmol Vis Sci. 41(7): 1981-1989; Sparrow J R, et al. 2001 Invest Opthalmol Vis Sci. 42(6): 1356-1362]. Examples herein show increased caspase-3 activity in the RPE/choroid/sclera after 24-hours, with no TUNEL staining observed in these tissues at the 48-hour time point (FIG. 23 panel A and FIG. 24 panel A).

The Chesapeake Bay Waterman Study reported a correlation between patients with the most advanced AMD and a high incidence of exposure to blue or white light [Taylor H R, et al. 1992 Arch Opthalmol. 110(1): 99-104], with blue light considered as a possible contributing factor in pathogenesis of AMD [Wu J, et al. 2006 Surv Opthalmol. 51(5): 461-481]. Examples herein investigate the link between caspase-3 and inherited models of retinal degeneration, and show that exposure to bright blue light is a viable model in which to test the efficacy of PEG-POD~GDNF nanoparticles to rescue photoreceptor degeneration.

Figure 30A:
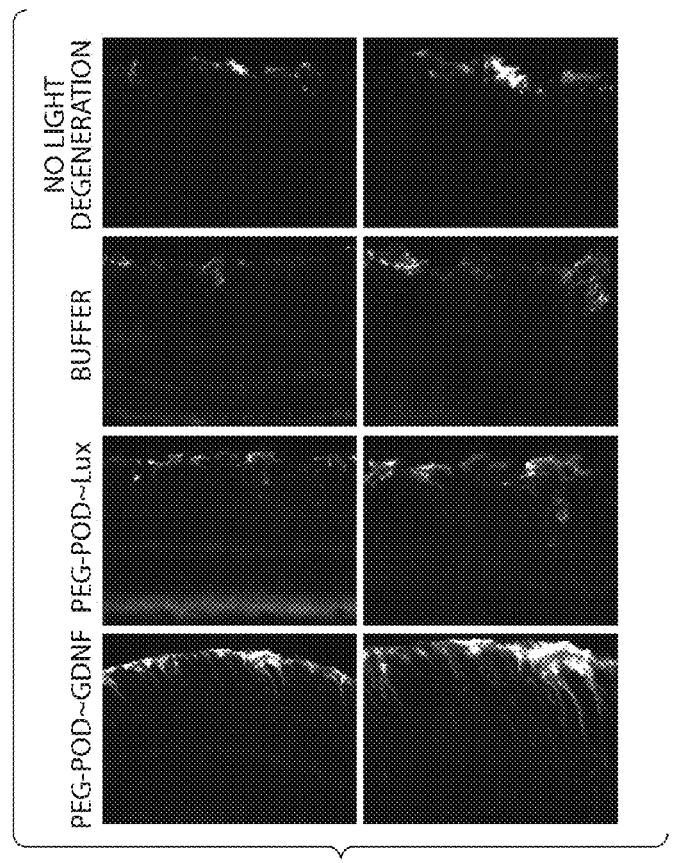
FIG. 30 is a set of photomicrographs and a bar graph showing that injection of PEG-POD~GDNF nanoparticles causes Müller cell activation. Eyes exposed to light, and were injected with POD~GDNF (fourth row), PEG-POD~Lux (third row) or buffer. Eyes and control eyes not exposed to light were harvested 48 hours post-injection, and were sectioned and stained for glial fibrillary acidic protein, GFAP, in the Müller cell body of the inner retina. The GFAP staining was visualized (FIG. 30 panel A) and was quantified (FIG. 30 panel B).
Figure 30B:
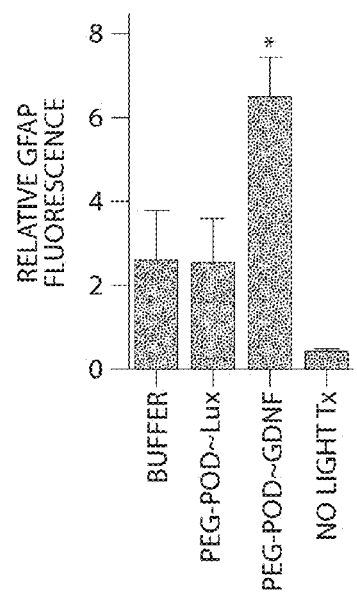

GDNF mediates neuroprotection by both a direct mechanism through photoreceptor signaling and an indirect mechanism of signaling through Müller cells. Support for the direct pathway has come from detecting expression of GDNF receptors, and not other neurotrophic receptors like CNTF, in photoreceptors [Harada T, et al. 2002 J. Neurosci. 22(21): 9228-9236]. Upregulation of the receptor coincided with increased exogenous GDNF expression [Harada C, et al. 2003 Neuroscience. 122(1): 229-235]. An indirect pathway acting through Müller cells has been observed. Müller cells, treated with GDNF, increased expression of BDNF, bFGF and GDNF [Harada T, et al. 2002 J. Neurosci. 22(21): 9228-9236], or bFGF alone [Hauck S M, et al. 2006 Mol Cell Biol. 26(7): 2746-2757]. GDNF receptors on the Müller cells have a subunit in response to light damage. Injection of GDNF protein into mouse retina activated Müller glia [Wenzel A, et al. 2005 Prog Retin Eye Res. 24(2): 275-306]. Examples herein show that injection of retinas with PEG-POD~GDNF nanoparticles caused significantly increased and re-distributed GFAP expression relative to retinas injected with either control nanoparticles or with control buffer, and that indicates Müller cells are activated (FIG. 30 panel B).

GDNF has been shown to rescue the inherited rd/rd (rd1) mouse model of RP [13], the rhodopsin mutant S334ter rat model [McGee Sanftner L H, et al. 2001 Mol. Ther. 4(6): 622-629], the RCS rat model [Lawrence J M, et al. 2004 Invest Opthalmol Vis Sci. 45(1): 267-274], damage induced by retinal detachment [Wu W C, et al. 2002 Invest Opthalmol Vis Sci. 43(11): 3480-3488], and ischemia-reperfusion injury [Wu W C, et al. 2004 Mol. Vis. 10: 93-102]. Numerous models including the RCS rat model, the S344ter RP animal model and the P23H model demonstrate increased susceptibility to light damage [Wu J, et al. 2006 Surv Opthalmol. 51(5): 461-481], a phenomenon also documented in human RP patients [Heckenlively J R, et al. 1991 Arch Opthalmol. 109(1): 84-91; Paskowitz D M, et al. 2006 Br Opthalmol. 90(8): 1060-1066]. Caspase-3 activity [Wu J, et al. 2006 Surv Opthalmol. 51(5): 461-481] is upregulated in S334ter rat model and GDNF anti-apoptotic activity prevents the caspase-3 initiated cell death cascade.

GDNF delivered via adeno-associated virus (AAV) does not rescue retinal degeneration in mice as measured by ERG or histology when assessed one week after constant 96-hour white light exposure [Allocca M, et al. 2007 Invest Opthalmol Vis Sci. 48(11): 5199-5206]. In Examples herein, prolonged low white light as opposed to acute blue light was employed. Blue light causes cell death via a different apoptotic pathway [Wu J, et al. 2006 Sury Ophthalmol. 51(5): 461-481].

Figure 25A:
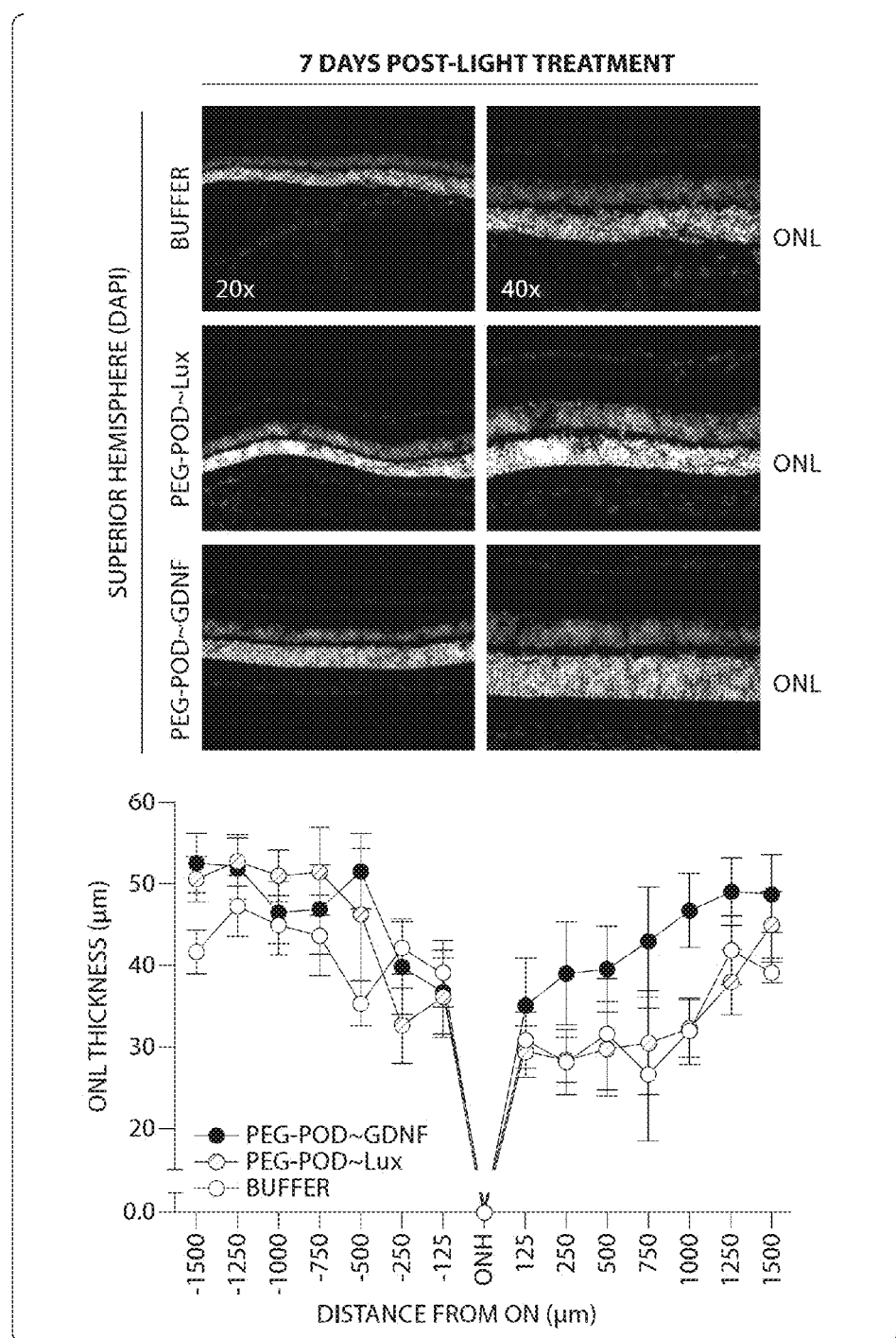
FIG. 25 is a set of photomicrographs and line graphs showing that injection of PEG-POD~GDNF decreases photoreceptor cell loss in eyes 7 days and 14 days post light exposure, respectively. To examine the effect on photoreceptor cell loss, ONL thickness was visualized and measured for retinas injected with each of PEG-POD~GDNF, PEG-POD~Lux, and buffer. The injected retinas were then exposed to light and were harvested 7 days or 14 days after light exposure. ONL average thickness and INL average thickness were measured at distances extending from the optic nerve.
Figure 25B:
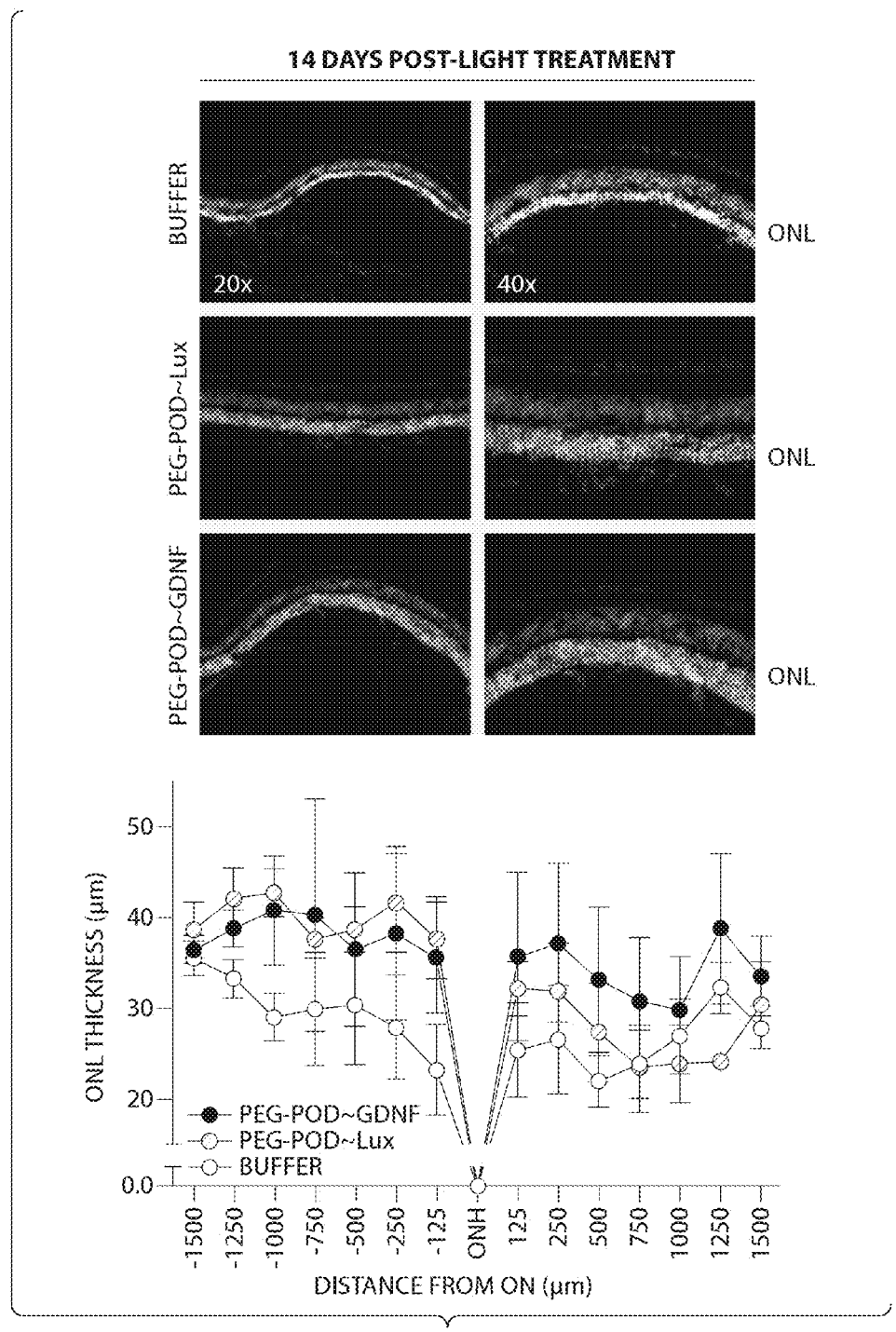

To test the anti-apoptotic activity of PEG-POD~GDNF nanoparticles, retinal sections were examined by TUNEL stain 48 hours post-light treatment. Blue light exposure preferentially damages the superior hemisphere of the eye [Wu J, et al. 2002 Invest Opthalmol Vis Sci. 43(10): 3349-3354; Wu J, et al. 1999 Graefes Arch Clin Exp Opthalmol. 237(10): 855-860], which was also observed in Examples herein (FIG. 25 panel A). Injection of PEG-POD~GDNF nanoparticles caused significant decreased number of TUNEL positive photoreceptor nuclei in both the superior and inferior hemispheres of the eye (FIG. 24 panel B). A significant decrease in nucleosome release was also observed in lysates of whole retinas injected with PEG-POD~GDNF particles compared to retinas injected with a control (FIG. 24 panel C).

A decreased level of photoreceptor apoptosis in PEG-POD~GDNF injected eyes was observed by TUNEL staining. Increased thickness of the ONL was observed at 7 days post-injection (FIG. 25 panel A) compared to PEG-POD~Lux- and buffer injected retinas. At 14 days post-injection, the PEG-POD~GDNF-injected eyes were observed to have increased ONL thickness only in superior retina. Small or no differences were observed at 14 days post-injection in ONL thickness of the inferior retina of eyes injected with PEG-POD~GDNF nanoparticles and PEG-POD~Lux nanoparticles. An increase in ONL thickness was observed following these nanoparticle-injection treatments, conditions compared to thickness observed with eyes injected with buffer only (p<0.005) (FIG. 25 panel B).

Differences between dextrose and nanoparticle-injected eyes after 14 days post-treatment were observed herein, demonstrating that the POD peptide component of the nanoparticle, or the nanoparticle itself, conferred therapeutic effects. The potential therapeutic effect of the POD peptide component was observed with eyes treated with PEG-POD~Lux or with dextrose, demonstrated by decreased nucleosome release two days after light treatment (FIG. 25 panel C). Without being limited by any particular theory or mechanism of action, it is here envisioned that PEG-POD complexed DNA has a therapeutic effect and increases or prolongs detachment, or growth factor release following the initial injection. Delivery of a nanoparticle containing the therapeutic GDNF transgene significantly altered the course of degeneration beyond effects observed herein for the vector or injection only control treatments. For example, retinal detachment or injury has been shown to rescue both light induced (FIG. 23 panels B and C) [Faktorovich E G, et al. 1992 J. Neurosci. 12(9): 3554-3567] and inherited models of retinal degeneration [Wen R, et al. 1995 J. Neurosci. 15(11): 7377-7385]. Rescue could be mediated both by injury-induced upregulation of various growth factors [Wen R, et al. 1995 J. Neurosci. 15(11): 7377-7385], or by down regulation of members of the phototransduction cascade that play a role in mediating light damage [Rattner A, et al. 2008 J. Neurosci. 28(39): 9880-9889].

Figure 28A:
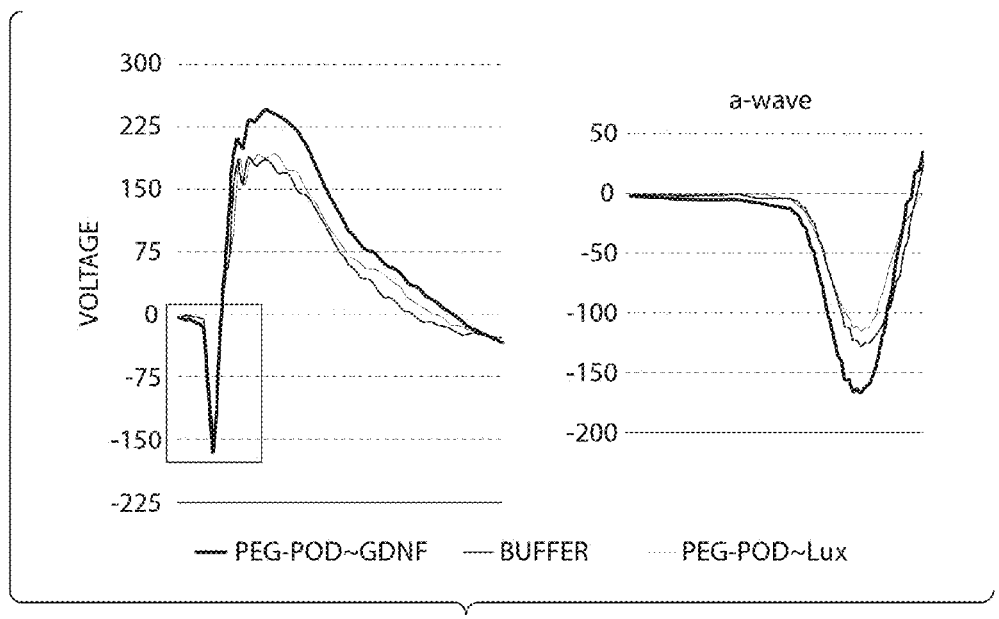
FIG. 28 is a set of electroretinogram readouts and bar graphs showing functional rescue by injection of PEG-POD~GDNF of light-damaged retina. To evaluate the functional rescue of PEG-POD~GDNF-injected retinas, electroretinograms were obtained seven days post-light exposure.
Figure 28B:
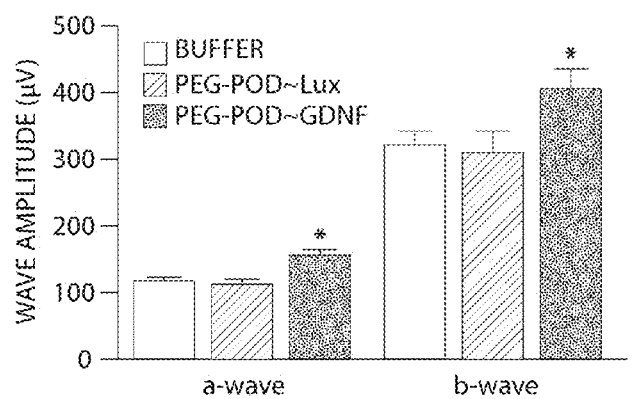
Figure 29:
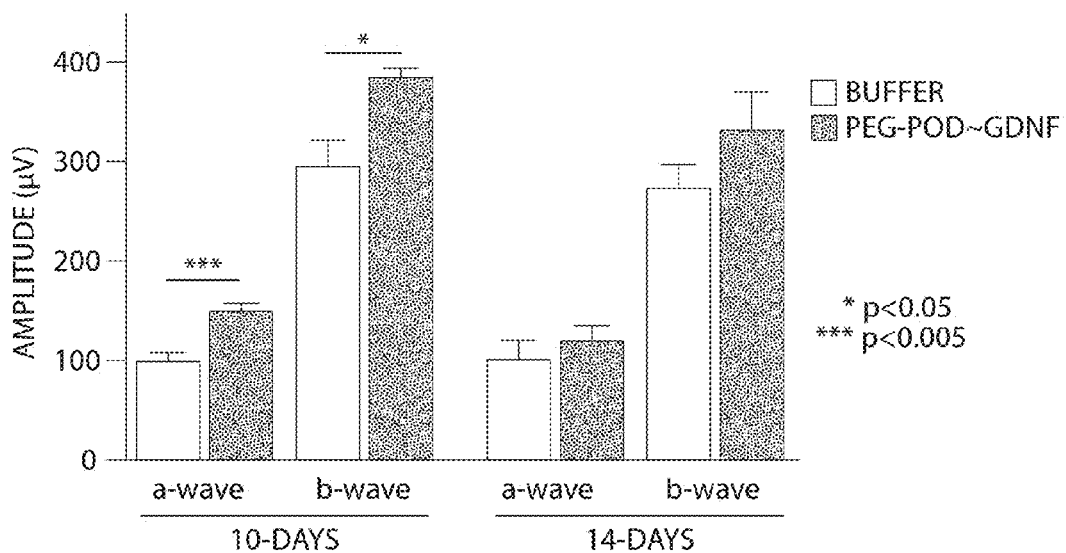
FIG. 29 is a bar graph showing functional rescue 10 days and 14 days after subretinal injection of PEG-POD~GDNF. The bar graphs show ERG amplitudes (μV) for a-waves and b-waves of eyes injected with either PEG-POD~GDNF or buffer 10 days and 14-days post light exposure. Data in FIG. 28 above shows amplitude data for eyes injected with PEG-POD~GDNF or buffer 7 days after light exposure. ERG amplitudes of eyes injected with PEG-POD~GDNF 10 days post-light treatment were significantly higher than eyes injected with buffer for both for a-waves (p<0.005) and b-waves (p<0.05). PEG-POD~GDNF, n=7; Buffer, n=10. Mean±SEM. The functional response of PEG-POD~GDNF-injected eyes was not significantly higher 14 days post-light treatment, than of eyes injected with buffer (p>0.05). PEG-POD~GDNF, n=4; Buffer, n=6. Mean±SEM.

Injection of PEG-POD~GDNF into eyes was shown to reduce loss of photoreceptors and to increase retinal function as measured by scotopic ERG (FIG. 28 panels A and B). ERG measurement of these PEG-POD~GDNF injected eyes 7 days post-light treatment showed 32-39% increased a-wave and 27-31% increased b-wave amplitudes compared to control eyes that were treated by other injection conditions. Also observed was an increased level of rescue 10 days after light exposure (49% and 29% for the a-wave amplitude and b-wave amplitude, respectively) for PEG-POD~GDNF injected eyes compared to buffer injected eyes. No significant difference was observed between the two conditions 14 days after light treatment (FIG. 29), nor in the histological data. Plasmid modifications affect efficiency and time course of transfection [Argyros O, et al. 2008 Gene Ther. 15(24): 1593-1605; Yurek D M, et al. 2009 Mol. Ther. 17(4): 641-650; Harraghy N, et al. 2008 Curr Gene Ther. 8(5): 353-366; Koirala A, et al. May 27-30, 2009 Amer Society of Gene Ther. Abstract 129].

Although there have been advances in the field of non-viral ocular gene therapy [Bloquel C, et al. 2006 Adv Drug Deliv Rev. 58(11): 1224-1242], successful translation of techniques and methods to the clinic have been hampered by low transfection efficiency, with few vectors demonstrating in vivo rescue in animal models. Those few reports of rescue of models of retinal degeneration have employed either the use of positively charged peptides to create electrostatically charged peptide/DNA complexes [Cai X, et al. 2009 PLoS One. 4(4): e5290; Neuner-Jehle M, et al. 2000 Hum Gene Ther 11(13): 1875-1890] or mechanical disruption by iontophoresis or electroporation [Cai X, et al. 2009 PLoS One. 4(4): e5290; Souied E H, et al. 2008 Exp Eye Res. 87(3): 168-175; Neuner-Jehle M, et al. 2000 Hum Gene Ther 11(13): 1875-1890; Zhang M, et al. 2009 Curr Eye Res. 34(9): 791-799]. Subretinal injection of DNA compacted with each of peptides K8 and JTS-1 (K8/JTS-1), transfected RPE and choroidal cells using a RCS rat model. These injections showed delayed retinal degeneration relative to control injections in the retinal area [Neuner-Jehle M, et al. 2000 Hum Gene Ther 11(13): 1875-1890]. However the ONL thickness and function of these retinas was not determined, making it difficult or impossible to directly compare those results with data herein.

The PEGylated poly-lysine peptide PEG-CK30 has been used to deliver the peripherin/rds transgene into the subretinal space of heterozygous rds mutant (rds$^{+/-}$) mice having developing (post-natal day 5, P5) and post-mitotic (P22) retina [Cai X, et al. 2009 PLoS One. 4(4): e5290; Cai X, et al. 2009 Faseb J]. PEG-CK30 transfection led to a 2-4-fold increase in peripherin/rds, detectable up to 120 days post-injection.

Transscleral iontophoresis of β-PDE cDNA in a rd1 mouse model increased the thickness of peripheral retina and detectable ERG recordings at P23 [Souied E H, et al. 2008 Exp Eye Res. 87(3): 168-175]. However, iontophoresis (and therefore gene delivery) was performed at P8, prior to completion of retinal development. It is unclear from these studies whether iontophoresis gene delivery to retinal tissue rescues disease after retinal development. Electroporation in an adult RCS rat model was found to deliver DNA to the RPE and retinal ganglion cells [Zhang M, et al. 2009 Curr Eye Res. 34(9): 791-799]. Delivery of a BDNF transgene by this method decreased TUNEL positive photoreceptor nuclei and increased photoreceptor survival [Zhang M, et al. 2009 Curr Eye Res. 34(9): 791-799], however functional rescue was not determined. Electroporation using similar voltage levels in mice causes high toxicity and substantial decrease in ERG amplitudes [Kachi S, et al. 2005 Gene Ther. 12(10): 843-851].

Examples herein show that PEG-POD is a therapeutically relevant non-viral DNA delivery vehicle that functionally rescues in an adult model of retinal degeneration. It is envisioned that PEG-POD~GDNF nanoparticles have therapeutic implications across a wide spectrum of retinal dystrophies, including the common apoptotic pathways not limited to the light induced degeneration model used in this study, and in inherited models of retinal degeneration.

Additional embodiments and examples of the invention are found in the claims below, which are illustrative and are not to be construed as further limiting. The contents of all literature cited herein are hereby incorporated in their entirety by reference.

A portion of this work was presented as: "Cell penetrating peptide POD mediates delivery of recombinant proteins to retina, cornea and skin" by Leslie N. Johnson, Siobhan M. Cashman, Sarah Parker Read and Rajendra. Kumar-Singh, Vision Research published online Sep. 3, 2009; "Cell-penetrating peptide for enhanced delivery of nucleic acids and drugs to ocular tissues including retina and cornea" by Leslie N. Johnson, Siobhan M. Cashman and Rajendra Kumar-Singh, Molecular Therapy 16(1): 107-14, Oct. 9, 2007; "A poly(ethylene) glycolylated peptide for ocular delivery compacts DNA into nanoparticles for gene delivery to post-mitotic tissues in vivo" by Sarah Parker Read, Siobhan M. Cashman and Rajendra Kumar-Singh, The Journal of Gene Medicine 12: 86-96, Nov. 24, 2009, and "POD Nanoparticles Expressing GDNF Provide Structural and Functional Rescue of Light-Induced Retinal Degeneration in an Adult Mouse" by Sarah Parker Read, Siobhan M. Cashman, Rajendra Kumar-Singh; submitted to the journal Molecular Therapy, which are hereby incorporated by reference herein in their entireties.

EXAMPLES

The following materials and reagents were used throughout the examples herein.

Materials and Reagents.

Heparan sulfate, chondroitin sulfate, Propidium iodide were purchased from Sigma. GFP Duplex I was purchased from Dharmacon (Lafayette, Colo.) and pd2-EGFPNI was from Clontech (Mountain View, Calif.). N terminal conjugated peptides (lissamine, biotin, cysteine) with GGG(ARKKAAKA)$_4$ (SEQ ID NO: 1) were custom synthesized and HPLC purified by Sigma Genosys (Woodlands, Tex.). N terminal FITC conjugated GGG(ARKKAAKA)$_4$ (SEQ ID NO: 1) was synthesized by the University of Utah peptide facility. All other commercially available materials and reagents, including the Qdot$_{655}$ Streptavidin conjugate, were purchased from Invitrogen (Carlsbad, Calif. unless otherwise noted.

Cell Penetrating Properties of POD

HER cells were seeded on Lab Tek-II chamber slides and grown to about 70% confluence. Cells were washed twice with PBS and incubated with 1 mole L-POD for 0, 5, 15, 30, 45, and 60 minutes or 1 nmol Lissamine only for 60 minutes. Cells were fixed for 15 minutes in formalin at room temperature. Cells for live imaging were grown on 24 well plates and incubated with 2 mmoles of L-POD. Following incubation, cells were washed three times with PBS, incubated in phenol red-free DMEM supplemented with 2% FBS. Cells were visualized by light and fluorescent microscopy using either an Olympus IX51 (live cells) or an Olympus BX51 (fixed cells) with DIC, RFP, and GFP filters. Images were obtained using a Retiga 2000R FAST camera and QCapture Pro 5.0 (QImaging, BC, Canada). To measure L-POD uptake in the presence of trypsin, 0.2×10$^6$ HER cells were incubated with 2.0 nmole L-POD in media for 15 minutes at 37° C. followed by incubation in 2.5 mg/ml trypsin for 12 minutes at 37° C. For analysis of uptake at 4° C., cells were cooled to 4° C. for 45 minutes prior to the addition of peptide and cold (4° C.) reagents were used for peptide administration. Following incubation with peptide, cells were washed twice with PBS and spun and resuspended in PBS for FACS analysis. For measurement of membrane permeabilization, HER cells were incubated with 2.0 nmole FITC-HBP for 30 minutes at 37° C., washed twice, isolated, and suspended in PBS with 1 µM PI. The number of PI-positive cells was analyzed by FACS. FACS analysis was performed using a FACSCalibur (Becton Dickinson). Examples were performed in triplicate and 10,000 events per sample were counted. Results were analyzed using CellQuest Pro software (Becton Dickinson).

POD Mediated Delivery of siRNA, DNA and Quantum Dots In Vitro pCAGRFP was compacted with C-POD at a ratio of 400 peptide/plasmid molecules. Briefly, 2 µg of DNA and the appropriate concentration of peptide were each suspended in 15 µL of either 100 µM sodium phosphate or 5% dextrose buffer. The peptide and DNA solutions were mixed and incubated for 30 minutes at room temperature prior to addition to HER cells. After 48 hours, cells were resuspended in PBS for FACS analysis. For electron microscopy, peptide/DNA complexes were prepared as above. Particles were bound to glow-discharged copper grids, stained with urinyl acetate, and visualized on a CMIO Transmission Electron Microscope (Philips) using Digital Micrograph software (Gatan, Inc). C-POD was used to compact both pd2-EGFP-NI and GFP Duplex I at concentrations of 450 particles/DNA molecule and 25 particles/duplex molecule, respectively, in 100 mM sodium phosphate buffer using the same procedures described above. Compacted pd2-EGFP-NI DNA, 2 µg, and 70 pmoles of GFP Duplex I diluted in DMEM+2% FBS were added simultaneously to HER cells for 4 hours. Growing medium was then added to cells and the incubation continued for 44 additional hours. Cells were isolated and resuspended in PBS for FACS analysis as described above. For delivery of quantum dots, 50 pmoles of a Qdot655 streptavidin conjugate (Invitrogen, Carlsbad, Calif.) were added to 5 nmoles of Biotin-conjugated POD (B-POD) in PBS and mixed for 1 hour by gentle rocking at room temperature. The Qdot-peptide complex (QDPOD) was dialyzed in PBS using a 50 K Ultrafree (Millipore) column and added to $0.2 \times 10^6$ HER cells for either 15 minutes or two hours. The amount of fluorescence resulting from the Qdot-peptide complex was determined using a fluorometer and an equivalent amount of unbound Strep-Qdot was added separately as control. Cells were washed three times with PBS, fixed as described above, and stained with DAPI. Uptake of Qdots was determined by fluorescent microscopy as described above.

Inhibition of POD Uptake by Proteoglycans and POD-Associated Microbicidal Activity Lissamine conjugated POD (L-POD) and either heparan sulfate or chondroitin sulfate were incubated together at each of molar ratios of 1:3.33, 1:6.67, and 1:8 in water for 30 minutes at room temperature. The complex was diluted in DMEM+2% FBS and added to $0.2 \times 10^6$ HER cells for 5 minutes at 37° C. Following incubation, cells were trypsinized and suspended in PBS for FACS analysis as described above. To measure microbicidal activity of C-POD, XL-1 Blue cells (Stratagene, La Jolla, Calif.) were grown to mid logarithmic phase (OD600=0.600) and washed twice in a solution of 10 mM Tris, pH 7.4 and 5 mM Glucose. The cells were resuspended in 10 mL of the same solution and 5 mL of the suspension was incubated with C-POD in a final volume of 50 µL. The peptide/bacteria cell solution was rocked for 2 hours at 37° C. The peptide-treated bacteria was diluted 1:4500 with LB broth, plated on agar, and grown overnight at 37° C. The following day, the bacterial colonies on each plate were counted to quantify peptide-related reduction in growth.

POD-Mediated Delivery of Molecules to Ocular Tissues In Vivo

The use of animals in this work was in accordance with the ARVO Statement for the Use of Animals in Ophthalmic and Vision Research. C57BL/6J mice were purchased from Jackson Laboratories, bred and maintained in a 12-hour light-dark cycle and cared for in accordance with federal, state and local regulations. For each Example herein at least 4 mice (8 eyes) were investigated, yielding roughly similar results. Mice were anesthetized by intravitreal injection of xylazine (10 mg/ml)/ketamine (1 mg/ml). Subretinal or intravitreal injections were performed with a 32 G needle attached to a 5 µl glass syringe (Hamilton) by a trans scleral trans choroidal approach to deliver 0.25 nmole of L-POD per eye. For topical delivery to cornea, male C57BL6/6J mice at 6 weeks of age were anesthetized by intraperitoneal injection of ketamine/xylazine and 10 nmoles of either L-POD or lissamine only were dropped on the cornea and incubated for 45 minutes or 24 hours. Upon completion of the treatment, the animal was sacrificed by $CO_2$ inhalation followed by cervical dislocation and the eyes harvested and washed three times in PBS. Fluorescent and bright field images were taken of each eye using a Nikon C-FMC microscope prior to fixation. Eyes were fixed overnight at 4° C. in 4% paraformaldehyde and embedded in Optimal Cutting Temperature Compound and 14 µm sections were collected using a Microm 550 cryostat.

Adenovirus Constructs and Glycosaminoglycan Blocking

Constructs Ad5pIXPODs and Ad5pIXPODsΔRGD were generated in two steps by modification of pShuttle [He et al. (1998) Proc Natl Acad Sci USA 95: 2509-2514] such that the stop codon was replaced by synthetic oligonucleotides: 5'CGCCAAGCTTGCTCGTAAGAAGGCT-GCTAAGGCTGCCCGCAAGAAGGCCGCCAA GGCCG-CACGAAAGAAGGCAGCGAAGGCGTGAGC 3'(SEQ ID NO:9), and 5'GGCCGCTCACGCCTTCGCTGCCT-TCTTTCGTGCGGCCTTGGCGGCCTTCTTGCGG GCAGCCTTAGCAGCCTTCTTACGAGCAAGCTT GG 3', (SEQ ID NO:10), resulting in a pIX-PODs fusion. These recombinant shuttle plasmids were recombined with either pAdEasy-1 [He et al. 1998 Proc Natl Acad Sci USA 95: 2509-2514] or with pAdEasy-1 containing a deletion in the RGD domain of penton base. The resultant viruses were purified using the Adenopure kit (Puresyn, Inc, Malvern, Pa.). To measure the effect of proteoglycans on the above viruses, they were incubated with either heparan sulphate or chondroitin sulphate prior to addition to Chang C or 911 cells. A total of each of $1 \times 10^8$ particles of AdCAGGFP, Ad5pIXPODs or Ad5pIXPODsΔRGD were incubated with 16 nmoles of either heparan sulphate or chondroitin sulphate at room temperature for 30 minutes. The virus-peptide mixture was added to cells in medium at a final multiplicity of infection of (moi) 500. Forty-eight hours following infection, cells were isolated and resuspended in PBS for FACS analysis.

Cell Culture and Transfection

Human embryonic retinoblast (HER) cells were cultured using previously described methods [Fallaux F J et al. 1996 Hum. Gene Ther. 7: 215-222]. Carcinoma human alveolar basal epithelial cells (A549, American Type Culture Collection, Manassas, Va.) were grown to 70-80% confluence in DMEM media supplemented with 10% fetal bovine serum (FBS). All cell culture procedures were performed in DMEM supplemented with 2% FBS. Transfection of plasmids was carried out using 2:1 µL Lipofectamine: µg plasmid in Opti-MEM media. Forty-eight hours post-transfection, the cells were fixed and stained with DAPI, 4',6-diamidino-2-phenylindole.

Plasmid and Adenovirus Construction

Oligonucleotides POD-upper and POD-lower coding for the POD protein transduction domain were cloned into SacI/EcoRI digested pQBI25fA1 (Qbiogene, Carlsbad, Calif.) to generate pPODGFP. pPODGFPHis and pGFPHis were cloned by inserting the oligonucleotides His-upper and His-lower into ClaI/MluI digested pPODGFP and pQBI25fA1, respectively as shown herein. pPODGFPHis and pGFPHis were digested with BglII and XmnI and ligated with BglII/EcoRV-digested pShuttle. The corresponding pShuttle plasmids were linearized with PmeI, gel purified, and cotransfected with pAdEasy-1 into *E. coli* BJ5183 cells. Recombinant plasmids were digested with PacI and transfected into HER cells. AdPODGFPHis and AdGFPHis were isolated using a virus purification kit (Puresyn, Malvern, Pa.).

```
POD-upper:
                                            (SEQ ID NO: 5)
GCCACCATGGCTCGTAAGAAGGCTGCTAAGGCTGCCCGCAAGAAGGCT
GCCAAGGCCGCACGAAAGAAGGCAGCAAAGGCGGCTCGTAAGAAGGCT
GCCAAGGCGTC POD-lower:
                                            (SEQ ID NO: 6)
AATTGACGCCTTGGCAGCCTTCTTACGAGCCGCCTTTGCTGCCTTCTT
TCGTGCGGCCTTGGCAGCCTTCTTGCGGGCAGCCTTAGCAGCCTTCTT
ACGAGCCATGGTGGCGC His tag-upper:
                                            (SEQ ID NO: 7)
CGATCATCATCACCATCACCATTGA His tag-lower:
                                            (SEQ ID NO: 8)
CGCGTCAATGGTGATGGTGATGATGAT
```

The sequences indicated as underlined are POD and His tag specifically.

Protein Isolation and Purification

HER cells were infected with either AdPODGFPHis or AdGFPHis at a multiplicity of infection (moi) of 200 viral particles/cell. Cells were harvested when greater than 90% of cells were GFP-positive as determined by fluorescence microscopy which occurred approximately 96 hours post-infection. The cytoplasm and nucleus were isolated and lysed for protein purification using the NuCLEAR Extraction Kit (Sigma, St. Louis, Mo.). Fusion proteins were isolated using the His-Select kit (Sigma) and 250 mM imidazole according to manufacturer's instructions. The final protein eluates were dialyzed in PBS using a 10K Ultrafree column (Millipore, Billerica, Mass.). Protein concentrations were measured using a Bradford assay (Bio-Rad, Hercules, Calif.). To eliminate the potential of virus contamination in the protein prep, fusion proteins were heated to 70° C. for five minutes to inactivate any residual virus, and were tested for cytopathic effect in HER cells.

Cellular Uptake and Localization of PODGFPHis

To evaluate cellular penetration of POD fusion proteins, HER cells were seeded on Lab Tek-II chamber slides and incubated with 10 µg of POD-GFP or GFP for two hours. Following fixation, cells were visualized by light and fluorescence microscopy using an Olympus BX51 microscope with differential interference contrast (DIC) and the appropriate fluorescence filters. Images were captured using a Retiga 2000R FAST camera and QCapture Pro 5.0 (QImaging, British Columbia, Canada). To quantitate protein uptake, $0.2 \times 10^6$ of either HER or A549 cells were incubated with 10 µg POD-GFP or GFP for 2 hours. Cells were washed with PBS, pelleted and resuspended in PBS for FACS analysis. Cell membrane integrity was evaluated by measuring the percentage of Propidium Iodide (1 µM) positive cells in the presence of fusion protein. FACS analysis of protein uptake and toxicity was performed using a FACSCAlibur (Becton Dickinson, Franklin. Lakes, N.J.) and results analyzed using CellQuest Pro (Becton Dickinson). 10,000 events were counted for each analysis, which was performed in triplicate and repeated at least once.

HER and A549 cells were treated as above for subsequent addition of LysoTracker, ER Tracker (Molecular Probes, Carlsbad, Calif.), or DAPI, and were incubated for one hour. These reagents were removed and cells were fixed with formalin for imaging.

Silver Staining and Western Blotting

For protein analysis 1 µg of POD-GFP and 250 ng of recombinant GFP were loaded onto a 12% Tris-HCl gel (Bio-Rad). Silver staining was carried out using Silver Stain Plus Kit (BioRad, Hercules, Calif.). For Western blotting, proteins were transferred to PVDF membranes, which were probed for GFP expression using anti-AFP 5001 11E5 monoclonal antibody (MP Biomedicals, Solon, Ohio) and HRP-conjugated goat anti-mouse secondary antibody. The signal was detected using SuperSignal West Pico chemiluminescent substrate (Pierce, Rockford, Ill.).

Transdermal Application

Adult mice were anesthetized as described above and the abdomen shaved to reveal a 2.25 cm² area of skin. A dose of 40 µg of protein was applied to the skin for 24 hours. Upon completion of the treatment, animals were sacrificed and the treated skin dissected and fixed overnight in 4% paraformaldehyde and transverse sections were obtained as described herein.

Plasmids, Peptide and Cell Lines pCAGLuc was cloned by placing the Luciferase cDNA from pGL3-Control (Promega) into pBluescript II KS (Stratagene) using HindIII and XbaI. An XhoI/NotI fragment of this plasmid was inserted into pCAGEN (kindly provided by C. Cepko).

A SmaI/NotI fragment of pCMVb (Ciontech) was cloned into EcoRV/NotI-digested pCAGEN to generate pCAGLacZ. Plasmid pCAGGFP was generously provided by C. Cepko. C-POD, CGGG(ARKKAAKA)$_4$ (SEQ ID NO: 11) was generated at Tufts University Peptide Synthesis Core Facility and purified by HPLC. Both lung epithelial A549 cells (ATCC) and human embryonic retinoblasts (HER; Fallaux et al 1996) were grown in Dulbecco's modified Eagle's media (DMEM) supplemented with 10% fetal bovine serum (FBS; Invitrogen).

Delivery of POD-GEPHis and of POD/DNA Complexes In Vivo

The use of animals in this study was in accordance with the Association for Research in Vision and Opthalmology (ARVO) Statement for the Use of Animals in Opthalmic and Vision Research.

Subretinal and intravitreal injections of the fusion proteins were performed using techniques described in Cashman et al. [2006 Invest Opthalmol Vis Sci 47:3496-3504]. Briefly, 8.5 µg of POD-GFP or 6.6 µg of GFP protein was injected into the subretinal or intravitreal space respectively, of 6-8 week old C57BL/6J mice. Four independent injections were performed and yielded nearly identical results. Six hours post-injection, mice were sacrificed by CO$_2$ inhalation and cervical dislocation. For topical delivery of the POD-GFPHis or GFP-His, C57BL/6J mice were anesthetized with xylazine/ketamine and 2 µl containing 40 µg of protein were dropped onto the conical surface. Forty-five minutes following administration, mice were sacrificed as above and eyes enucleated, washed twice in PBS, and fixed overnight in 4% paraformaldehyde. Eyes were embedded in Optimal Cutting Temperature Compound (Sakura Finetek, Torrance, Calif.) and 14 µm sections were collected using a Microm 550 cryostat.

C57BL/6J and BALB/CJ mice were purchased from Jackson Laboratories and maintained in 12-hour dark light cycles in accordance with federal, state, and local regulations. Mice were anesthetized by intraperitoneal injection of xylazine (10 mg/ml)/ketamine (1 mg/ml). Subretinal injections were performed with a 32 G needle (Becton Dickinson) and a 5 μl glass syringe (Hamilton) by a trans-scleral trans-choroidal approach. Animals were sacrificed by $CO_2$ inhalation followed by cervical dislocation.

C-POD/DNA Compaction: In Vitro and In Vivo Delivery pCAGGFP or pCAGLuc were compacted using C-POD as previously described [Johnson L et al. 2007 Mol Therapy 16: 107-114]. Briefly, 1.8 nMoles of C-POD were used to compact 2 μg of DNA (Nitrogen:Phosphate (NIP) ratio of 8.6) in sodium phosphate (100 mmol/l) and added to the media of 2×10⁵ A549 cells. In serum starvation conditions the cells were incubated with serum free DMEM for 24 hours prior to transfection. After 48 hours, cells were resuspended in phosphate buffered saline (PBS) for FACS analysis of GFP or prepared for luciferase assay according to the manufacturer's protocol (Promega). Live cells were visualized with light and fluorescent microscopy using an Olympus IX51 with differential interference contrast and appropriate fluorescent filters. Images were captured using a Retiga 2000R FAST camera and QCapture Pro 5.0 (QImaging, British Columbia, Canada). FACS analysis was performed using a FACSCalibur (Becton Dickinson) and analyzed using CellQuest Pro software (Becton Dickinson). Analysis was done in triplicate and 15,000 events were recorded per sample. For use in explants and in vivo injection, C-POD/DNA complexes were prepared as above at 4.3 and 8.6 N:P ratios. Explants were prepared from 6-8 week old C57 wild type mice by enucleation and removal of the anterior chamber. The retina and RPE/sclera were separated, flattened and placed in 500 μL 5% $CO_2$ equilibriated DMEM with 10% FBS and 100 U/mL Pen-Strep. Compacted pCAGLuc, 2 μg, or control plasmid alone was added to explants and the mixture was incubated for 48 hours (4.3 N:P ratio n=8, 8.6 N:P ratio n=3). For injections in vivo, 0.2 μg of compacted DNA or naked DNA was injected subretinally (all conditions n=4). The eyes were harvested 48 hours later and the anterior chamber removed. In both explants and in vivo injections, tissue was homogenized using a VWR PowerMax AHS 200 homogenizer in homogenization buffer (50 mM Tris HCl, pH 8.0, 150 mM NaCl) and assayed for luciferase expression according to the manufacturer's protocol (Promega) using a Glomax 20/20 luminometer (Promega). Protein concentration was measured using Quick Start Bradford Protein Assay (Bio-Rad) and quantitating by reference to a bovine serum albumin (Bio-Rad) standard curve in corresponding buffer.

Preparation and Characterization of PEGylated C-POD, TAT and CK30 Nanoparticles

To PEGylate, the peptide was resuspended in 0.1M sodium phosphate (pH 7.2), 5 mM EDTA to form a 20 mg/ml solution. An equimolar amount of methoxy-PEG-maleimide 10 kD (Nektar Transforming Therapeutics) was resuspended in the same volume of DMSO. PEG was added dropwise to the peptide for a period of about 10 minutes, vortexing between drops. The solution was shaken overnight at room temperature, and dialyzed using a Bio-gel P6 column (Bio-Rad) into 0.1% trifluoroacetic acid for POD and TAT and 50 mM ammonium acetate for CK30 [Ziady A G et al. 2003 Mol Ther 8: 936-947]. The PEGylated POD (PEG-POD) was quantified by Coomassie stain of a Tris-HCl gel (Bio-Rad) using a C-POD standard curve. Both CK30 and TAT were observed to not be within the detectable limits of Coomassie stain, so protein concentration was performed using BCA Protein Assay Kit (Thermo Scientific) using the un-PEGylated peptide to obtain a standard curve. DNA was compacted by diluting the plasmid in water to a final concentration of 0.2 μg/μl and added dropwise to PEG-POD or PEG-TAT (final ratio 1.8 nMole peptide:2 μg DNA), vortexing to mix. The nanoparticles were dialyzed three times in 5% dextrose using Biomax 10K centrifugal filter (Millipore) and stored at 4° C. PEG-CK30 particles were compacted following a previously described protocol [Ziady A G et al. 2003 Mol Ther 8: 936-947; Liu G et al. 2003 J Biol Chem 278: 32578-32586], but briefly, 0.9 mL DNA (200 μg/mL) was added to 0.1 mL of 7.1 mg/mL PEG-CK30 in 0.1 mL aliquots for a period of during a time period of about 2 minutes at 25° C. The compacted DNA was dialyzed overnight into 0.9% filtered NaCl at 4° C. (Tube-O-Dialyzer, G-Biosciences, St. Louis, Mo.) and concentrated by centrifugation (Ultrafree, Millipore, NMWL 100 kD). Plasmid compaction for each peptide was verified by reduced mobility through a 1% agarose gel (Invitrogen), which was relieved after 15 minute incubation with 0.25% trypsin (Invitrogen) at 37° C. PEG-POD articles were analyzed by incubation on glow-discharged Formvar copper grids (Electron Microscopy Sciences), stained with 0.4% uranyl acetate, and visualized using CM10 Transmission Electron Microscope (FEI, Hillsboro, Oreg.) using Digital Micrograph software (Gatan, Pleasanton, Calif.). PEG-POD particles and control samples were diluted to 0.2 mg/ml and analyzed at 25° C. using a BIC BI-200 SM research goniometer and laser light scattering system (Brookhaven Instruments Corporation, Holtsville, N.Y.) with 532 nm laser light. Data was collected for 5 minutes for each sample and the mean particle diameter determined by quadratic fit using software supplied by the manufacturer.

Localization of Compacted DNA In Vitro and In Vivo

Rhodamine labeled DNA (pGeneGrip, Gene Therapy Systems) was compacted with either C-POD or PEG-POD as described. Compactions were added to HER cells grown to about 80% confluency on Lab Tek-II chamber slides in serum free DMEM to a final concentration of 0.66 μg/ml and incubated at 37° C., 5% $CO_2$ for 24 hours (for each condition, n=4). Cells were fixed with 4% formalin for 15 minutes at room temperature. For localization in vivo 0.1 μg of the compacted plasmid was injected subretinally into 6-8 week C57 mice, harvested after two hours and fixed overnight in 4% paraformaldahyde. Eyes were dehydrated, embedded in Optimal Cutting Temperature Compound (Sakura) and 14 μm sections collected using a Microm 550 cryostat. Imaging was performed as above using an Olympus BX51 microscope (for each condition, n=4).

PEG-Peptide/DNA Nanoparticle Transfections In Vivo

Subretinal injections were performed as above and luciferase activity assayed as for C-POD compactions. All injections were performed in a 2 μL total volume. For uninjected, DNA only and 0.6 μg POD, n=4; for 1.2 μg POD n=8; for 1.2 μg TAT and CK30 n=6. For tail vein injections, compacted or naked DNA was injected in a total volume of 200 μl with 0.01% fast green (Fisher) using a 25 G needle (Becton Dickinson). For uninjected n=2; for 40 μg naked DNA n=6; for 10 μg PEG-POD~Luc n=3; for 40 μg PEG-POD~Luc n=4. At a time point of 48 hours after injection, mice were sacrificed using $CO_2$, perfused with 800 μl PBS through the left ventricle. The organs were harvested, placed in 500 μl Luciferase Cell Culture Lysis Reagent (Promega) with 20 μl/ml of a protease inhibitor cocktail (Sigma) and homogenized for 20 seconds. Homogenates were centrifuged at 4° C. for 10 minutes at 12,000×g and assayed for luciferase activity as per manufacturer's instructions (Promega) and protein concentration as mentioned above. Standard curve values for the luminometer were determined using QuntiLum Recombinant Luciferase (Promega). Conversion from relative light units (RLU) to pg was calculated as: luciferase (pg)=$(3.696\times10^{-5}\times RLU)-0.0815$ ($R^2$=0.9999). For β-galactosidase expression, 1.2 µg of either compacted or naked pCAGLacZ was injected subretinally in BALB/CJ mice. After 48 hours, eyes were enucleated and fixed in 0.25% glutaraldehyde for 30 minutes. The eyes were incubated in X-Gal Working Solution (0.75 mL 40 mg/ml X-Gal (Fisher) in dimethylformamide, 1.5 ml 20× KC solution [0.82 g $K_3Fe(CN)_6$, 1.05 g $K_4Fe(CN)_6$-$3H_2O$], 0.015 ml 1M $MgCl_2$, 28 ml PBS) for 16-18 hours and then rinsed in phosphate buffer (pH 7.4) for 45 minutes. The eyes were fixed for 24 hours in 4% PFA, dehydrated, embedded and 18 µm sections were collected. Whole eye bright-field images were taken using a C-FMC microscope prior to sectioning. For all conditions, n=4.

DNA Stability Assay in Presence of Serum

PEG-POD 700 ng compacted or naked pCAGLuc (700 ng) was treated with 2.5 U or 0.25 U DNaseI (Sigma) at 37° C. for 15 minutes, after which 10 µg pronase (Sigma) was added and incubated for a further 10 minutes at 37° C. The samples were then analyzed by 1% agarose gel electrophoresis to check for DNA degradation.

Electroretinography

Mice were injected subretinally with 1 µl of PEG-POD~Luc nanoparticles (700 ng) or 1 µl of 5% dextrose buffer and analyzed by electroretinography (ERG) 48 hours later as follows. After overnight dark-adaptation, mice were anaesthetized as described above, pupils were dilated with 1% tropicamide (Akorn, Inc), and scotopic ERGs were recorded at three different light intensities (−2 to 0 dB) using contact lens electrodes and the UTAS system with BigShot ganzfeld (LKC Technologies, Inc). For each animal, 5-10 flashes were observed and were averaged for the high-low intensities. For each condition, n=4.

Statistical Analysis

The data are presented as the log-transformed mean±SEM. Data analyses were done using Prism Software 4 (GraphPad Software, inc.). Analysis of the data shows a highly significant difference (p<0.0001) between the variances of the data sets that was mean dependent. This precludes analysis by Student's t-test, which assumes equal variances between samples. The data (RLU/mg) was logarithmically transformed to create a more Gaussian distribution, eliminating the variability between data set variance, and allowing use of the parametric t test [Armitage P et al. 2002 J.N.S. Statistical Methods in Medical Research. Blackwell Science, London]. Because subretinal injections are a variable technique, a method was devised to differentiate failed from successful injections. Data showed that the raw RLU increases above background, an observation here interpreted as a successful injection associated with a rise in RLA, even if only by a small margin, by three standard deviations above the mean when a blank alone was measured [Ziady A G et al. 2003 Mol Therapy 8: 936-947]. All data points are shown, and only those above blank+3 SD are used in the statistical analysis and to calculate the means.

Example 1

POD is a Cell Penetrating, Non Membrane-Permeabilizing Peptide

Human embryonic retinal (HER) 911 cells [Fallaux F J et al. 1996 Hum. Gene Ther. 7: 215-222] incubated with 2 mmoles (8 µM) lissamine-conjugated POD (L-POD), followed by formalin fixation, became opaque to 558 nm excitation (emission measured at 583 nm) within 1 min and appeared normal in bright field (FIG. 1 panel A). Within 5 min, L-POD was seen within the cytoplasm with both a diffuse cytoplasmic and slightly punctate pattern (Figure panel A). The majority of cells showed cytoplasmic staining by 60 min. Furthermore, there was no evidence of uptake of lissamine only (inset, FIG. 1 panel A). Cells that were not fixed, i.e. live cells, showed a similar rate of L-POD uptake, and a pattern of localization that was almost exclusively punctate at both 15 min and 60 min. Again, there was no evidence of uptake of lissamine only by live cells (FIG. 1 panel 8).

To determine whether L-POD was internalized or was non-specifically associated with the plasma membrane, HER cells incubated with 2 nmoles (8 µM) L-POD for 15 min were treated with trypsin at 37° C. prior to counting of lissamine-positive cells by FACS. A total of 90.10±1.89% or 92.23±0.65% of cells were observed to be lissamine-positive with or without incubation with trypsin respectively (FIG. 1 panel C), showing that the majority of L-POD was internalized and not merely membrane associated. Sensitivity of POD peptide to trypsin-mediated digestion was confirmed by incubation of 2.5 mmoles of C-POD with trypsin prior to loading on an acrylamide gel (inset FIG. 1 panel C). Whereas 92.23±0.65% of HER cells were lissamine-positive when incubated with L-POD at 37° C., only 48.74±2.32% of cells were lissamine-positive when incubated with L-POD at 4° C. (FIG. 1 panel D). Hence, uptake of L-POD was found to be temperature dependent.

To determine whether uptake of POD required plasma membrane disruption, HER cells were incubated with increasing concentrations (ranging from 0.2 to 2.0 µM) of FITC-conjugated POD (F-POD) followed by a FACS measurement of the number of permeabilized cells by incubation with propidium iodide (PI). In this example F-POD rather than L-POD was utilized to reduce bleed of the lissamine-signal into that of PI. An average of 3.98±0.70% of cells were observed to be PI-positive when pre-incubated with F—POD, similar to the number of PI-positive cells in the absence of any peptide, 5.18±3.00% (FIG. 1 panel E). In contrast, 91.44±9.66% of the cells were PI-positive when incubated with the cell permeabilizing detergent, 1% Triton-X100 (FIG. 1 panel E). These data show that F-POD enters HER cells without substantially disrupting the plasma membrane.

Example 2

POD-Mediated Delivery of Small and Large Molecules in Cell Culture

Potential use of an N terminal biotinylated POD (B-POD) peptide or an N terminal cysteine-containing POD (C-POD) peptide in delivering small and relatively large molecules to cells in culture was examined. To establish proof-of-principle, the following target classes were examined herein: siRNA, plasmid DNA and streptavidin-coated CdSe quantum dots. Biotin was chosen for convenient conjugation of a large variety of biologically relevant compounds to POD by use of a streptavidin bridge, as is shown herein for quantum dots, or direct chemical linkage to cysteine through the free sulfhydryl bond.

In initial examples, a 5.5 Kb plasmid containing a red fluorescent protein expression cassette (pCAGRFP) was complexed electrostatically with C-POD in 5% dextrose, incubated with HER 911 cells and analyzed by FACS 48 hours later. It was observed herein that pCAGRFP alone or pCAGRFP complexed with C-POD resulted in only 2.45±0.31% and 2.20±0.46% RFP-positive cells respectively (FIG. 2 panel A). In contrast, when pCAGRFP was complexed with C-POD in Na2HPO4 buffer, 55.58±8.23% of HER cells were observed to be RFP-positive cells (FIG. 2 panel A) indicating that C-POD and the specific buffer were important components of the gene delivery complex. Examination of C-POD/pCAGRFP complexes in the two differently performing buffers by electron microscopy indicated that complexes prepared in $Na_2HPO_4$ had an average area of 63.31 $nm^2$, while those prepared in dextrose were 29.66 $mm^2$ (FIG. 2 panel B). This difference plays a role in the different rates of gene transfer in the two buffers.

C-POD was subsequently used to deliver a plasmid containing an expression cassette for green fluorescent protein (pEGFP) to HER cells, resulting in 49.13±2.23% GFP-positive cells (FIG. 2 panel C). Transfected cells were then incubated with either free siRNA duplex or with siRNA duplex complexed with C-POD, resulting in 39.86±2.20% and 24.79±1.18% GFP-positive cells respectively (FIG. 2 panel C). These data show that delivery of siRNA by C-POD was enhanced compared to siRNA alone and that this approach was a useful, non-toxic method for delivery of siRNA to enhance the knock down of gene expression.

To examine the potential of delivering larger cargo with POD, B-POD conjugated with streptavidin coated quantum dots (QDPOD) was used. HER cells incubated with QDPOD resulted in QDPOD-associated fluorescence within 15 min. QDPOD was also found in a punctate pattern within cells at 120 min (FIG. 2 panel D). In contrast, streptavidin-coated quantum dots without B-POD were not taken up by HER cells (FIG. 2 panel E). These data show that POD is capable of delivery is a very large cargo.

Example 3

Uptake of POD is Inhibited by Proteoglycans and POD has Microbicidal Activity

To determine whether L-POD uses cell surface proteoglycans for binding and cell entry, L-POD was pre incubated with different amounts of either of the proteoglycans chondroitin sulfate or heparan sulfate, prior to addition to HER cells. Based on data from preliminary studies, ratios of L-POD:proteoglycan of 1:3.33, 1:6.67 and 1:8 were selected.

Figure 3A:
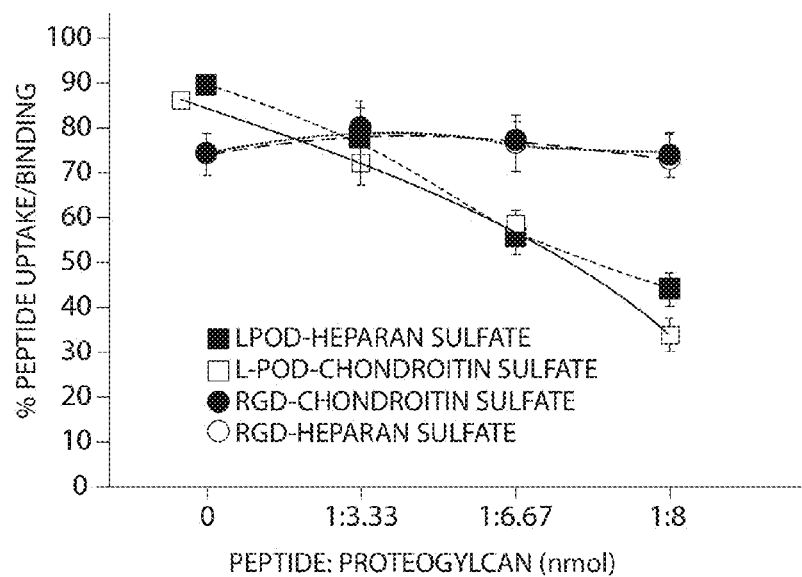
FIG. 3 is a line graph and a bar graph showing that POD uptake was influenced by cell surface proteoglycans and POD has microbicidal activity.
Figure 3B:
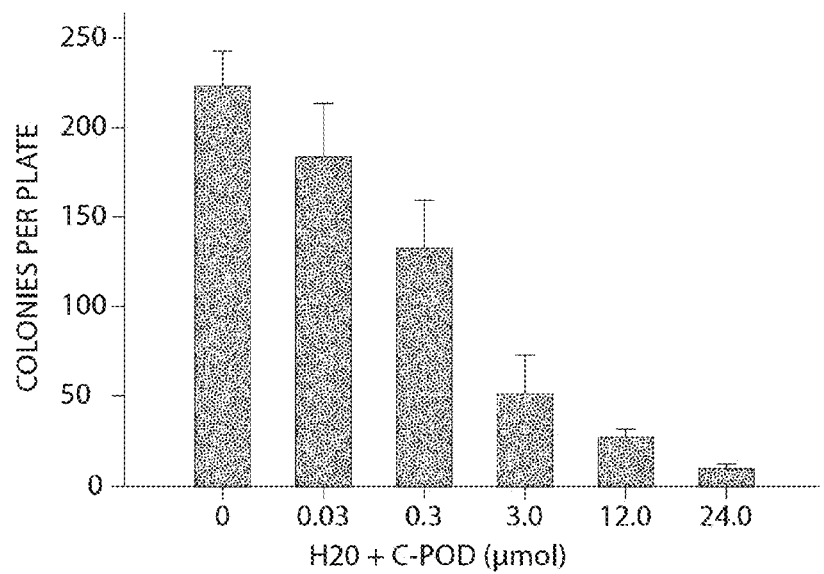
Figure 4A:
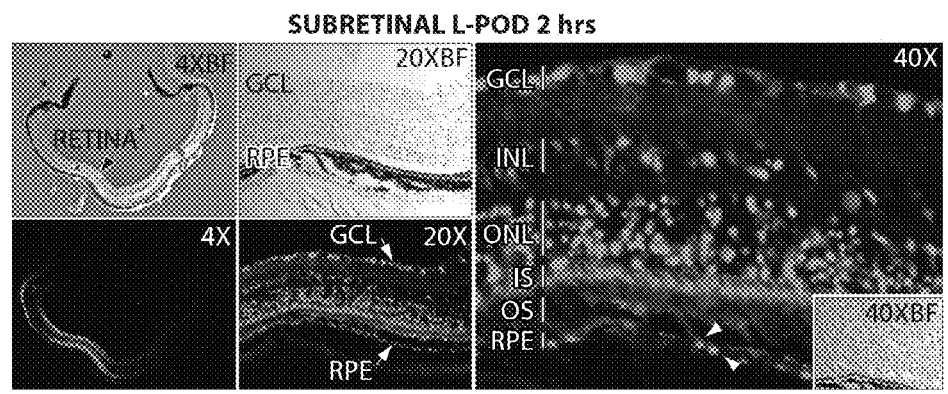
FIG. 4 is a set of photomicrographs showing that POD penetrates and carries cargo to retinal tissues in vivo.
Figure 4B:
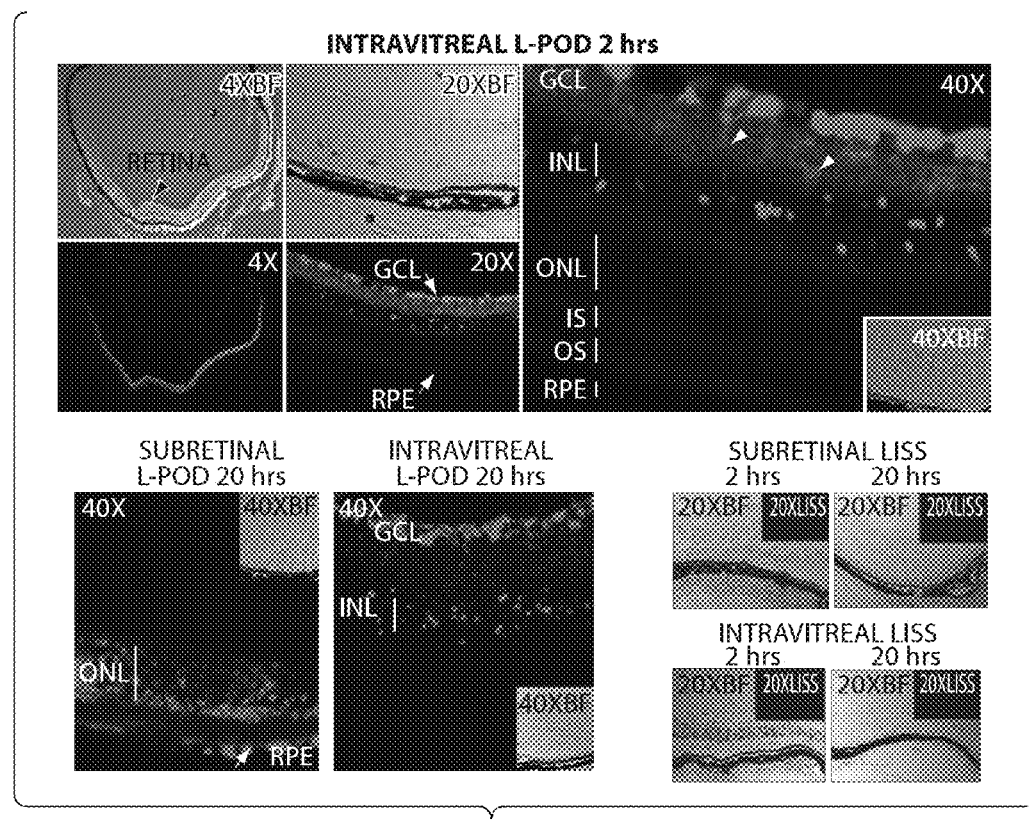
Figure 4C:
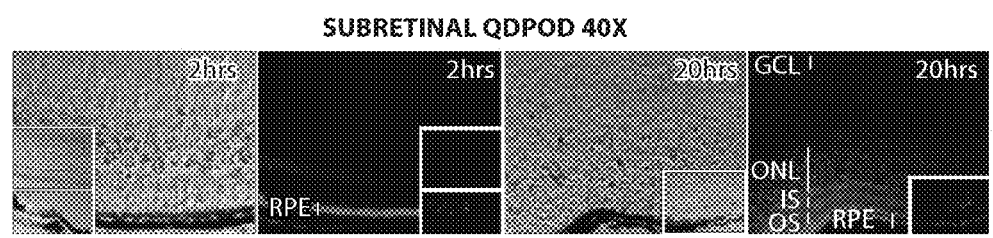
Figure 4D:
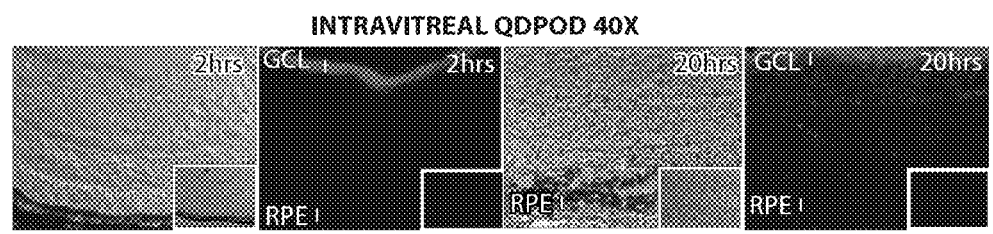
Figure 5A:
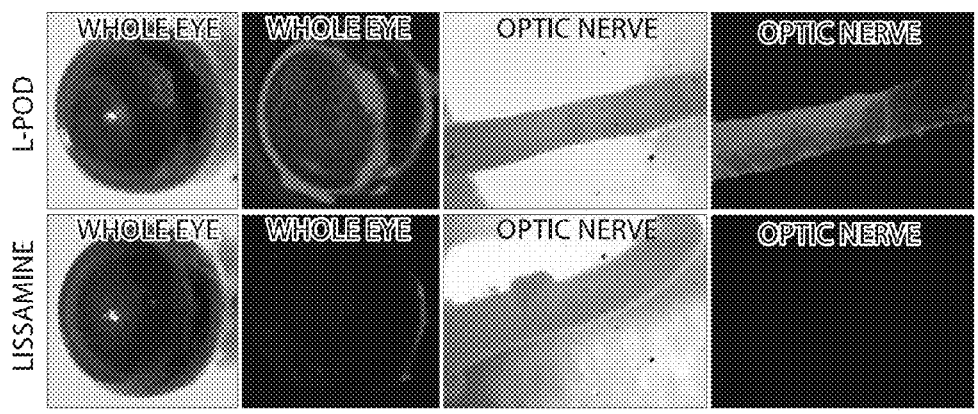
FIG. 5 is a set of photographs and photomicrographs that show that POD penetrates ocular tissues by topical application in vivo.
Figure 5B:
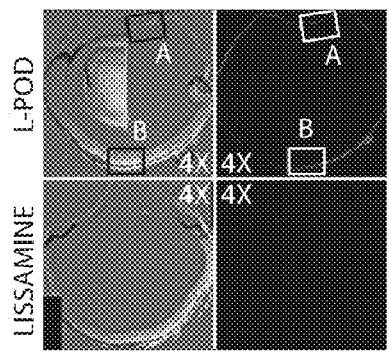
Figure 5C:
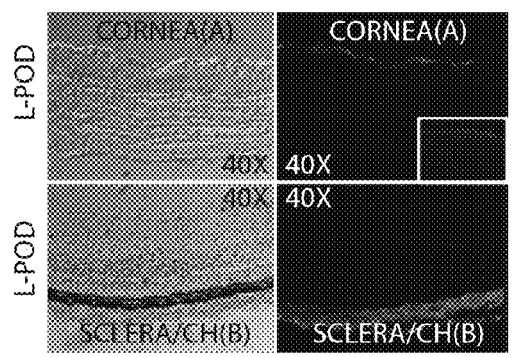
Figure 5D:
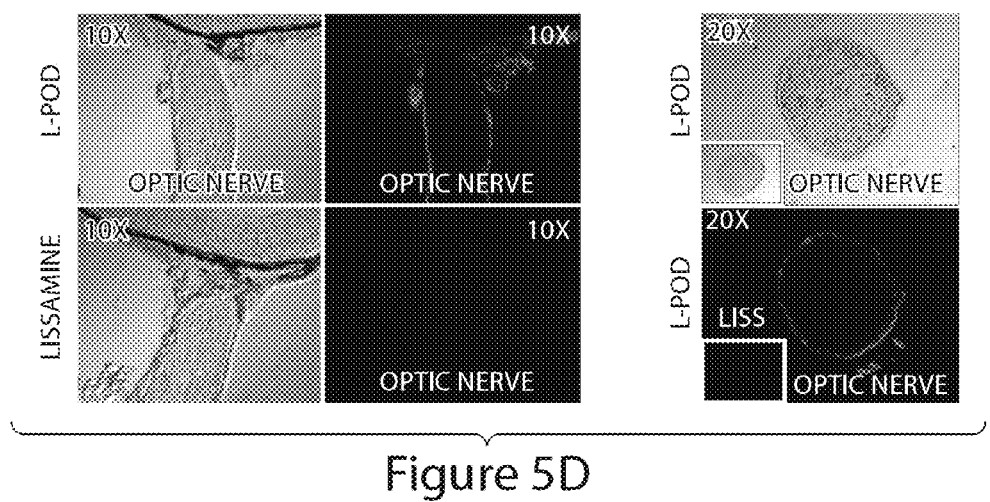

Without pre incubation of L-POD with any proteoglycan, 90.07±0.64% of cells were lissamine-positive, whereas increasing ratios of chondroitin sulfate led to a decrease in uptake of L-POD to 71.24±1.77%, 59.43±1.55%, and 34.38±3.13% at 1:3.33, 1:6.67 and 1:8 molar ratios respectively (FIG. 3 panel A). Similarly, pre incubation of L-POD with heparan sulfate reduced uptake to 78.60±0.35%, 57.78±2.83%, and 44.37±2.17% respectively at the same ratios described above (FIG. 3 panel A). In contrast, the uptake of a TRITC-conjugated peptide containing an integrin-binding RGD motif was not affected by pre-incubation with either proteoglycan (FIG. 3 panel A).

Since endophthalmitis, an infection within the eye, is regularly a complicating factor in drug delivery to ocular tissues [Ho J et al. 2007 Int Opthalmol Clin 47: 199-208], C-POD was examined for potential microbicidal activities. E. coli cells grown to mid-log phase were incubated with either H20 only or C-POD suspended in $H_2O$ at concentrations ranging from 0.03 µM to 60 µM, and cell number was determined by plating samples on LB agar. Significant inhibition of bacterial growth was observed at C-POD concentrations of 0.30 µM (FIG. 3 panel B) and almost complete inhibition at 24.0 µM C-POD. Greater concentrations of C-POD completely eliminated bacterial growth. Hence, data showed that C-POD has microbicidal activity and that this activity is concentration dependent.

Example 4

POD-Mediated Delivery of Small and Large Molecules to Retina In Vivo

Delivery of L-POD into the subretinal space (a space created between the photoreceptors and the retinal pigment epithelium (RPE) following delivery of fluids) of adult C57BL/6J mice followed by harvesting of tissue 2 hours later resulted in approximately 40% transduction of neural retina (FIG. 4 panel A, magnification 4×). Within this region, there was substantial transduction of several layers of the retina including the RPE (FIG. 4 panel A, magnification 20×). Closer examination reveals significant transduction of photoreceptor cell bodies, photoreceptor inner segments, cells in the inner nuclear layer and ganglion cells (FIG. 4 panel A, magnification 40×). Although nuclei were not strongly positive in cell culture data described above, in vivo transduction of retina indicated that L-POD localized to nuclei in the case of RPE transduction (arrowheads, FIG. 4 panel A, magnification 40×). As the nuclei of photoreceptor cells are large relative to the cell body, nuclear versus cytoplasmic localization could not be differentiated for those cells.

Delivery of L-POD into the intravitreal space (the region between lens and retina) transduced approximately 85% of the neural retina (FIG. 4 panel B, magnification 4×) within 2 hours. Strong staining was seen in the ganglion cell layer, inner plexiform layer and inner nuclear layer (FIG. 4 panel B, magnification 20×). Closer examination revealed significant transduction of the ganglion cells and dendrites associated with the inner plexiform layer (arrowheads FIG. 4 panel B, magnification 40×). There was no significant transduction of the outer layers of the retina by intravitreal injection at the 2 hour time point.

In contrast to L-POD, delivery of the significantly larger QDPOD complexes into the subretinal or intravitreal space appeared to permit cell binding but not uptake per se in the 2 hour time period following injection (FIG. 4 panel C and 4 panel D). However, a longer incubation period of 20 hours revealed uptake of QDPOD into the outer nuclear layer following subretinal injection (FIG. 4 panel C) or into the inner layers of the retina upon intravitreal injection (FIG. 4 panel D).

Control quantum dots that were coated with streptavidin only, showed only weak uptake by the RPE at 2 hrs and slightly greater but still minimal uptake at 20 hrs by the RPE (insets, FIG. 4 panel C). Similarly, there were insignificant levels of uptake of control quantum dots upon intravitreal administration (insets, FIG. 4 panel D).

Example 5

POD-Mediated Delivery of Cargo to Ocular Tissues by Topical Application In Vivo

To assess penetration of the cornea and sclera with L-POD, whole mouse eye was incubated in vivo with 10 nmol L-POD for 45 min followed by harvesting of ocular tissues.

It was observed that within 45 min, L-POD bound strongly to the cornea, sclera and unexpectedly, also the optic nerve (FIG. 5 panel A). In contrast, lissamine only weakly stained the cornea and sclera and did not stain the optic nerve (FIG. 5 panel A). Frozen cross-sections of these eyes revealed that the entire outer ocular surface was positive for LPOD in contrast to lissamine, that only weakly stained these tissues (FIG. 5 panel B). Closer examination of cornea and sclera indicated that there was strong staining of the corneal epithelium and sclera/choroid within this 45 min time period (FIG. 5 panel C). Longitudinal and cross-sections of optic nerve indicated that the outer layers of the optic nerve were transduced with L-POD (FIG. 5 panel D) at the 45 min time point. There was no staining observed with lissamine only (FIG. 5 panel D) in similar data in Examples herein.

Example 6

De Novo Synthesized POD-GFP Localizes to the Nucleus

Figure 7A:
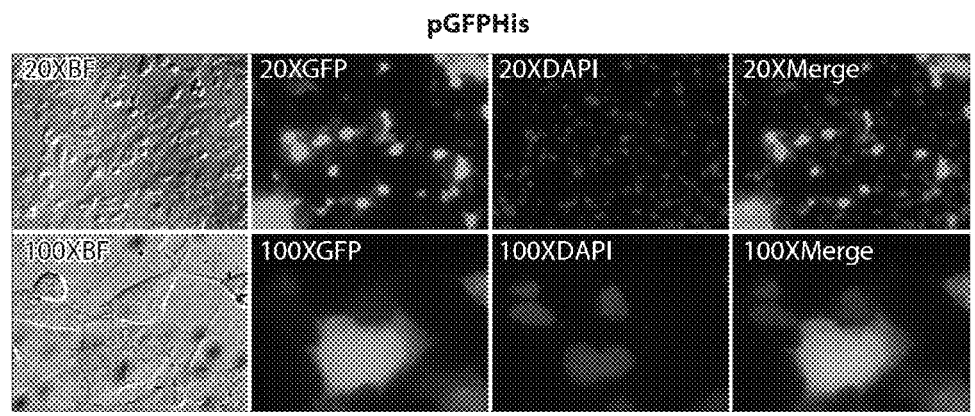
FIG. 7 is a set of photomicrographs showing that de novo synthesized POD-GFP fusion protein localizes to the nucleus.
Figure 7B:
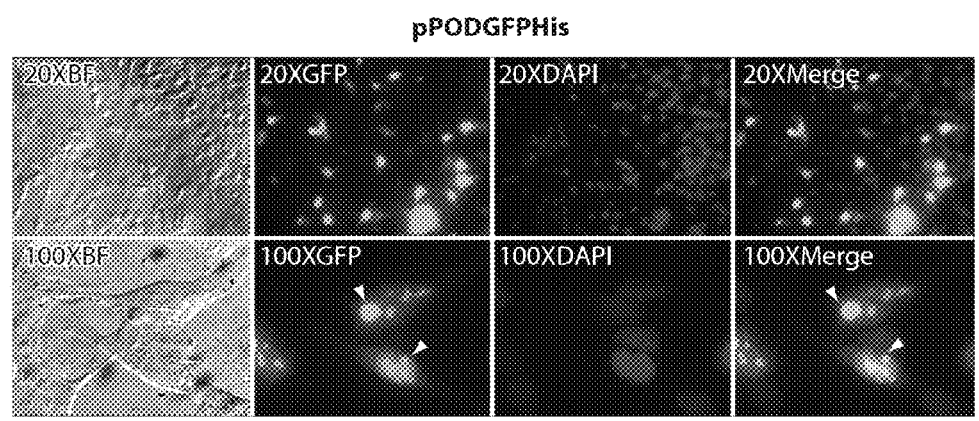

Transfection of human embryonic retinoblast (HER) cells [Fallaux F J et al. 1996 Hum. Gene Ther. 7: 215-222] with pGFPHis, a plasmid expressing a His-tagged GFP, resulted in relatively diffuse cytoplasmic and nuclear localization of recombinant GFP (FIG. 7 panel A). In contrast, transfection of HER cells with pPODGFPHis, a plasmid expressing a His-tagged POD-GFP fusion protein, resulted in relatively weak cytoplasmic and intense nuclear localization (FIG. 7 panel B). Furthermore, POD-GFP appeared to concentrate in sub nuclear compartments (FIG. 7 panel B, arrowheads).

This pattern of localization associated with POD-GFP observed herein contrasts with that of exogenously added lissamine-conjugated POD peptide (L-POD), shown in examples herein to localize primarily to the cytoplasm in a punctate pattern—reminiscent of endocytosis [Johnson L N et al. 2007 Mol Ther 16: 107-114].

These data show that endogenously expressed POD functions as a nuclear localization signal for POD fusion proteins.

Example 7

Purification of POD-GFP from Adenovirus-Infected HER Cells

Figure 8A:
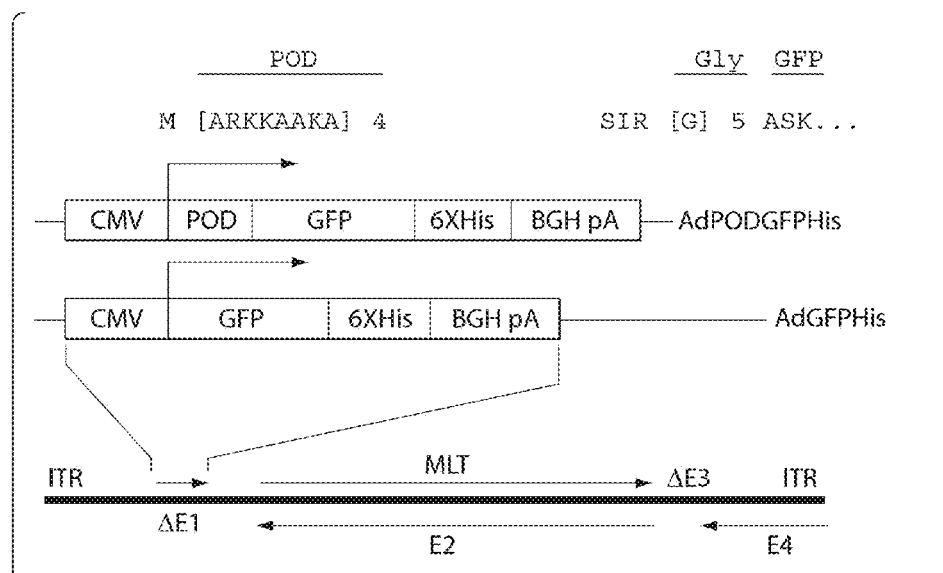
FIG. 8 is a drawing and a set of photographs, showing purification of POD-GFP from adenovirus-infected HER cells. Expression cassettes encoding POD-GFP or control GFP were cloned into the deleted E1 region (ΔE1) of a first generation adenovirus vector. POD was fused to GFP via a flexible polyglycine linker (FIG. 8 panel A).
Figure 8B:
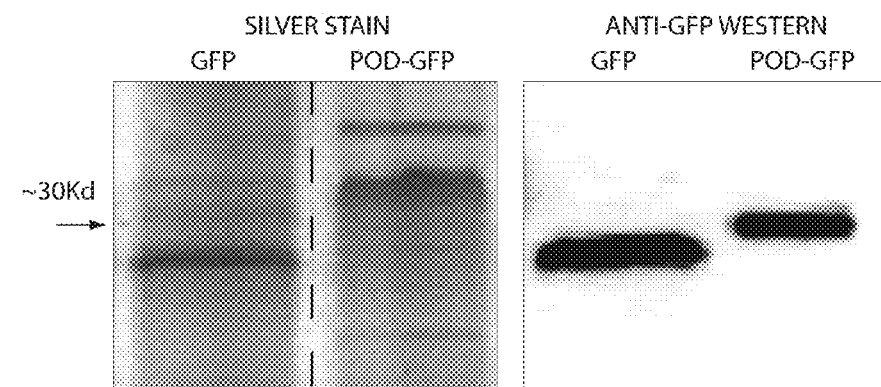

To examine protein transduction by exogenously supplied POD-GFP, expression cassettes coding for His-tagged POD-GFP or GFP, regulated by a CMV promoter, were cloned into an E1/E3-deleted human adenovirus serotype 5 vector, AdPODGFPHis and AdGFPHis respectively (FIG. 8 panel A). POD-GFP and GFP were purified from adenovirus infected HER cells and electrophoresed on a Tris-HCl acrylamide gel. Following silver staining, major bands were identified at approximately 32 and 28 Kd, corresponding to roughly the predicted molecular weight of POD-GFP and GFP respectively (FIG. 8 panel B). Minor bands of slightly greater molecular weight were also detected for each of the proteins by silver staining.

Western blot analyses of the purified protein fractions using a monoclonal antibody that specifically binds to GFP showed that the major bands corresponded to GFP and POD-GFP respectively (FIG. 8 panel B).

These data show that recombinant adenovirus vectors generated relatively pure preparations of POD-fusion proteins when expressed in human cells.

Example 8

Transduction Properties of POD-GFP In Vitro

Figure 9A:
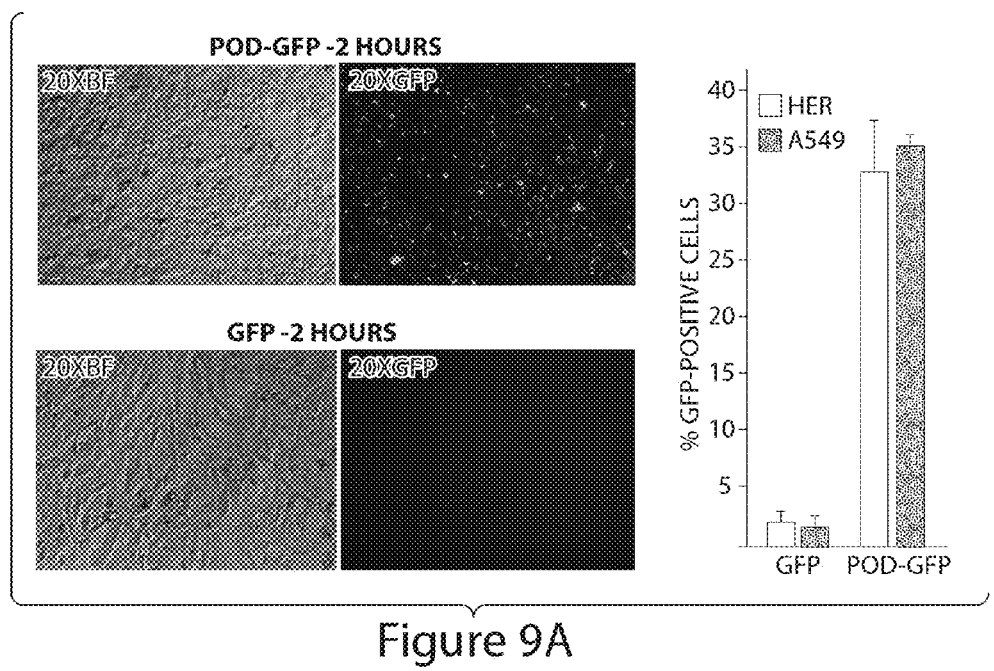
FIG. 9 is a set of photomicrographs and a bar graph showing transduction properties of POD-GFP in vitro.
Figure 9B:
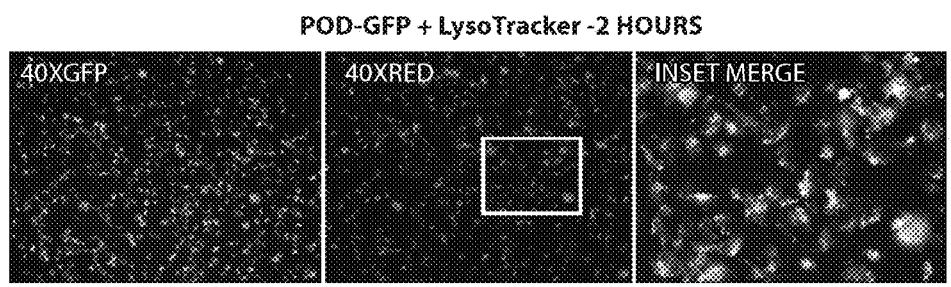

To determine the transduction capabilities of POD-GFP in vitro, each of approximately $0.2 \times 10^6$ human lung carcinoma epithelial cells (A549) or HER cells were incubated with 10 µg of each of purified recombinant POD-GFP or control GFP protein for 2 hours and the number of GFP-positive cells were counted by FACS. Data shows that 35.3±0.9% and 1.4±0.4%, respectively, of A549 cells were GFP-positive when incubated with POD-GFP or GFP, respectively. Similarly, 34.2±3.4% and 1.8±0.4%, respectively, of HER cells were GFP-positive when incubated with POD-GFP or GFP, respectively (FIG. 9 panel A).

Extent of toxicity to cells during protein transduction was measured by uptake of propidium iodide (PI). Data shows that 2.8±3.8% or 3.2±2.7%, respectively, of HER cells were PI-positive after cells were incubated with POD-GFP or GFP, respectively, similar to that of untransfected cells (3.6±3.0%). These data shows that little toxicity was observed.

In contrast to endogenous gene expression, POD-GFP in the Example herein appeared in the cytoplasm of HER cells in a punctate pattern (FIG. 9 panel B), similar to observations in examples above with L-POD peptide and similar to that of an endocytic mechanism of uptake. POD-GFP failed to colocalize with ER tracker or DAPI, and was observed here to colocalize in part with Lysotracker (FIG. 9 panel B), a marker of late endosomes—consistent with a model by which POD-OFF enters cells by more than one mechanism.

These data show that POD-GFP transduced cells in culture, and did not significantly damage the plasma membrane during entry, and in contrast to protein delivered by endogenous expression from a nucleic acid vector, POD-GFP colocalized in part with late endosomes.

Example 9

Transduction Properties of POD-GFP In Vivo

To determine the transduction properties of POD-GFP in vitro an amount of 8.5 µg of each of purified POD-GFP or control GFP protein was injected into the subretinal space, i.e., between the retinal pigment epithelium (RPE) and photoreceptors, of 6 week-old male C57BL61J mice. Eyes were harvested after 6 hours and frozen sections were examined by fluorescence microscopy.

Data showed that GFP-fluorescence associated with injection of control GFP protein was detected in the subretinal space, and the amount was barely discernible above background auto-fluorescence. Furthermore, there was no evidence of GFP in any other part of the retina in an amount exceeding that of auto-fluorescence (FIG. 10 panel A).

Figure 10A:
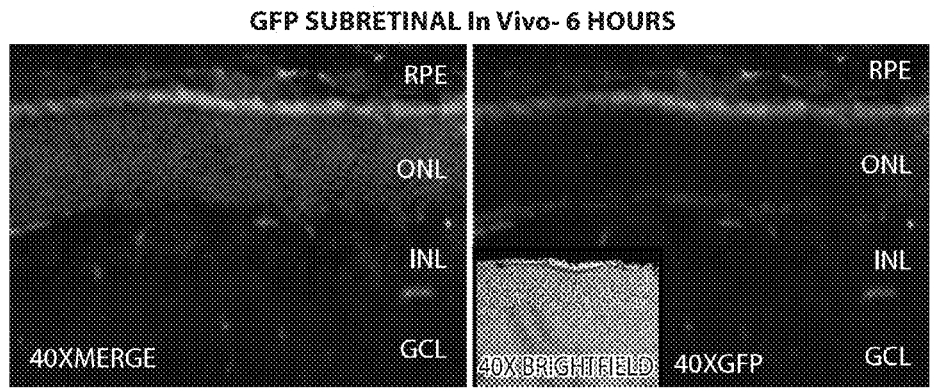
FIG. 10 is a set of photomicrographs showing transduction properties of POD-GFP following subretinal injection in vivo. POD-GFP or control GFP protein was injected into the subretinal space of adult mice.
Figure 10B:
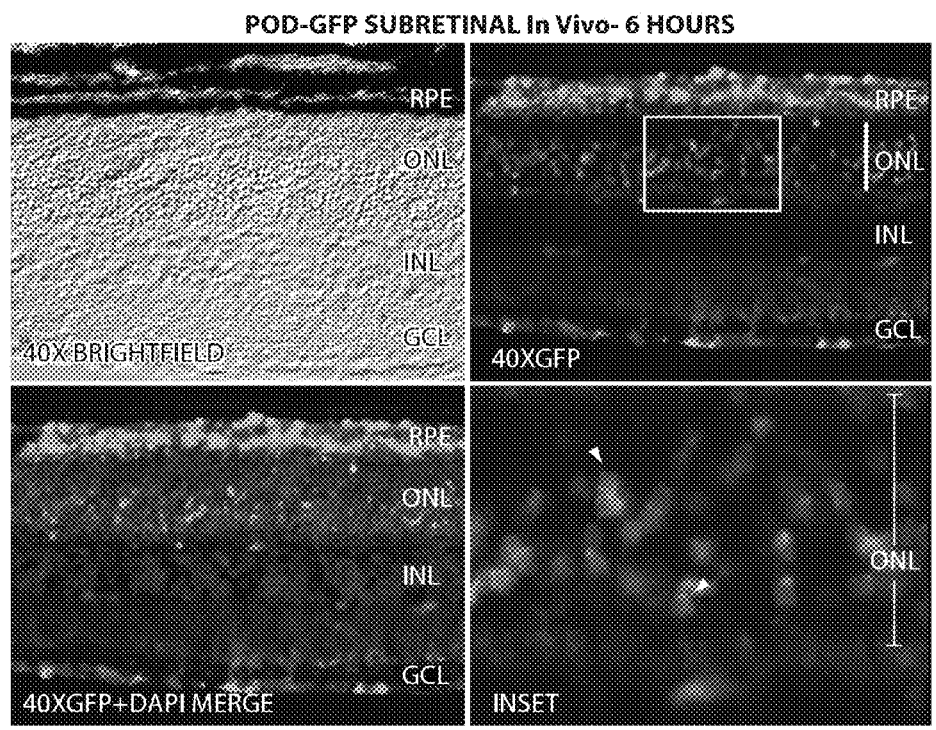

In contrast, POD-GFP was observed localized to the subretinal space, and was also detected in the RPE and was abundantly present in the outer nuclear layer (ONL), i.e. the location of the photoreceptor cell bodies (FIG. 10 panel B). Depending upon extent of retinal detachment created during the injection procedure, transduction of the ONL was found in up to 40% of the retinal surface. Occasional GFP-positive cells were also noted in the nerve fiber layer and ganglion cell layer (GCL) following subretinal injection. Closer examination of the photoreceptor cell bodies in the ONL showed localized POD-GFP in the perinuclear space or plasma membrane, appearing in both a punctate and membrane-associated pattern (FIG. 10 panel B, arrowheads).

Figure 11A:
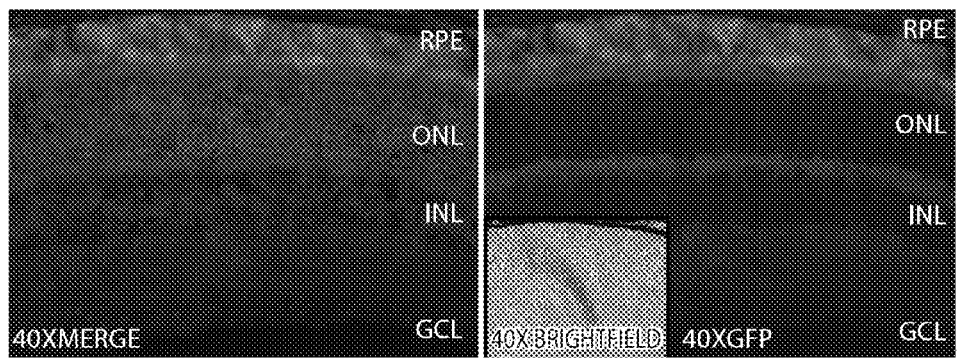
FIG. 11 is a set of photomicrographs showing transduction properties of POD-GFP following intravitreal injection in vivo. POD-GFP or GFP protein was injected into the intravitreal space of adult mice and eyes harvested after 6 hours.
Figure 11B:
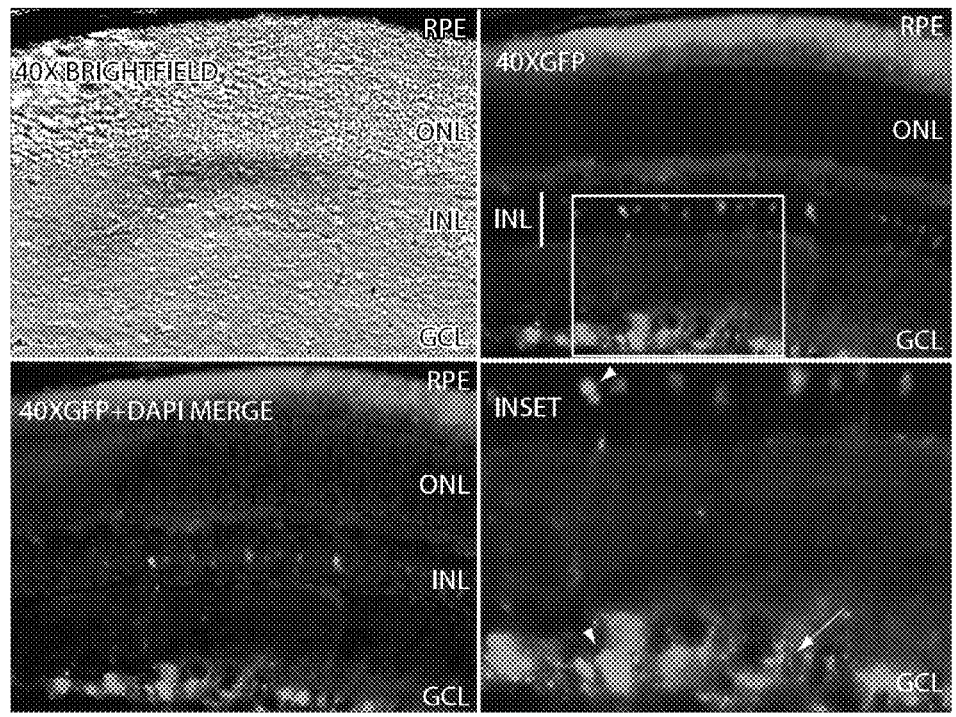

Purified POD-GFP, 6.6 µg, or that amount of control GFP protein was injected into the intravitreal space, i.e. between the lens and neural retina of 6 week-old male C57BL6/J mice, and eyes were harvested after 6 hours and frozen sections examined by fluorescence microscopy. The data show that following intravitreal injection, GFP-fluorescence associated with injection of control GFP protein was not detected in retinal cells above background auto-fluorescence (FIG. 11 panel A). In contrast, POD-GFP was readily detected in ganglion cells (FIG. 11 panel B) and in a subpopulation of cells in the inner nuclear layer (INL; FIG. 11 panel B, arrowheads). Unlike with subretinal injection, no POD-GFP signal was detectable in the outer nuclear layer or RPE beyond that of background auto-fluorescence and the overall number of GFP-positive cells was less than that achieved by subretinal injection. Closer examination of the inner retina revealed that a large number of dendtrites also contained POD-GFP (FIG. 11 panel B, arrow).

Figure 12A:
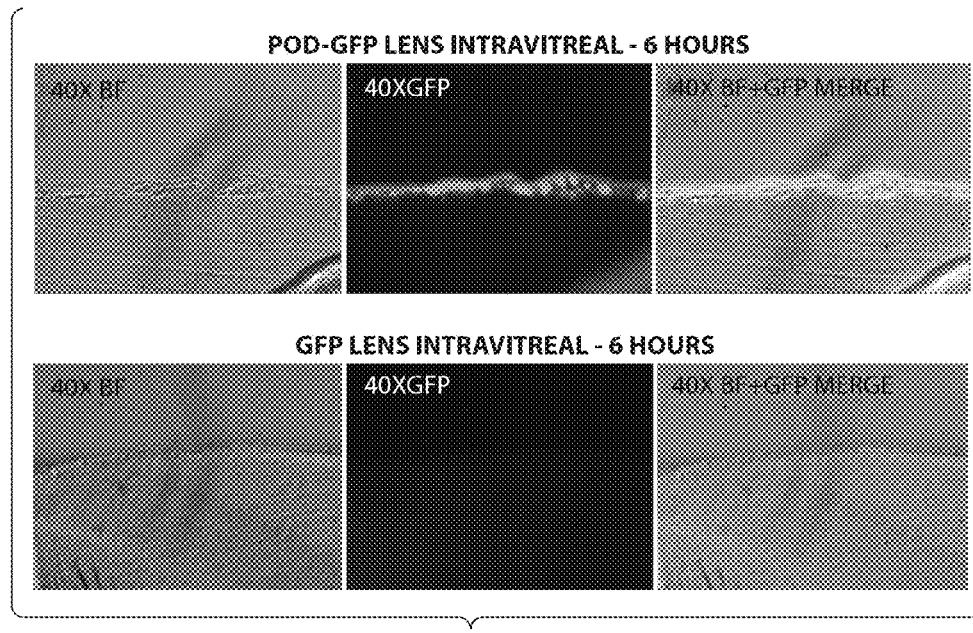
FIG. 12 is a set of photomicrographs and photographs showing transduction of lens capsule following intravitreal injection and topical application of POD-GFP on murine cornea in vivo.
Figure 12B:
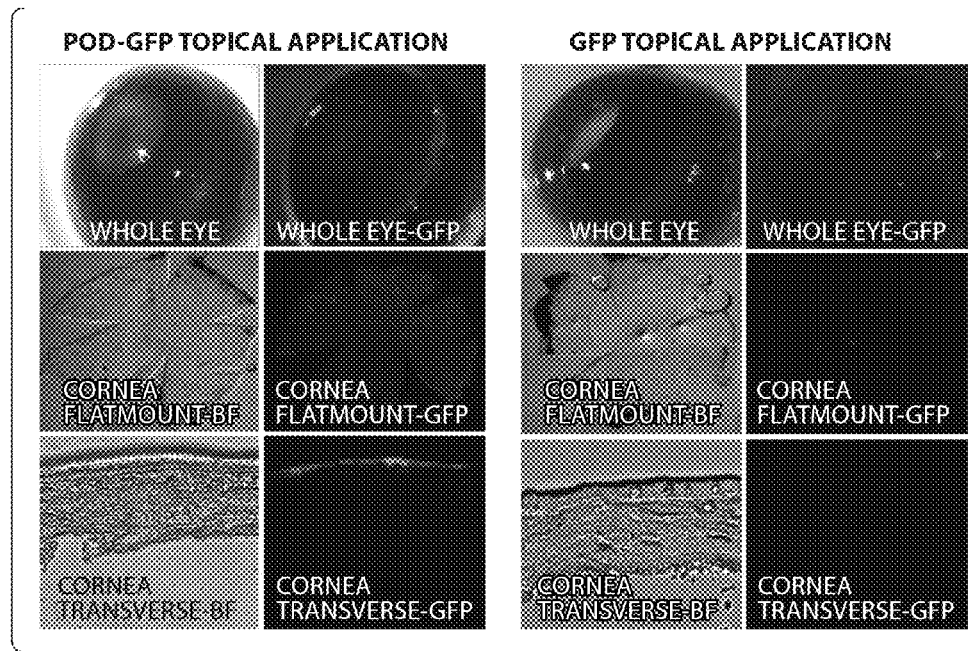

Further, the lens capsule following intravitreal injection had a very strong affinity for POD-GFP but not for GFP (FIG. 12 panel A). The affinity of POD-GFP for the lens reduced the amount of protein available for retinal transduction, associated with observation of poorer transduction of the neural retina by the intravitreal route relative to the subretinal route.

In summary, data herein show that POD-GFP delivered to the intravitreal space transduces the ganglion cells and a limited number of cells in the INL, as well as the lens capsule. In contrast, delivery of POD-GFP into the subretinal space transduces the RPE and photoreceptor cells.

Example 10

Topical Application of POD-GFP to Cornea In Vivo

Purified POD-GFP, 40 µg, or control GFP protein was topically applied to the cornea of an anesthetized 6 week-old male C57BL6/J mouse, and eyes were harvested 45 minutes later for sectioning. Excitation of whole mouse eyes with 474 nm light revealed that the control GFP was washed away and therefore absent from the outer surface of the eye. In contrast, POD-GFP was detected on most of the ocular surface (FIG. 12 panel B).

To further examine localization of POD-GFP, anterior ocular tissues were dissected and the corneas were flat mounted or cross-sectioned and re-examined by fluorescence microscopy. Data showed that control GFP-fluorescence was not detectable in flat mounts that had been prepared from mice with topical application of GFP. In contrast, GFP-fluorescence was readily detected on both flat mounts and cross sections of corneas from mice that received topical application of POD-GFP (FIG. 12 panel B). Transverse sections revealed that the majority of the GFP-fluorescence associated with POD-GFP was observed in the corneal epithelium and minimally from the stroma (FIG. 12 panel B). No GFP-signal was detected in corneal cross-sections prepared from mice that received topical application of control GFP.

These data show that topical application of POD-GFP to ocular tissues permits binding to the corneal epithelium.

Example 11

Topical Application of POD-GFP to Skin In Vivo

The data and Examples herein describing the properties of POD focused primarily on retinal or ocular tissues. The success of the corneal topical application observed herein, and the potential of this mode of delivery for therapeutic proteins in general, prompted investigation of this type of application to other tissues.

To extend these observations to other organ systems, the potential of transdermal delivery of POD-fusion protein was examined. POD-GFP (40 µg) or control OFF was topically applied to shaved skin of adult C57BL6/J mice. Animals were sacrificed 24 hours later and frozen sections of the treated region were examined by fluorescence microscopy.

Figure 13A:
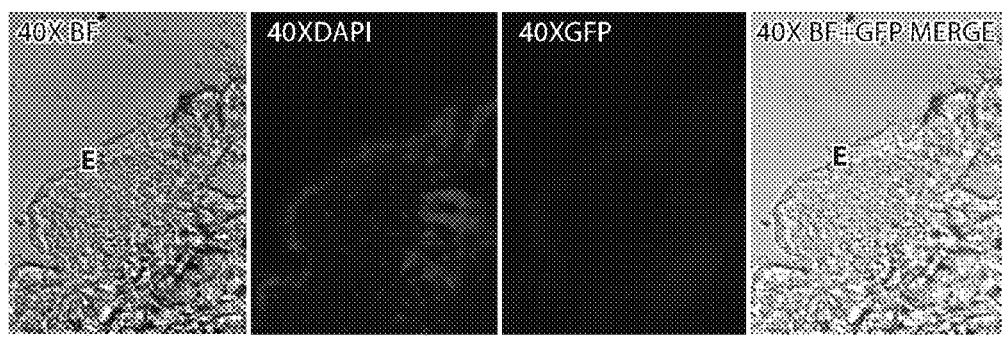
FIG. 13 is a set of photomicrographs showing topical application of POD-GFP to shaved skin in vivo. POD-GFP or control GFP protein was applied to skin for 24 hours.
Figure 13B:
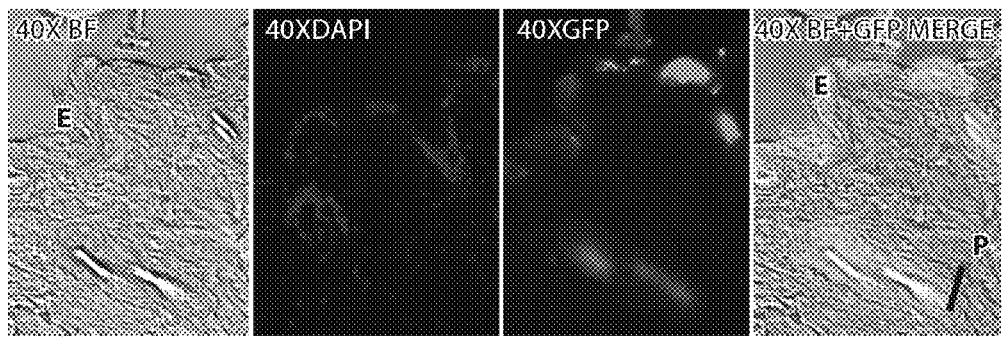

The data show that hair follicles and hair within tissues were auto fluorescent after contact with POD-GFP. Only minimal GFP-fluorescence in contrast was observed with topical application of control GFP (FIG. 13 panel A). The epidermis of skin prepared from mice that received POD-GFP was significantly GFP-positive (FIG. 13 panel B). Uptake appeared punctate and diffuse and was almost exclusively associated with the epidermis and not the deeper layers of the skin (FIG. 13 panel B). Binding observed around the hair follicle could not be definitively separated from auto fluorescence.

These data show that control GFP did not significantly bind to mouse skin, and POD-GFP bound for at least 24 hours, and also was taken up by the epidermis.

Example 12

C-POD, a Cell-Penetrating Peptide, Delivers DNA In Vitro to Quiescent Cells

It is herein shown that C-POD (cysteine-POD) functions to compact a nucleic acid, neutralize its charge and deliver it to mitotic HER cells in vitro. To extend this observation to non-mitotic cells (as is the status of the majority of cells in vivo) A549 cells were serum-starved for 24 hours prior to the addition of a C-POD/pCAGGFP complex, containing a plasmid expressing GFP (pCAGGFP).

Figure 14A:
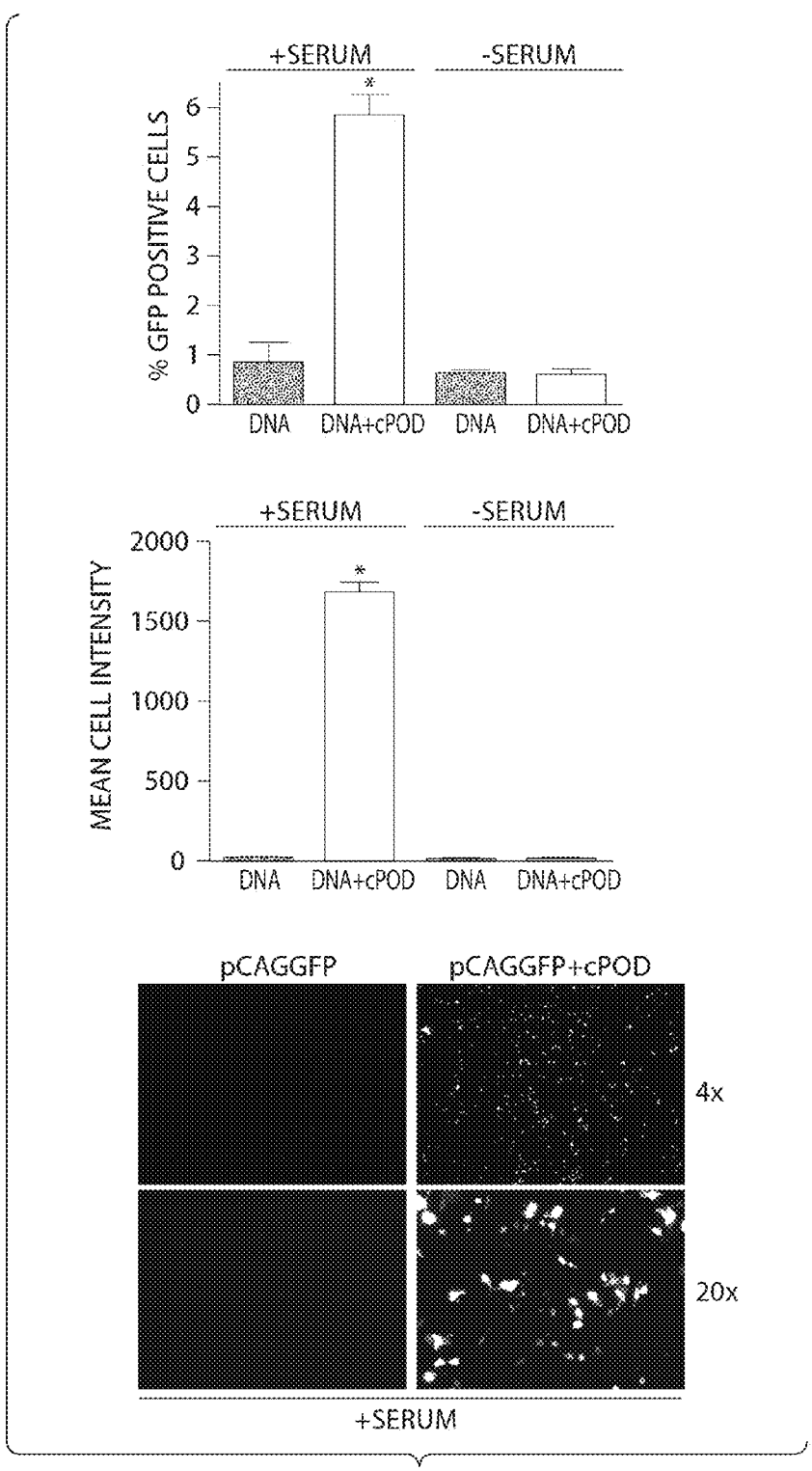
FIG. 14 is a set of bar graphs and photomicrographs showing that the cell penetrating peptide C-POD can deliver genes in vitro but not in vivo to quiescent cells.
Figure 14B:
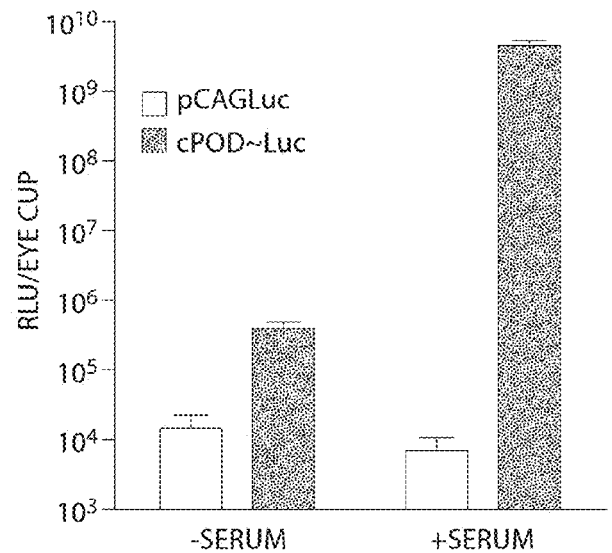
Figure 14C:
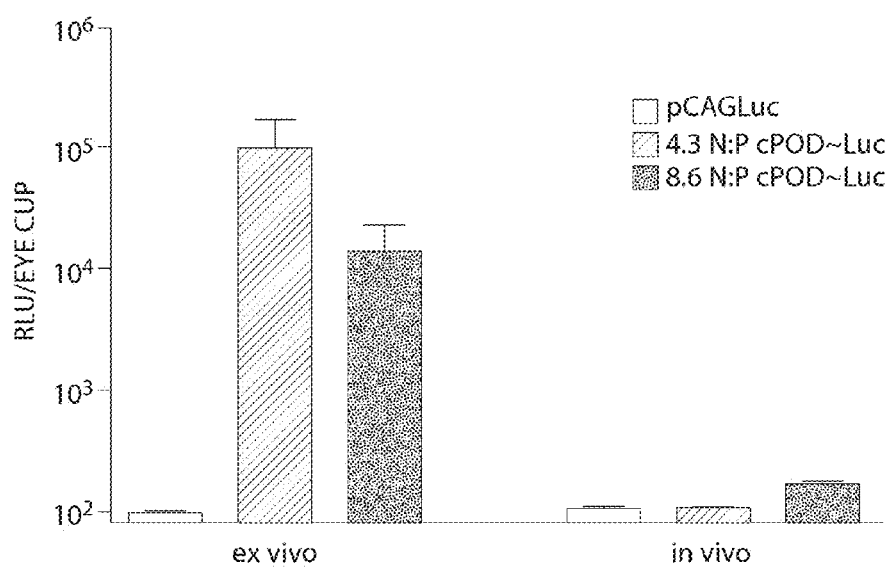
Figure 15A:
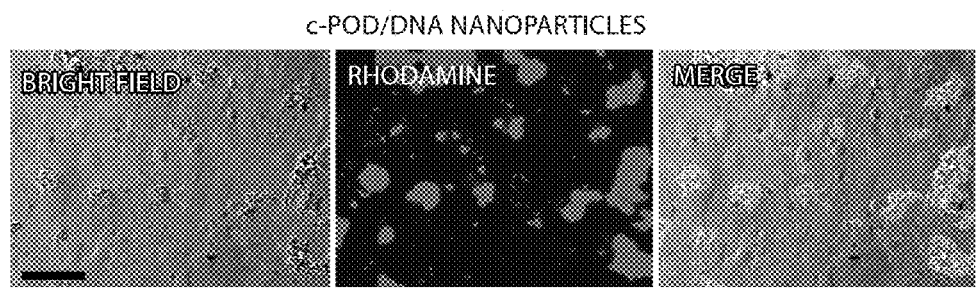
FIG. 15 is a set of photomicrographs and photographs showing that PEGylation of C—POD reduces aggregation while preserving the ability to compact DNA.
Figure 15B:
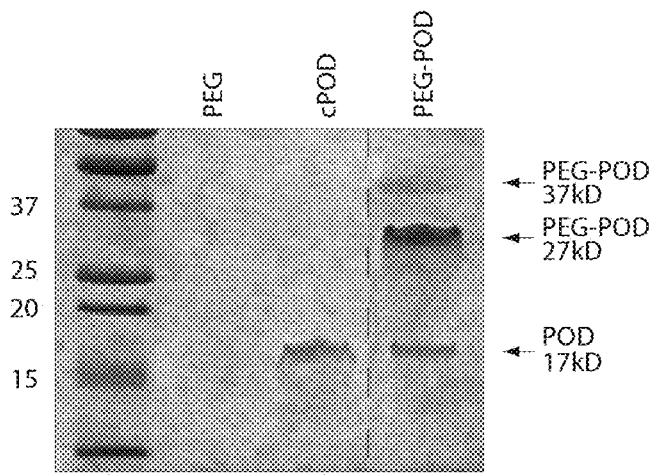
Figure 15C:
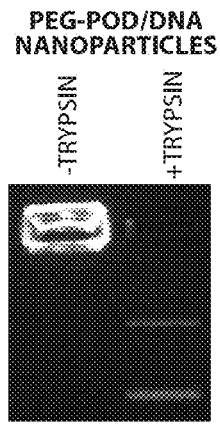
Figure 15D:
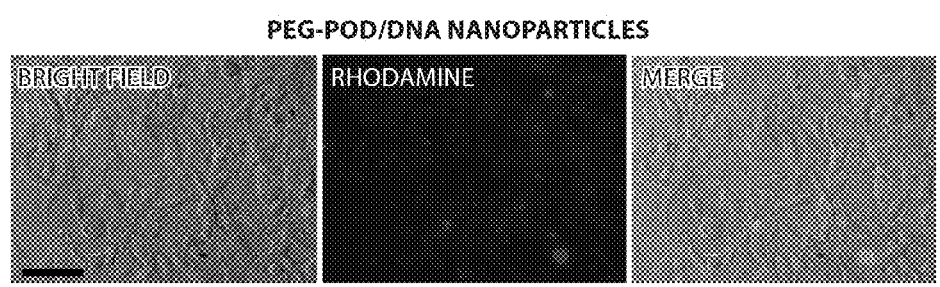

Data show that when A549 cells were undergoing mitosis, 6.05% were GFP-positive, however, <1% of A549 cells were GFP-positive when active mitosis was inhibited ($p<0.0005$) (FIG. 14 panel A). In addition, the mean cellular GFP-intensity was reduced from 1683 to 16.53 ($p<0.0001$) in the presence and absence of serum/mitosis respectively.

To quantify functional recombinant protein levels in transduced cells, A549 cells were transfected with a C-POD/pCA-GLuc complex, containing a plasmid expressing luciferase (pCAGLuc). Results correlated with those observed using GFP, in that C-POD was observed to increase transgene expression in dividing cells compared to that of control plasmid alone by almost six orders of magnitude ($p<0.005$) and compared to that of C-POD in non-dividing cells by four orders of magnitude ($p<0.005$). See FIG. 14 panel B. However, when C-POD was used with non-dividing cells, transgene expression was higher than control cells contacted with DNA only ($p<0.05$).

The data show that C-POD transduces non-dividing cells, but at levels of expression below delectability using GFP. Hence, it was observed that actively mitotic cells were more amenable to transduction by C-POD/DNA complexes than non-mitotic cells, although data do not rule out the possibility that serum itself enhances transduction. To extend these observations to primary cells, C57 eyes were enucleated, the anterior chamber removed, and the RPE/sclera and retina were separated. These explants were incubated ex vivo with C-POD compacted pCAGLuc for 48 hours. Significant transfection was unexpectedly noted in the RPE/sclera for both an N:P ratio of 4.3 ($RLU=1.0\times10^5\pm7.7\times10^4$, $p<0.0001$) and 8.6 ($RLU=1.4\times10^4\pm9.1\times10^3$, $p<0.0001$) (FIG. 14 panel C) but not in the retina. However, when testing was conducted in vivo, no significant luciferase activity ($p>0.05$) was detected above background in either compaction (FIG. 14 panel C). These data show that C-POD compacts and delivers DNA to mitotic cells in culture and to primary cells explants ex vivo.

Example 13

Functionalizing C-Pod by PEGylation Inhibits Particle Aggregation and Preserves DNA Binding A difference between actively dividing and quiescent cells is that during mitosis, the nuclear membrane disintegrates and allows easy access of large molecules such as DNA into the nucleus. The intact nuclear membrane in post mitotic cells in vivo is considered a significant barrier to non-viral gene transfer.

Examples herein tested whether formation of large C-POD/DNA aggregates play a role in inhibiting gene transfer. To examine this hypothesis, rhodamine-labeled plasmid DNA was compacted using C-POD, and this complex was incubated with HER cells for 2 hours in culture.

Data herein show that indeed, even at the level of light-microscopy, large C-POD/DNA aggregates were readily visible (FIG. 15 panel A) and ranged in size from 10-100 µm. To attempt to reduce this level of aggregation, the free sulfhydryl bond on the cysteine of C-POD was functionalized with a 10 kD PEG-maleimide group. Although the predicted molecular weight after synthesis by mass spectroscopy of the C-POD monomer is 3.5 kD, a unique band was observed corresponding to approximately 17 kD on a coomasie stained gel (FIG. 15 panel B), indicating that C-POD forms pentamers in solution. Functionalization of this 17 kD product with 10K PEG generated a gel shift to the expected 27 kD. A minor product was also detected at 37 kD, indicating that an amount of C-POD pentamers were functionalized by two 10 kD PEG molecules. Similar to C-POD [Johnson L N et al. 2008 Mol Ther 16: 107-114 incorporated herein by reference in its entirety], PEGylated POD (PEG-POD) also compacted DNA and retarded DNA migration into an agarose gel, that could be alleviated by pre-digestion of the C-POD peptide with trypsin (FIG. 15 panel C). Unlike C-POD, PEG-POD did not form large aggregates when complexed with DNA and incubated with HER cells for 2 hours (FIG. 15 panel D). Data showed that PEGylation of C-POD prior to electrostatic mixing with plasmid DNA significantly reduces the formation of aggregated products.

Example 14

PEG-Pod Compacts DNA to Form Small, Discrete Nanoparticles

Figure 16:
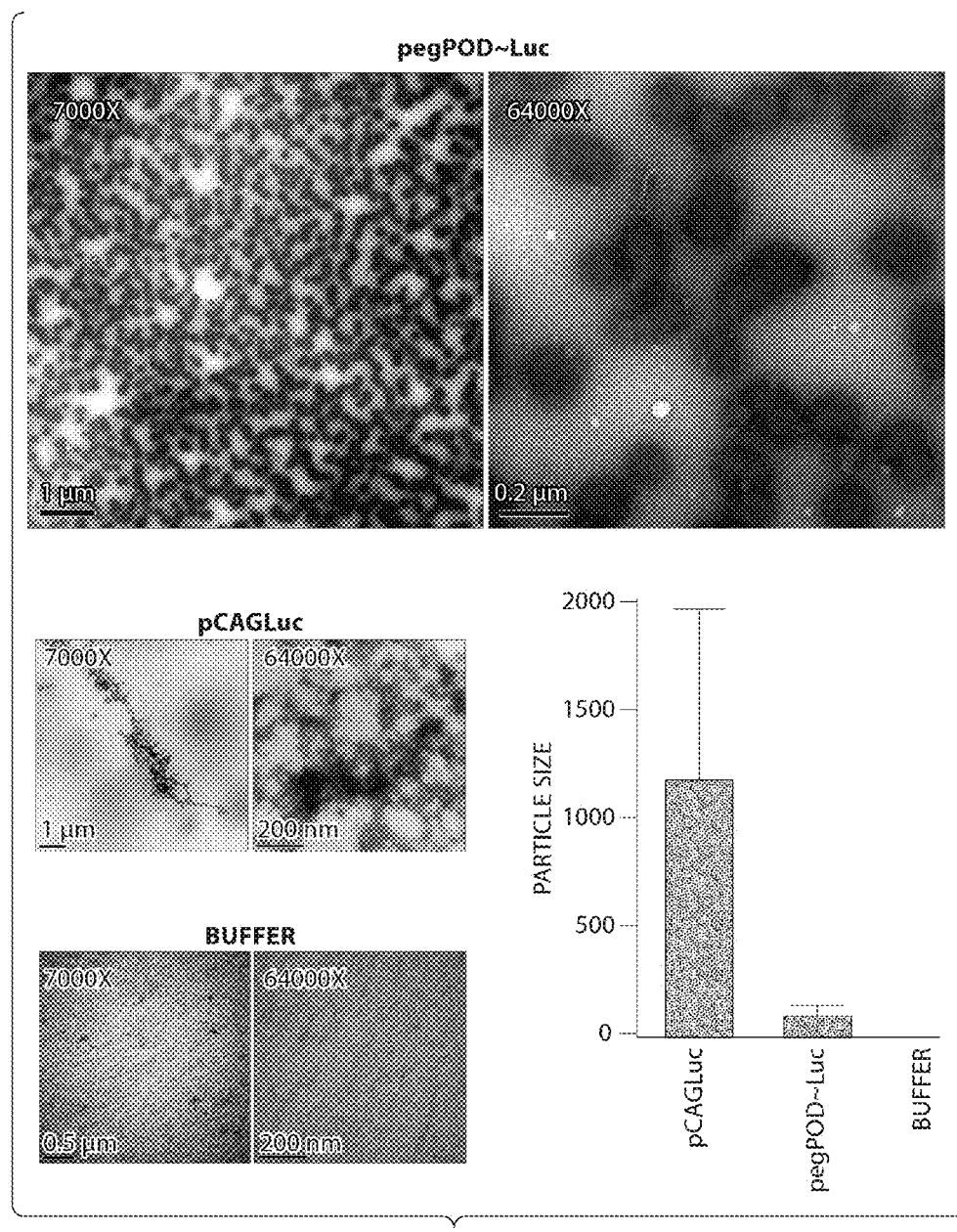
FIG. 16 is a set of photomicrographs and a bar graph that show that PEG-POD compacts DNA to form small, discrete nanoparticles. Transmission electron microscopy revealed that PEG-POD/DNA formed small compact nanoparticles. Addition of each of 5% dextrose buffer, plasmid alone, or compacted plasmid was visualized using uranyl acetate stain. Plasmid DNA formed large irregular aggregates. PEG-POD/DNA nanoparticles were smaller, spherical, and more homogeneous in size.

Closer examination of pPOD~Luc complexes by transmission electron microscopy revealed that the complexes consisted of relatively homogeneous 100-200 nm spherical nanoparticles (FIG. 16). Independent measurement of particle size by diffuse light scattering (DLS) determined a size range of 136 nm±27.2 nm. In contrast, the controls, i.e. buffer or uncompacted DNA alone, were determined to be 1.6 nm±0 nm and 1221 nM±753.4 nm respectively by DLS. The large standard deviation for DNA (which has a large gyration radius) is expected as DLS is primarily accurate for spherical particles between 2 nm-2000 nm.

Example 15

Figure 17:
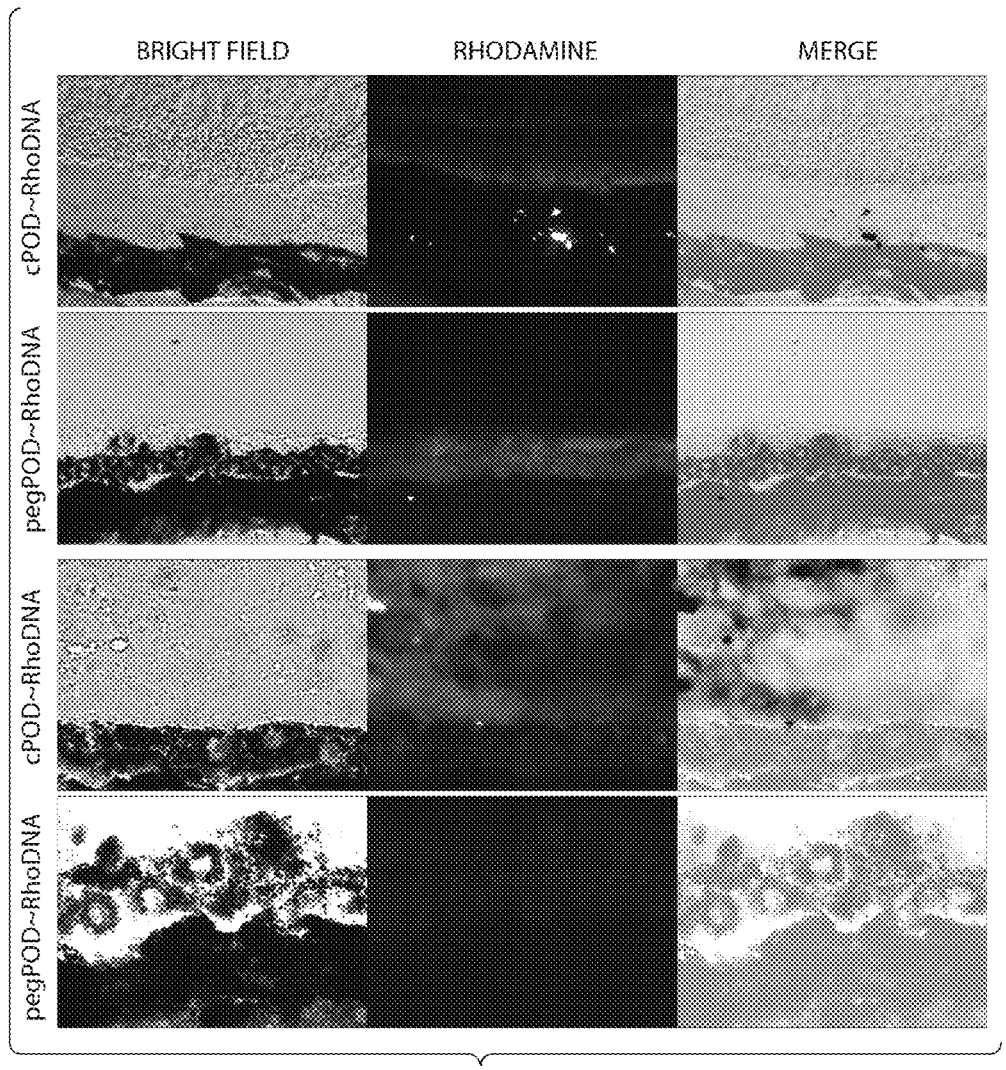
FIG. 17 is a set of photomicrographs that show that PEG-POD nanoparticles have different localization in vivo compared to C-POD compacted DNA. Rhodamine-labeled DNA compacted with PEG-POD (PEG-POD~RhoDNA) or C-POD (C-POD~RhoDNA) was injected subretinally and harvested after two hours. PEG-POD~RhoDNA particles appeared as punctuate and diffuse, staining within the RPE cell layer. C-POD~RhoDNA appeared to bind the surface of the RPE cells only and be isolated to the subretinal space.

PEG-POD~RhoDNA and cPOD~RhoDNA Particles have Different Localization in Tissues In Vivo To determine whether PEG-POD/DNA complexes penetrated tissues more efficiently than C-POD/DNA complexes, nanoparticles of rhodamine-labeled DNA (100 ng) compacted with PEG-POD (PEG-POD~RhoDNA) or C-POD (C-POD~RhoDNA) were injected into the subretinal space of 8 week old C57 male mice and eyes were harvested after 2 hours. In contrast to C-POD~RhoDNA particles that remained in the subretinal space. In contrast, PEG-POD~RhoDNA particles appeared as punctate staining within the retinal pigment epithelium (FIG. 17, second row images and fourth row images compared to first row images and third row images).

Example 16

PEG-POD~Luc Nanoparticles Transfect Ocular Tissue In Vivo

Figure 18A:
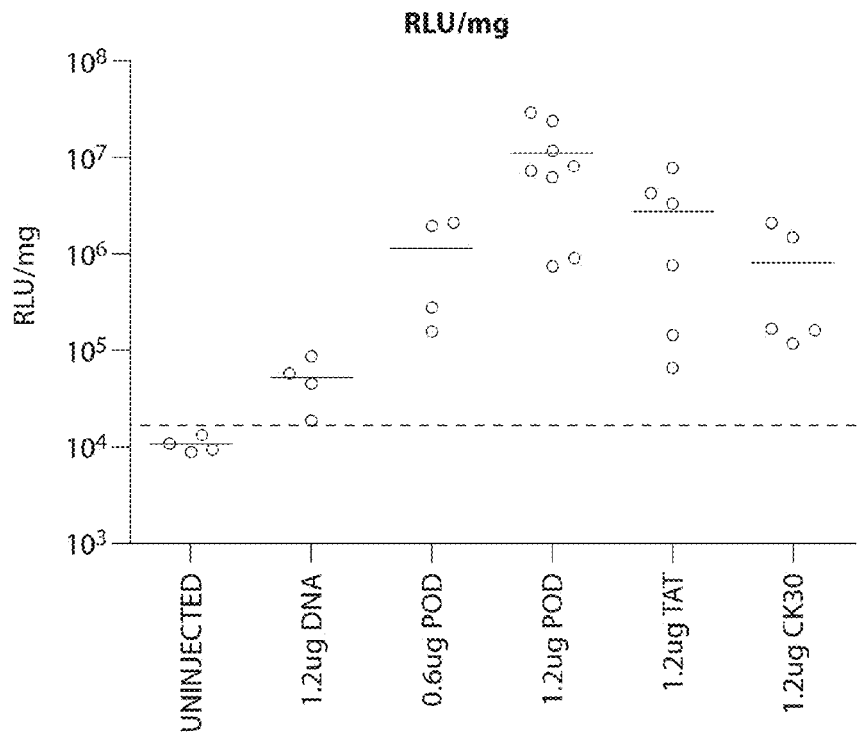
FIG. 18 is a set of bar graphs showing that PEG-POD~Luc nanoparticles transfect ocular tissue in vivo after subretinal injection more efficiently than other CPPs and are dose-dependent. Samples were analyzed at 48 hours after injection and 1.2 µg DNA PEG-POD~Luc nanoparticles were injected into the subretinal space of adult BALB/C mice and exhibited expression levels significantly higher than 1.2 µg DNA alone ($p<0.0001$) or uninjected controls ($p<0.0001$). When only 0.6 µg of PEG-POD nanoparticles were injected in the same volume, there was still a significant increase in expression over uninjected controls ($p<0.001$) and 1.2 µg naked DNA ($p<0.05$) was observed, and a significant reduction compared to 1.2 µg of PEG-POD nanoparticles ($p<0.05$). PEG-TAT~Luc was significantly increased compared to 1.2 µg DNA alone ($p<0.05$) and uninjected controls ($p<0.005$). PEG-CK30~Luc showed the lowest expression of the three cell penetrating peptides but was still significantly increased above 1.2 µg DNA alone ($p<0.05$) and uninjected controls ($p<0.005$). PEG-POD nanoparticles showed a significant increase in transfection compared to PEG-CK30 (p<0.005). PEG-TAT nanoparticles were not significantly different from those formed by either PEG-POD or PEG-CK30 (p>0.05). These results show that all three cell penetrating peptides significantly increase peptide transfection in vivo compared to DNA alone.
Figure 18B:
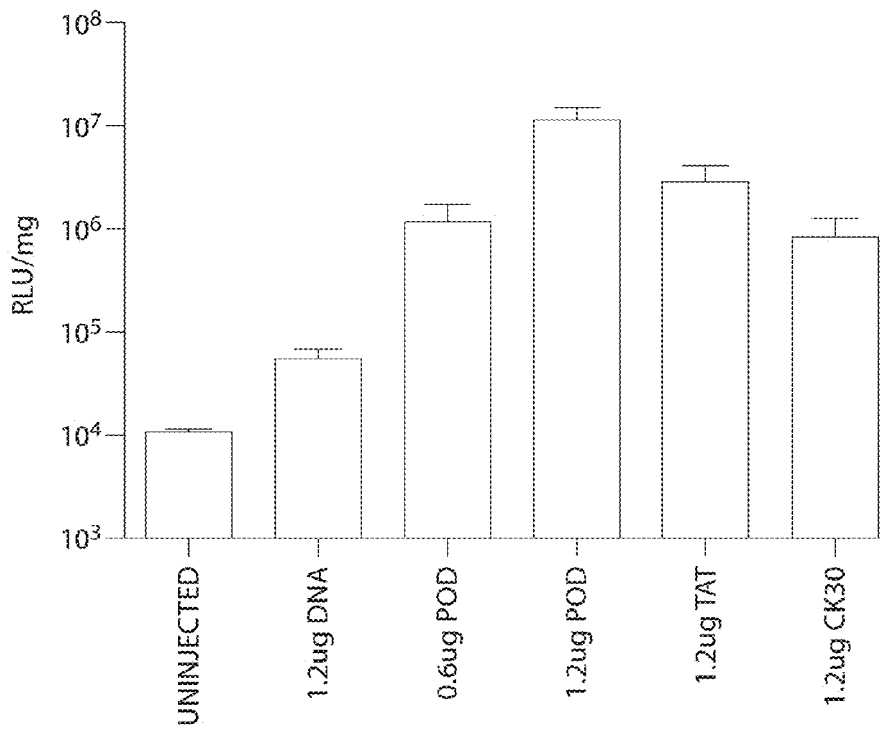
Figure 18C:
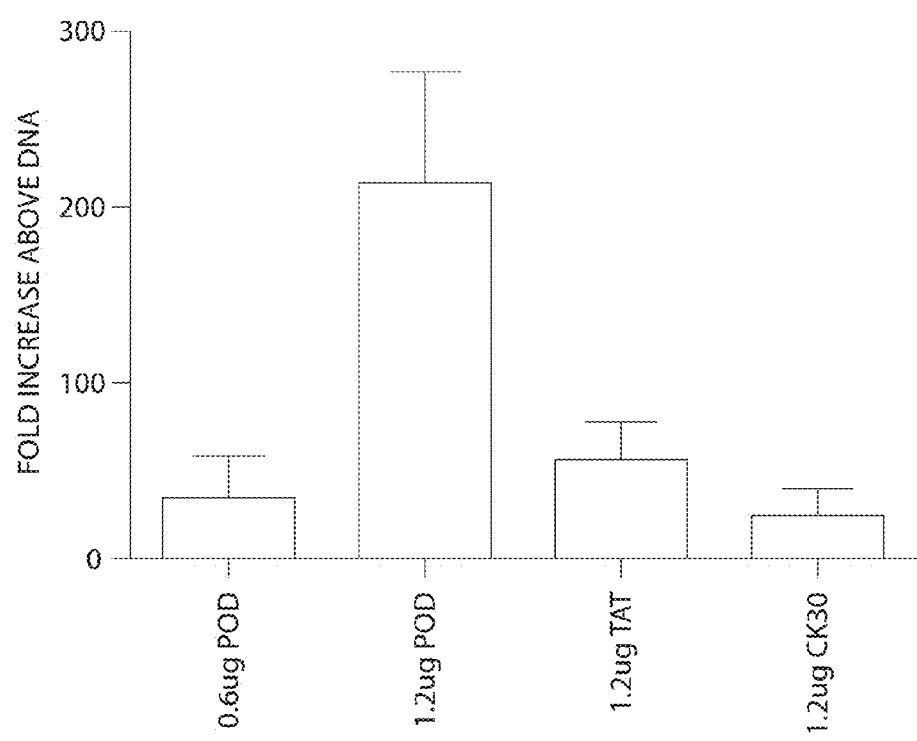

PEG-POD~Luc nanoparticles were injected into the subretinal space of adult (6-7 weeks) BALB/C mice and eyes were harvested after 48 hours to assay for luciferase activity. To normalize the RLU, the concentration of protein harvested and the RLU per mg protein were plotted and quantified (FIG. 18 panels A and B). Transfection using PEG-POD nanoparticles containing 1.2 µg DNA ($1.51 \times 10^7 \pm 3.83 \times 10^6$ RLU/mg) exhibited expression levels several orders of magnitude higher than 1.2 µg DNA alone ($5.54 \times 10^4 \pm 1.47 \times 10^4$ RLU/mg, $p<0.0001$) or uninjected controls ($1.09 \times 10^4 \pm 1.04 \times 10^3$ RLU/mg, $p<0.0001$). DNA alone expression was several-fold greater than uninjected controls as well ($p<0.05$). When only 0.6 µg of PEG-POD nanoparticles were injected in the same volume, there was still a several orders of magnitude greater expression ($1.17 \times 10^6 \pm 5.48 \times 10^5$ RLU/mg) than observed in uninjected controls ($p<0.001$) and 1.2 µg naked DNA ($p<0.05$). FIG. 18 panel C. However there was a significant reduction in mean luminescence of 9.8 fold compared to injections of 1.2 µg of PEG-POD nanoparticles ($p<0.05$). These data show that PEG-POD nanoparticles efficiently deliver trangenes in vivo compared to DNA alone and that this property is dose dependant at the concentrations tested.

Recombinant luciferase (Promega) was used to create a standard curve for the RLU values ($R^2=0.9999$). It was calculated that expression of luciferase following contact with naked, pCAGLuc plasmid was an amount of 1.915±0.5449 pg/mg, and 0.6 µg PEG-POD~Luc resulted in an amount of 43.23±20.26 pg/mg, and 1.2 µg PEG-POD~Luc resulted in an amount of 425.2±141.7 pg/mg luciferase protein.

Example 17

PEG-POD Increases Tranfection Compared to Other Pegylated Cell Penetrating Peptides Efficacy of other established cell penetrating peptides including TAT, CK30, and a 30-mer polylysine were tested, in addition to PEG-POD. CK30 is described in U.S. patent application Ser. No. 10/656,192 filed Sep. 8, 2003, Cooper et al.

These peptides were each PEGylated using the same protocol to produce PEG-TAT and PEG-CK30. PEG-TAT has been shown to compact DNA in cell culture [Ignatovich I A et al. 2003 J Biol Chem 278: 42625-42636; Rudolph C et al. 2003 J Biol Chem 278: 11411-11418]. Various PEG-TAT: DNA ratios were used and compaction was assessed by gel electrophoresis. PEG-TAT was observed to fully compact plasmid DNA at 1.8 nMole peptide:2 µg DNA, the same ratio used for PEG-POD. The PEG-TAT nanoparticles were made using the same protocol as PEG-POD nanoparticles. PEG-CK30 nanoparticles have been made previously and documented to show efficacy in vivo [Ziady A G et al. 2003 Mol Ther 8: 936-947; Farjo R et al. 2006 PLoS ONE 1: e38; Liu G et al. 2003 J Biol Chem 278: 32578-32586] and so the ratio and protocol outlined in those studies were followed [Ziady A G et al. 2003 Mol Ther 8: 936-947], yielding fully compacted DNA by gel electrophoresis.

BALB/C mice were injected subretinally with 1.2 µg of either PEG-TAT~Luc or PEG-CK30~Luc and the eyes were harvested 48 hours later (FIG. 18 panel A). PEG-TAT~Luc showed high levels of expression ($2.849 \times 10^6 \pm 1.298 \times 10^6$) and which was significantly increased compared to 1.2 µg DNA alone ($p<0.05$) and uninjected controls ($p<0.005$). Of the PEG-CK30~Luc injections, one was observed to be less than the uninjected control mean RLU/mg+3 standard deviations (FIG. 18 panel A, dotted line). This was the only injection, of either naked DNA or nanoparticle DNA, that did not express increased luciferase, and so this injection was not counted in the final analysis of the data (FIG. 18 panel B). PEG-CK30~Luc was observed to have the lowest expression of the three cell penetrating peptides ($8.379 \times 10^5 \pm 4.310 \times 10^5$), significantly greater than that observed with 1.2 µg DNA alone ($p<0.05$) and uninjected controls ($p<0.005$). PEG-POD nanoparticles showed a significant 16.4 fold increase in the mean compared to PEG-CK30 ($p<0.005$). PEG-TAT nanopaticles were not significantly different from those formed by either PEG-POD or PEG-CK30 ($p>0.05$). These results show that the three cell penetrating peptides significantly increased peptide transfection in vivo compared to DNA alone. PEG-POD increased expression of plasmid DNA 215±63 fold, PEG-TAT 56.52±21.33, and PEG-CK30 24.73±15.30 compared to the same amount of DNA injected alone (FIG. 18 panel C). Further, PEG-POD caused the most efficient transduction by subretinal injection of these peptides.

Example 18

Cell Penetrating Peptide Nanoparticles Transfect Retinal Pigment Epithelium (RPE)

Figure 19:
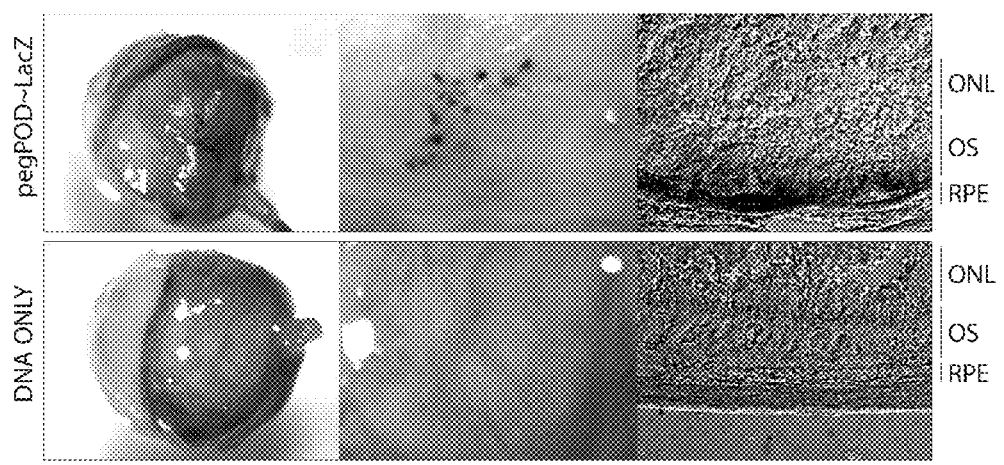
FIG. 19 is a set of photographs showing PEG-POD, PEG-TAT and PEG-CK30 compacted LacZ nanoparticles transfect RPE cells. To examine 3-galactosidase expression, 1.2 μg each of PEG-POD~LacZ, PEG-TAT~LacZ, or PEG-CK30~LacZ nanoparticles was injected subretinally in BALB/CJ mice and expression assayed 48 hours after injection. Analysis showed punctate patches of staining in the RPE, visible through the sclera and choroids that correlated with the relative luciferase levels seen with each peptide. Sections show that expression was localized in the RPE. No β-galactosidase expression was detected in any of the control eyes. A representative buffer injected eye is shown.

To determine tissue localization of expression, nanoparticles were made using each of the PEGylated cell penetrating peptides containing plasmids expressing β-galactosidase (pCAGLacZ), and an amount of 1.2 µg was injected subretinally into BALB/C mice. Eyes were harvested and stained for β-galactosidase activity at 48 hours after injection (FIG. 19). The observed relative amounts of β-galactosidase activity correlated with that of the previously observed luciferase values (FIG. 18), and it was observed that expression was localized to the RPE cell layer. While the three cell penetrating peptides were able to transduce the RPE, the most robust staining was seen by PEG-POD~LacZ and the least by PEG-CK30~LacZ. Control eyes were either uninjected or injected with the same amount of uncompacted DNA, luciferase nanoparticles, PEG-POD alone, or buffer. No β-galactosidase stain was detected in any of the control eyes.

Example 19

PEG-POD Protects Plasmid DNA from DNase I Digestion

Serum nuclease activity significantly decreases the half-life of plasmid DNA. DNA injected intravenously into mice is degraded within 10 minutes [Kawabata K et al. 1995 Pharm Res 12: 825], therefore protection from degradation is an important property to engineer genes to be successfully delivered in vivo by intravenous injection. Deoxyribonuclease I (DNase I) is an endonuclease found in human serum and many tissues in the body [Love J et al. 1979 J Bio Chem 254: 12588]. A neutralizing antibody specific for DNase I was added to human serum, completely inhibited nuclease activity, indicating that serum nuclease activity is due to DNase I [Takeshita H et al. 2004 Clinical Chemistry 50: 446-448].

Figure 20A:
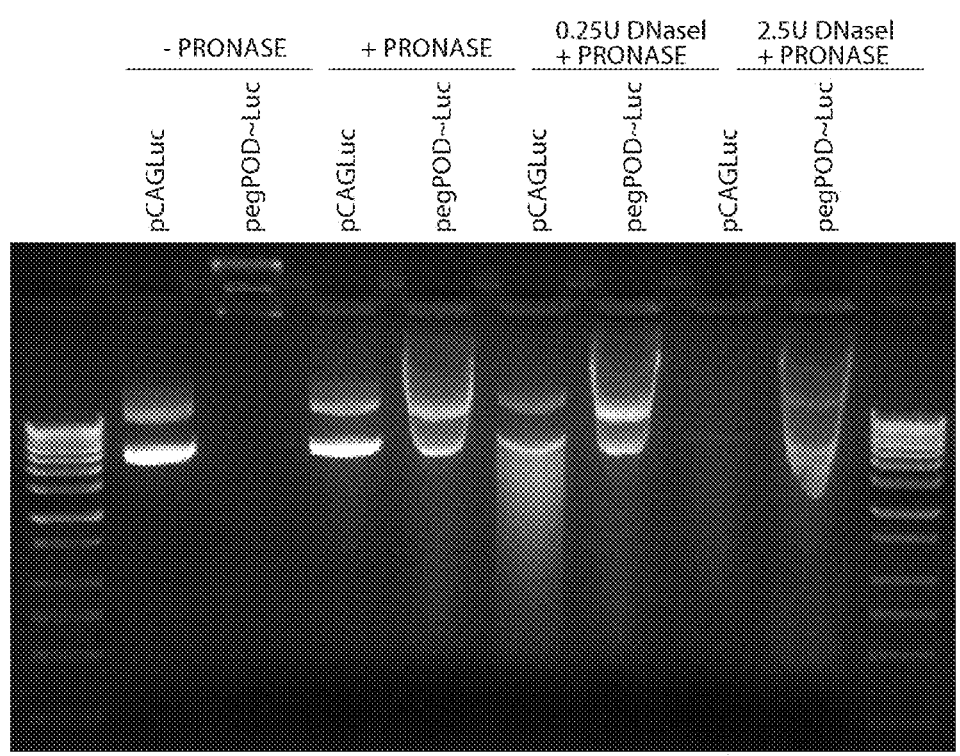
FIG. 20 is a photograph of an electrophoretogram and a bar graph, showing that compaction of DNA confers protection against DNase and increased transfection in vivo during intravenous injection.
Figure 20B:
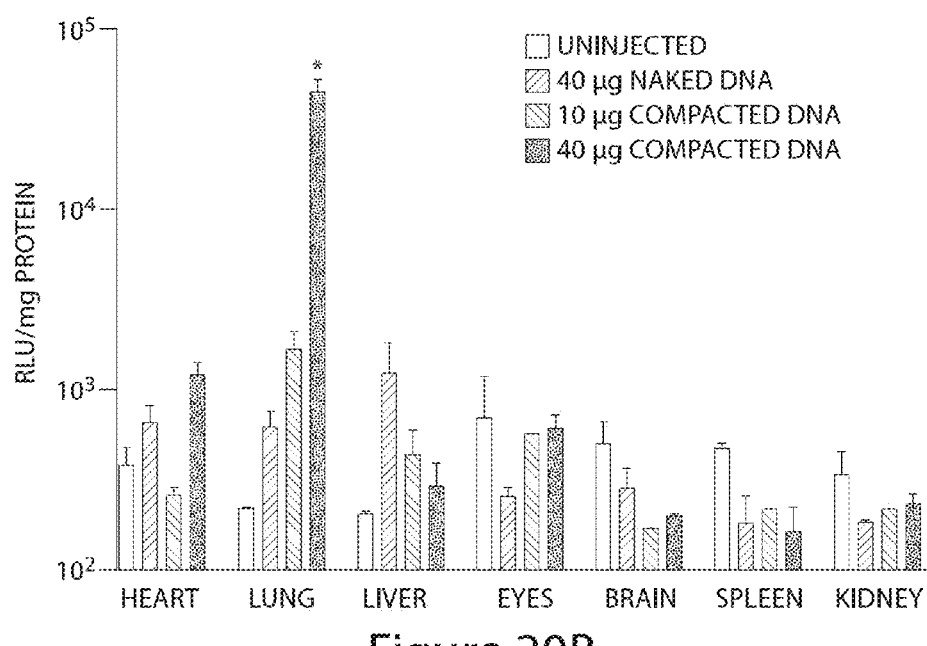

Serum and pancreatic DNase I exhibit essentially the same characteristics [Love J et al. 1979 J Bio Chem 254: 12588] and since the enzyme is easily purified from the pancreas, pancreatic DNAse I was here used to test the potential serum stability of the PEGylated POD/DNA nanoparticles (FIG. 20 panel A). In the absence of pronase, pCAGLuc plasmid, migrated into the gel while the pPOD~Luc nanoparticles remained compacted within the well of the gel. Subsequent to a 10 minute incubation with pronase, both pCAGLuc and pPOD~Luc DNA migrated into the gel. To test DNAse I resistance, each of the DNA and the nanoparticles were incubated for 15 minutes with DNase I followed by a 10-minute incubation with pronase, which allowed visualization of the compacted DNA by degrading pPOD. After the addition of 0.25 U DNase 1, pCAGLuc was observed to show signs of initial degradation, while pPOD~Luc remained intact. At a higher concentration of 2.5 U DNase I, the pCAGLuc plasmid was completely degraded and was no longer detectable on the gel, whereas pPOD~Luc had only minor degradation. These data show that p-POD/DNA complexes were protected from DNase I degradation.

Example 20 pPOD~Luc has Higher Tranfection Efficiency than pCAGLuc in the Lung

Since pPOD protects DNA from DNase I digestion, transfection following intravenous delivery in vivo was examined. BALB/C mice were injected with 150 µL of 5% dextrose buffer containing either 40 µg pCAGLuc or 40 µg pPOD~Luc (FIG. 17 panel B). pCAGLuc, 40 µg, was delivered intravenously, and observed levels of luciferase in the lung were determined to be 623.7±1.39.1 RLU/mg. In contrast, the luciferase levels of pPOD~Luc, 40 µg delivered intravenously, were observed to be orders of magnitude greater, $4.445 \times 10^4 \pm 8082$ RLU/mg ($p<0.0001$). See FIG. 20 panel B. Delivery of 10 µg pPOD~Luc also resulted in higher levels of luciferase activity, 1670±430.5 RLU/mg ($p<0.05$). These data show that increasing the quantity of pPOD~Luc injected from 10 µg to 40 µg resulted in a significant increase in luciferase expression ($p<0.0001$), and that naked plasmid alone did not significantly express luciferase in the lung above that observed with uninjected mice ($p>0.05$).

Example 21 pPOD~Luc does not Cause Toxicity as Determined by Functional Analysis

Figure 21A:
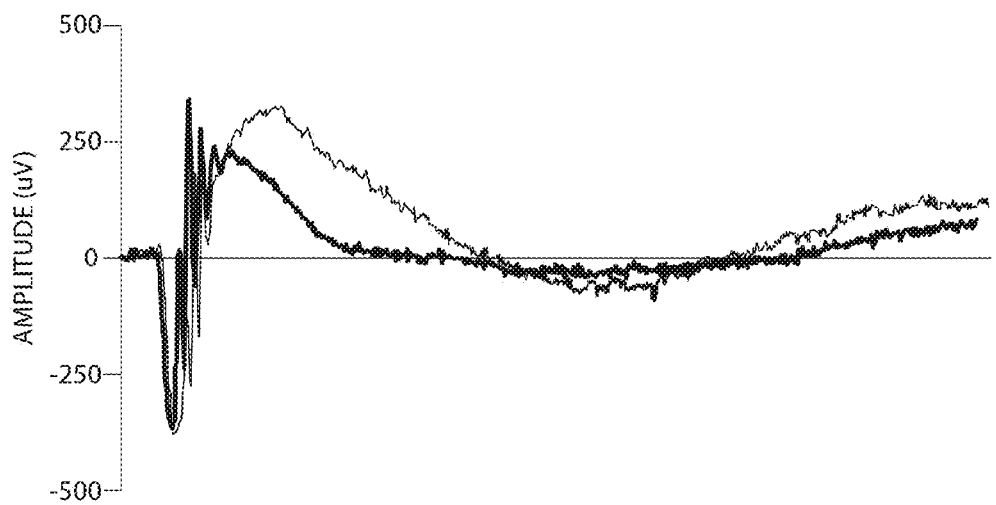
FIG. 21 is a line graph and a bar graph testing by functional analysis toxicity of PEG-POD nanoparticles. Mice were injected in the subretinal space with either 0.7 μg pPOD~Luc in 1 μl (n=4) or 1 μl 5% dextrose (n=4), the same buffer as the nanoparticles, in adult (6-8 week) C57 males. After 48-hours, ERGs were performed at two log intensities. Both the PEG-POD~Luc and mock injected eyes had normal waves with a defined. A and B-waves.
Figure 21B:
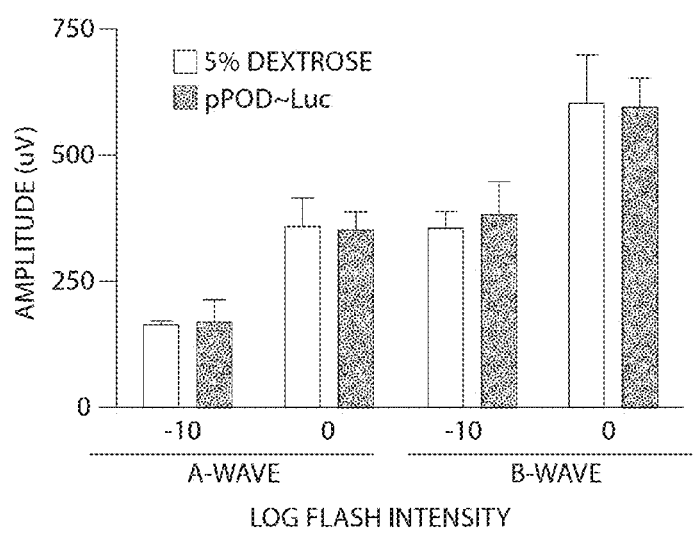
Figure 22A:
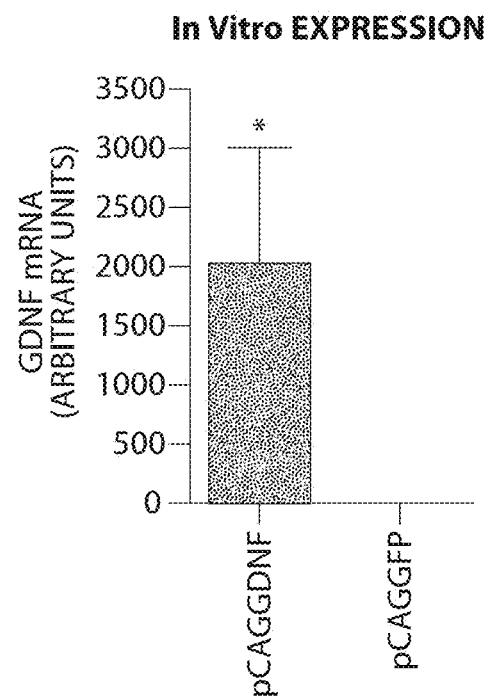
FIG. 22 is a set of bar graphs and photomicrographs showing that pCAGGDNF expresses detectable GDNF mRNA and PEG-POD compacted pCAGGDNF and forms GDNF expressing nanoparticles.
Figure 22B:
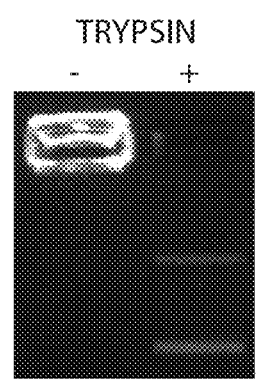
Figure 22C:
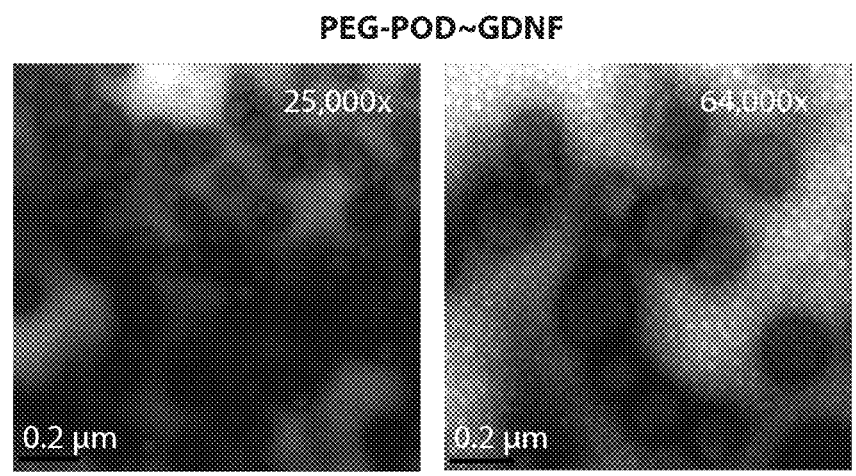
Figure 22D:
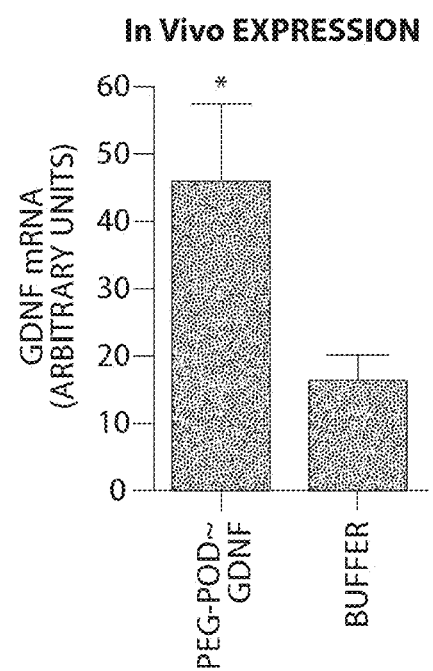
Figure 23A:
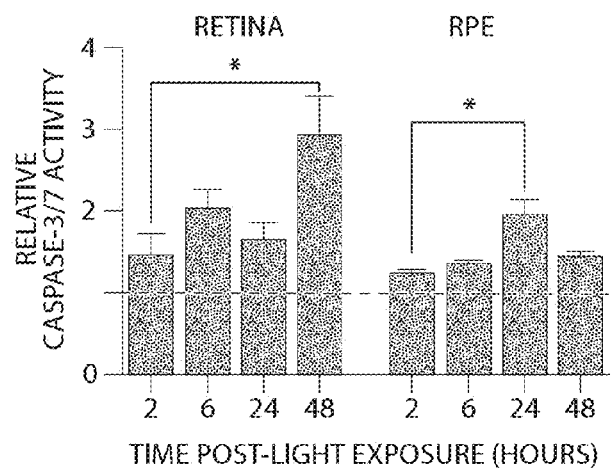
FIG. 23 panels A, B and C are a set of line graphs and bar graphs showing that bright blue light induces caspase-3/7 activation and that retinal degeneration is modulated by subretinal injection.
Figure 23B:
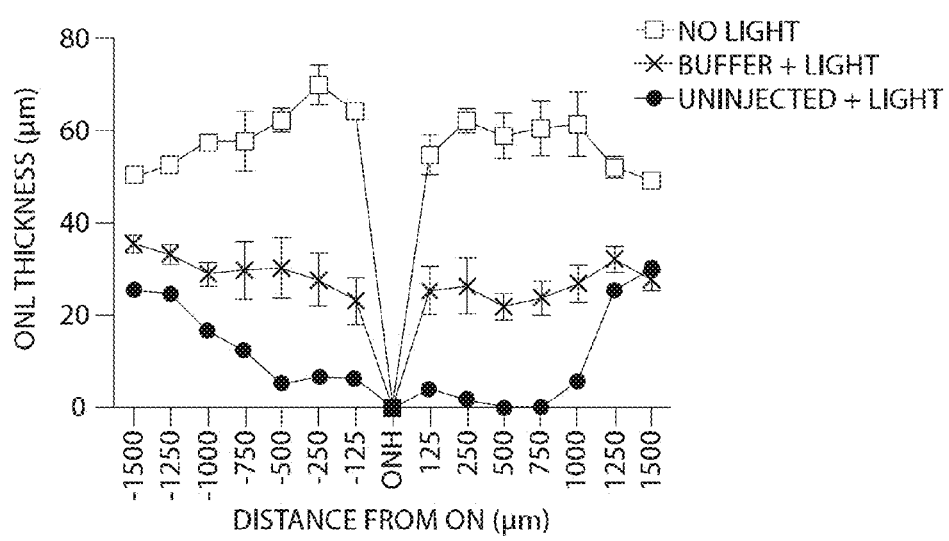
Figure 23C:
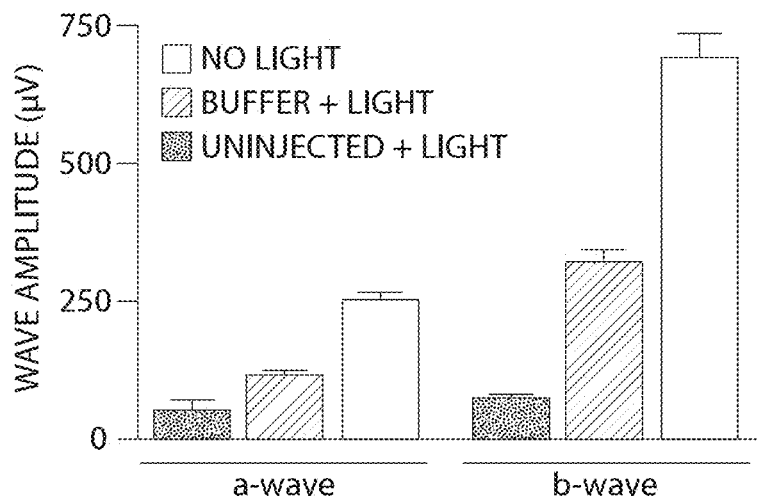
Figure 23D:
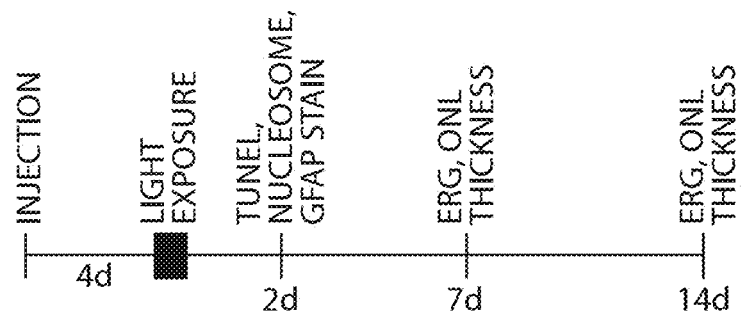

To examine pCAG~Luc nanoparticles toxicity in vivo, subjects were injected either with 0.7 µg pPOD~Luc in 1 µl (n=4) or with 5% dextrose (n=4), the same buffer as the nanoparticles, into the subretinal space, using adult (6-8 week) C57 males. After 48 hours, electroretinograms (ERGs) were recorded at two different light intensities. Both the pPOD~Luc and mock injected eyes were observed to have normal ERGs, with defined A and B-waves (representative examples at −0 Log Light Intensity are shown in FIG. 21 panel A). The waves were analyzed for A and B-wave amplitude and plotted by Log Light Intensity (FIG. 21 panel B). No significant difference was observed in data from subjects receiving these injections for these test condition (p>0.05).

Example 22

GDNF Plasmid

Previous Examples herein show that PEG-POD compacts DNA into discrete and homogeneous nanoparticles and that these particles transduce a variety of tissues in vivo, including the RPE. See also Read et al., Gene Med 12: 86-96 (2009), hereby incorporated herein by reference in its entirety.

To examine the potency of these nanoparticles as a carrier for a therapeutic agent in a model of retinal degeneration, a gene encoding GDNF was cloned operably linked to a chicken beta actin promoter (pCAGGDNF). A plasmid carrying the GDNF gene is commercially available (Addgene Inc., Cambridge, Mass.).

The GDNF trangene was cloned from pGDNF3a into pCAGEN using a NotI/XhoI to generate pCAGGDNF. Amino acid sequence for C-POD, CGGG(ARKKAAKA)$_4$ (SEQ ID NO: 11), was synthesized at Tufts University Peptide Synthesis Core Facility (Boston, Mass.) and purified by high performance liquid chromatography (HPLC).

Example 23

Preparation PEG-POD Nanoparticles Containing GDNF

Peptides were prepared and PEGylated, and DNA was compacted into the nanoparticles as previously shown in Examples herein, by diluting the plasmid in water to 0.2 μg/μL and adding dropwise to PEG-POD with a final ratio 1.8 nMole peptide:2 μg DNA (0.466 pmole pCAGLuc or 0.396 pmole pCAGGDNF).

Data analyses for the Examples below were performed using Prism Software 4 (GraphPad Software, Inc.). Significance testing on the differences between ONL thickness and ONL/INL ratio (FIGS. 26-27) was performed using a paired Students t-test. Other statistical tests were performed using an unpaired Students t-test. Outliers were determined using the Quartile or Fourth-Spread method [Devore J L. 2000 Probability and Statistics for Engineering and the Sciences. 5 ed, BCP Company: Pacific Grove, Calif.]. Data are presented as the mean±standard error.

Example 24

PEG-POD Forms GDNF-Expressing Nanoparticles

Expression of rat GDNF mRNA was determined in human embryonic retinoblasts (HER) by transfection in vitro (FIG. 22 panel A). Human embryonic retinoblasts (HER) 911 cells [Fallaux F J, et al. 1996 Hum Gene Ther. 7(2): 215-222] were grown in Dulbecco's modified Eagle's media (DMEM) supplemented with 10% fetal bovine serum (FBS; Invitrogen, Carlsbad, Calif.). Plasmids were transfected in triplicate into HER 911 cells using Lipofectamine 2000 (Invitrogen). Cells were harvested after 48 hours by removing media, adding RNA Stat-60 (Tel-Test Inc., Friendswood, Tex.), and were stored at −80° C.

PEG-POD~GDNF (1.2 μg) was injected into the subretinal space of 6-8 week old BALB/cJ and tissue was harvested after 48 hours. The posterior eye cup was isolated and was homogenized using Stat-60 reagent and was stored at −80° C. RNA was isolated using chloroform extraction and precipitated using isopropanol. DNase treatment was performed using Turbo DNase enzyme solution. Samples were prepared using a iScript One-Step RT-PCR Kit for Probes (Bio-Rad) on an iQ-5 Thermal Cycler (Biorad), probed using rat GDNF primer/probe (Assay #Rn00569510_m1, Taq Man Gene Expression Assay, Applied Biosystems) and normalized to human GAPDH primer/probe (Assay #4332649, Taq Man Gene Expression Assay, Applied Biosystems) in 911 cells and mouse β-actin primer/probe (Assay #4352663, Taq Man Gene Expression Assay, Applied Biosystems) in mouse tissue.

The pCAGGDNF had been compacted using PEG-POD (PEG-POD~GDNF) resulted in retarded electrophoretic migration of the plasmid DNA, which was relieved by trypsin-mediated digestion of the POD peptide (FIG. 22 panel B). PEG-POD~GDNF was observed to form discrete spherical nanoparticles as examined by transmission electron microscopy (TEM) (FIG. 22 panel C). Analysis of the TEM images showed that the mean particle diameter was 175.9±28.6 nm.

PEG-POD~GDNF nanoparticles injected into the subretinal space of adult mice caused a detectable level of rat-specific GDNF transcript observed relative to control buffer-injected retinas 48 hours post-injection (p<0.05) (FIG. 22 panel D). Subjects were injected with nanoparticles into the subretinal space and dark-adapted for four days. Eyes were dilated in the dark and left for 2 minutes immediately prior to light exposure. Mice were unrestrained and were exposed to 8,500-11,000 lux (Light Meter, Lux/FC 840020, Sper Scientific) of 450 nm saturated blue light (Bili Blue, Interiectric, Warren, Pa.) for four hours. Following light exposure, mice were maintained in darkness and were sacrificed, and eyes were assayed for retinal degeneration.

Example 25

Bright Blue Light Activates Caspase-3/7 and Induces Retinal Degeneration that is Modulated by Subretinal Injection The mechanism of light damage is a function of intensity and type of light. To characterize the specific mechanism of photoreceptor degeneration induced by the methods herein, caspase-3 mediated apoptosis was determined. Caspase-3 mediated apoptosis has been shown to be involved in retinal degeneration models [Liu C, et al. 1999 J. Neurosci. 19(12): 4778-4785; Yoshizawa K, et al. 2002 Graefes Arch Clin Exp Opthalmol. 240(3): 214-219; Wu J, et al. 2002 Invest Opthalmol Vis Sci. 43(10): 3349-3354; Chang C J, et al. 2005 Ophthalmic Res. 37(4): 202-213; Perche O, et al. 2007 Invest Opthalmol Vis Sci. 48(6): 2753-2739].

Mice were exposed to four hours of bright blue light following dark adaptation. To analyze caspase-3/7 activation in mouse retina, light exposed eyes were harvested at each of two, six, 24 and 48-hours after light treatment/exposure. The retina was separated from the RPE/choroid/sclera, and caspase-3/7 activity was quantified relative to activity for control non-light treated retinas (FIG. 23 panel A).

Caspase 3/7 activity was measured using a Caspase-Glo assay (Promega; Madison, Wis.) [Liu D, et al. 2004 J Biol. Chem. 279(46): 48434-48442]. Cytosolic extracts were obtained from retina and RPE tissue harvested as a function of time, and prepared by homogenization in 50 mM Tris-HCl, pH 8.0, 150 mM with protease inhibitors and centrifuged 15 min, 2,000 rpm, at 4° C. The protein concentration was measured using Quick-Start Bradford Dye Reagent (Bio-Rad) and concentration was adjusted to 0.15 mg/mL and stored at −80° C. An equal volume of Caspase reagent and protein extract were mixed and incubated for 1 hour at room temperature. Luminescence was measured using a Glomax-20/20 luminometer (Promega).

It was observed that a 2.9-fold increase in caspase-3/7 activity occurred in the retina 48 hours post-light exposure (p<0.05), compared to control eyes not exposed to light, and a 1.9-fold increase in caspase-3/7 activity in the RPE/choroid/sclera 24-hours post-light exposure (p<0.05).

Subretinal injection alone was observed to partially rescue light-induced damage [Faktorovich E G, et al. 1992 J. Neurosci. 12(9): 3554-3567]. Thus, prior to assaying extent of effect of injection of PEG-POD~GDNF nanoparticles, the level of rescue resulting from a sham subretinal injection was here determined.

Mice were injected in the subretinal space with a 5% dextrose solution and 4 days later, and were exposed to bright blue light for 4 hours. Eyes were harvested, sectioned, and nuclei were stained with DAPI. The extent of photoreceptor degeneration was evaluated by measuring the thickness of the outer nuclear layer (ONL), with decreased ONL demonstrating photoreceptor degeneration. Degeneration in the light damage model occurs predominantly in the central retina and at higher levels in the superior hemisphere of the eye [Wu J, et al. 2002 Invest Opthalmol Vis Sci. 43(10): 3349-3354; Wu J, et al. 1999 Graefes Arch Clin Exp Opthalmol. 237(10): 855-860].

Eyecups were sectioned for histological analysis along the vertical meridian in a section bisecting the optic nerve head (ONH). Histological analysis was performed by harvesting eyes 7 and 10 days after light exposure and fixing the eyes for 24 hours in 4% PFA. The eyes were then dehydrated, embedded in OCT, and sectioned into 14 μm sections which were collected along the vertical meridian. Sections that approximately bisected the optic nerve were DAPI stained, coverslipped, and photographed. Images were analyzed using QCapture Pro 5.0 (QImaging, British Columbia, Canada). Images were spatially calibrated and manual measurements of the thickness of the ONL and INL nuclear layers were performed. Measurements of ONL and INL thickness were taken at distances (μm) of each of 125, 250, 500, 750, 1000, 1250, and 1500 μm from the optic nerve. The average thickness of the sections was measured including the thickness of the ONL and INL, respectively, and the ratio of ONL/INL was determined by the quotient of the average thickness.

It was observed that the ONL had lost photoreceptor nuclei following light treatment. A significant reduction in photoreceptor loss was observed in eyes receiving a subretinal injection of buffer (5% dextrose) prior to light exposure (FIG. 23 panel B). Subretinal injection of 5% dextrose was performed as a control in subsequent rescue testing in Examples herein, and the dextrose solution was routinely used to suspend the nanoparticle formulations.

To measure any potential change in retinal function, electroretinograph measurements were recorded in buffer-injected mice seven days after light exposure (FIG. 23 panel C) and compared with those of uninjected light treated mice.

Electroretinography was performed on the eyes as described herein. Mice were dark adapted for one week following light exposure, and were anaesthetized. Pupils were dilated with 1% Tropicamide (Akorn, Inc., Lake Forest, Ill.), and scotopic electroretinograms, ERGs, were recorded at a flash intensity of 1 decibel (dB) using contact lens electrodes and the UTAS system with BigShot ganzfeld (LKC Technologies, Inc, Gaithersburg, Md.). Five flashes for each tested sample were averaged and smoothed using the UTAS software.

It was observed that subretinal injection resulted in partial rescue measured by ERG. A 2.3-fold and 4.5-fold increase was observed in the amplitudes of the a-waves and b-waves, respectively, compared to results for uninjected light-treated animals. The observation of rescue in eyes was consistent with histological data obtained herein. Both the a-wave and b-wave amplitudes were substantially impaired compared to those amplitudes observed for non-light treated eyes (p<0.0001).

To test whether PEG-POD~GDNF nanoparticles would cause significantly greater levels of rescue than sham subretinal injection, the same light exposure regimen was employed and eyes were harvested at different time-points for measurement of rescue (FIG. 23 panel D).

Example 26

PEG-POD~GDNF Reduces Light-Induced Apoptosis

Examples herein show that PEG-POD~GDNF inhibits the apoptotic cascade and remediates photoreceptor cell death. Eyes of six to eight week old BALB/cJ mice were injected into the subretinal space of the superior hemisphere with either PEG-POD~GDNF, PEG-POD~Lux, or buffer control. Eyes were harvested and sectioned 48 hours post-light treatment. Eye sections bisecting the ONH were stained using TUNEL staining (FIG. 24 panel A). TUNEL-positive nuclei in both the superior and inferior hemispheres were counted (FIG. 24 panel B).

To detect and localize apoptosis, TUNEL staining was performed on injected eyes 48-hours after light exposure. The eyes were fixed for 24 hours in 4% PFA, dehydrated, embedded in OCT, and 14 μm sections were collected along the vertical meridian. TUNEL stain was performed using an In Situ Cell Death Detection Kit, TMR Red (Roche Applied Science, Indianapolis, Ind.). Sections were counterstained with 0.1 μg/ml DAPI and were coverslipped. Quantification was performed for TUNEL positive photoreceptor nuclei in a vertical section through the optic nerve in both the superior and inferior hemisphere of each eye. The presence of nucleosomes released into the cytoplasm was assessed using a Cell Death Detection ELISA (Roche Applied Science, Indianapolis, Ind.). Retina were removed and homogenized in 400 μL Isolation Buffer using a VWR PowerMax AHS 200 homogenizer and incubated for 30 minutes at room temperature. After centrifuging (20,000 g) the material for 10 minutes, the supernatant was obtained and was diluted 1:200 in isolation buffer and used according to the manufacturer's protocol.

It was observed that eyes injected with PEG-POD~GDNF nanoparticles had a significant decrease in the number of TUNEL-positive nuclei in the ONL in the superior hemisphere (31.00±8.5 nuclei/section) compared to eyes injected with PEG-POD~Lux (241.2±77.6 nuclei/section, p<0.005) or buffer (197.9±39.7, p<0.0005). A significant decrease in TUNEL-positive nuclei was also observed in the inferior hemisphere of eyes injected with PEG-POD~GDNF (33.60±7.3 nuclei/section) compared to eyes injected with PEG-POD~Lux (117.6±41.0 nuclei/section, p<0.05) or buffer (107.7±39.9 nuclei/section, p<0.05).

A significant decrease in the level of apoptosis was observed with TUNEL staining, however only in the areas most significantly affected by light exposure (the vertical meridian at the ONH). A more global evaluation of tissue apoptosis by evaluating cell death throughout the retina was performed using a nucleosome release assay.

Retinal tissue was harvested 48 hours after light exposure and the level of apoptosis evaluated by nucleosome release ELISA (FIG. 24 panel C). Histone associated DNA fragments were observed present as a result of internucleosomal genomic DNA degradation during apoptosis. Increased cell apoptosis was observed as an increase in absorbance, due to antibody detection of histone bound DNA. Eyes injected with PEG-POD~GDNF had 2.3-fold lower absorbance than PEG-POD~Lux-injected eyes (p<0.05), 3.9-fold lower absorbance than was observed with control eyes injected with buffer (p<0.05), and 7.4-fold lower absorbance than control light treated eyes that were not injected (p<0.0005).

These data show that injection of PEG-POD~GDNF nanoparticles resulted in significantly decreased apoptosis in eyes that had undergone injury of exposure to light. To determine whether photoreceptor cells were similarly affected, preservation of photoreceptor cells was examined.

Example 27

GDNF Nanoparticles Prevent Photoreceptor Cell Loss

Examples herein show that PEG-POD~GDNF nanoparticles significantly reduced apoptosis. Number of photoreceptor nuclei was determined by measuring thickness of the ONL. Eyes were injected with either PEG-POD~GDNF, PEG-POD~Lux or a buffer control, and were analyzed by sectioning along the vertical meridian and staining with DAPI at a section bisecting the optic nerve head (ONH; FIG. 23 panel B). ONL and inner nuclear layer (INL) thickness were measured at 250 μm intervals along the length of the retina. The effect of these injections was observed at 7 and 14 days post-light treatment (FIG. 25).

Light exposed eyes injected with PEG-POD~GDNF showed a significant increase in ONL thickness both in inferior and superior hemispheres. PEG-POD~GDNF injected eyes showed a significant increase in ONL thickness 7 days post-light treatment compared to eyes injected with PEG-POD~Lux (p<0.01) or buffer (p<0.001) (FIG. 25 panel A). At 14 days post-light treatment, the PEG-POD~GDNF injected eyes showed greater ONL thickness than eyes injected with buffer (p<0.0001) (FIG. 25 panel B). The thickness of the retina 14 days post-light treatment of eyes injected with PEG-POD~GDNF or with PEG-POD~Lux was not significantly different (p>0.05). However, the difference in the ONL thickness of the superior hemisphere (p<0.005), i.e. the site of the subretinal injection, between eyes injected with PEG-POD~GDNF and PEG-POD~Lux, was significant: PEG-POD~GDNF injected eyes were observed to have a greater ONL thickness after light exposure.

Figure 26A:
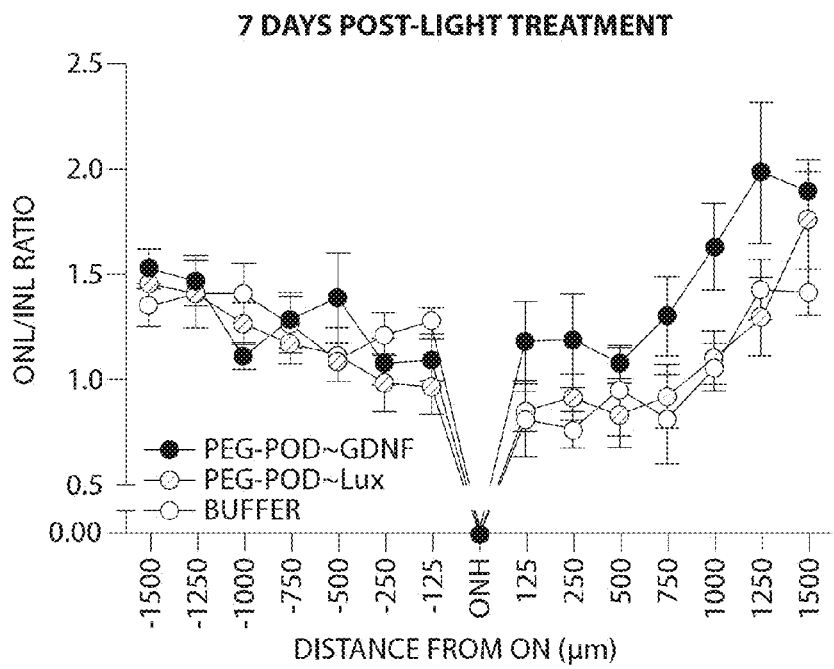
FIG. 26 is a set of line graphs showing that subretinal injection of PEG-POD~GDNF increased the ratio of ONL thickness to INL thickness (ONL/INL ratio) for eyes 7 days and 14 days after light treatment. The line graphs show ONL/INL ratio (ordinate) as a function of distance from the ONH (μm, abscissa) of eyes injected with PEG-POD~GDNF, PEG-POD~Lux or buffer.
Figure 26B:
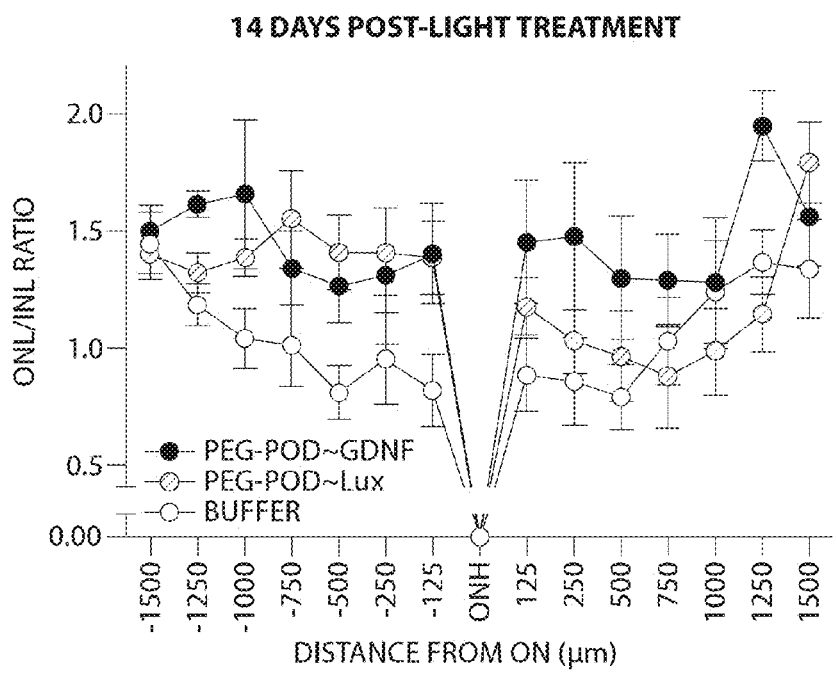

Additional differences in ONL thickness were observed 7 days post-light treatment for PEG-POD~Lux injected eyes and buffer injected eyes (p<0.05). However, a significant difference in the overall ONL thickness was observed at 14 days post light treatment, between PEG-POD~Lux injected eyes and buffer-injected eyes (p<0.05). This difference in thickness between PEG-POD~Lux injected eyes and buffer-injected eyes was not observed when measuring the ONL thickness of the superior hemisphere alone (p>0.05). Because TUNEL staining was observed mostly in the photoreceptor nuclei and not in the INL, the thickness of the INL was also measured and used as an internal parameter/control by calculating the ratio of the thickness of the ONL compared to the thickness of the INL (FIG. 26 panels A and B). Similar patterns of rescue and/or preservation of photoreceptor cells were observed by analyzing the data using the ONL/INL ratio at 7 and 14 days post-light treatment.

Figure 27A:
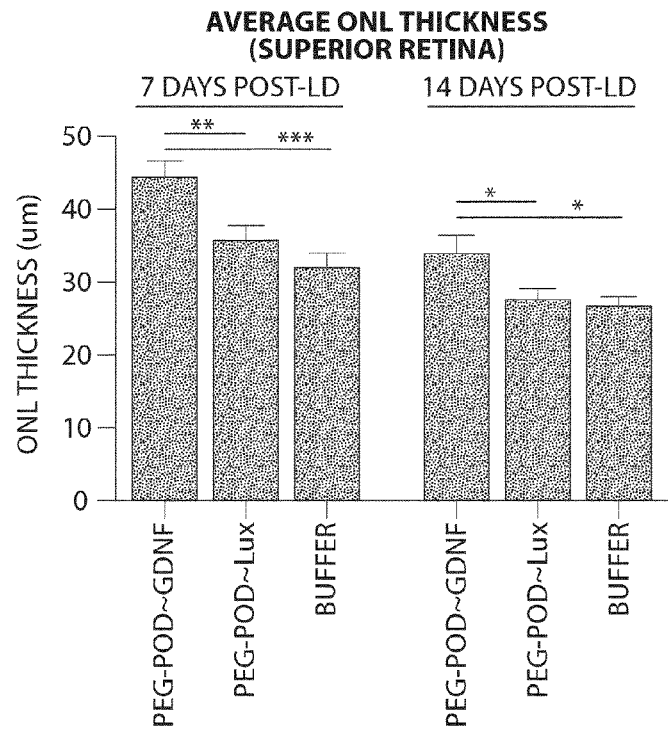
FIG. 27 is a set of bar graphs showing that injection of PEG-POD~GDNF into eyes increases the average thickness of the ONL and ratio of the thickness of ONL to the thickness of the INL.
Figure 27B:
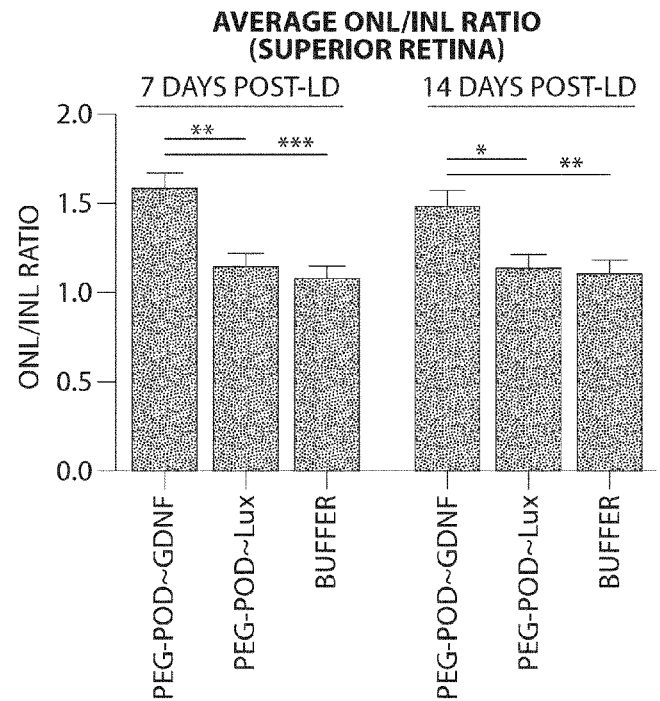

The average thickness of the ONL of the superior retina was calculated at a distance of 250-1500 μM from the optic nerve, proximal to the site of injection (FIG. 27). At 7 days post-light treatment, the average ONL thickness of PEG-POD~GDNF injected retinas (44.37±2.154 μm) was 24.5% greater than that of PEG-POD~Lux injected retinas (35.63±2.198 μm, p<0.01) and 39.3% greater than that of eyes injected with buffer alone (31.86±2.184 μm, p<0.0005) (FIG. 27 panel A). At 14 days post-light treatment, PEG-POD~GDNF-injected retinas had 23.6% and 27.7% greater average ONL thickness (33.83±2.696 μm) than PEG-POD~Lux-injected eyes (27.36±1.812 μm, p<0.05) and buffer injected eyes (26.50±1.549 μm, p<0.05), respectively. There was little difference between the average ONL thickness of PEG-POD~Lux injected eyes and buffer injected eyes at either 7 or 14 days post-light treatment (p>0.05).

Data were analyzed also by calculating the ratio of ONL thickness to INL thickness (FIG. 27 panel B). The ratio of ONL/INL thickness at 7 days was 38.5% and 47.3% greater in eyes injected with PEG-POD~GDNF compared to control eyes injected with PEG-POD~Lux (p<0.001), and to control eyes injected with buffer (p<0.0005), respectively. At 14 days, the ONL/INL thickness ratio for PEG-POD~GDNF-injected eyes was 30.4% and 33.9% greater than PEG-POD~Lux injected eyes (p<0.05) and buffer-injected eyes (p<0.005), respectively.

Significant decrease in the overall ONL thickness between 7 and 14 days post-light treatment was observed in eyes injected with each of PEG-POD~GDNF (p<0.005), PEG-POD~Lux (p<0.005), and in buffer injected eyes (p<0.05). Degeneration was shown to be inhibited following PEG-POD~GDNF injection, and that subretinal injection of PEG-POD~GDNF promotes photoreceptor survival.

Example 28

Injection of GDNF Nanoparticles Leads to Functional Rescue

To determine whether methods and compositions herein caused functional rescue of retina, ERG was calculated for eyes injected 7 days after light treatment. The amplitude of both the a- and b-waves was measured and was compared for injections of PEG-POD~GDNF, and control injections of PEG-POD~Lux or buffer. (FIG. 28 panels A and B).

PEG-POD~GDNF injected eyes were observed to have 39% and 32% increases in amplitude in the a-wave compared to PEG-POD~Lux (p<0.05) injected eyes and buffer control injected eyes (p<0.05), respectively. The b-wave amplitude for PEG-POD~GDNF injected eyes was increased 31% compared to PEG-POD~Lux injected eyes (p<0.05) and 27% compared to buffer injected eyes (p<0.05). No significant difference was observed in a- or b-wave-amplitudes between PEG-POD~Lux injected eyes and buffer injected eyes (p>0.05). No or only small differences were observed between PEG-POD~Lux injected eyes and buffer injected eyes (FIG. 28) wave-amplitude data, similar to data in previous Examples herein that showed no differences in relative ONL thicknesses for these treatments (FIG. 27).

Additional ERG measurements of eyes injected with PEG-POD~GDNF or buffer at each of 10 and 14 days after light exposure (FIG. 29) showed increased ERG amplitudes for PEG-POD~GDNF injected eyes compared to buffer injected eyes 10 days after light exposure. The PEG-POD~GDNF injection caused 49% increase in the a-wave (p<0.005) and 29% increase in the b-wave (p<0.05), respectively, compared to the buffer injections. No significant a- or b-wave-amplitudes differences were observed between the two injections at 14 days after light treatment (p>0.05).

Example 29

Injection of PEG-POD~GDNF Nanoparticles Activates Müller Cells

Injection of GDNF protein into the subretinal space of rd/rd mice increases glial fibrillary acidic protein (GFAP) immunoreactivity in Müller glia [Frasson M, et al. 1999 *Invest Opthalmol Vis Sci.* 40(11): 2724-2734]. GDNF stimulates neurotrophic factor release from Müller cells and act via an indirect neuroprotective pathway through activation of Müller glia [Harada T, et al. 2002 *J. Neurosci.* 22(21): 9228-9236; Hauck S M, et al. 2006 *Mol Cell Biol.* 26(7): 2746-2757].

To investigate the effect of PEG-POD~GDNF on Müller cell activation in the light damage model herein, light-exposed eyes were injected with PEG-POD~GDNF, PEG-POD~Lux, or buffer control. Eyes not exposed to light were used as a further control. Eyes were injected, harvested 48-hours after light treatment or control, and were fixed for 24 hours in 4% PFA, dehydrated in 15% and 30% sucrose solution, respectively, overnight and embedded in Tissue-Tek optimal cutting temperature compound (Sakura Finetek, Torrance, Calif.). Frozen sections, 14 µm, were collected along the vertical meridian and were each incubated for 1 hour in 6% (w:v) normal goat serum (Jackson ImmunoResearch, West Grove, Pa.), and 0.25% (v:v) Triton X-100 (Fischer Bio-reagents, Fair Lawn, N.J.) in PBS. Solutions were discarded and the sections were incubated 2.5 hours in a solution of rabbit anti-GFAP antibody (Novus Biologicals, Littleton, Colo.) diluted 1:500 in the goat serum solution. The solutions were discarded and sections were washed three times in PBS, and were incubated with CY3-goat anti-rabbit secondary antibody (Jackson ImmunoResearch, West Grove, Pa.) diluted 1:500 in the goat serum solution. Sections were analyzed by light and fluorescent microscopy using an Olympus IX51 microsope with differential interference contrast and appropriate fluorescent filters. Images were obtained using a Retiga 2000R FAST camera and QCapture Pro 5.0 imaging software (QImaging, British Columbia, Canada), and were analyzed with removal of auto-fluorescence by consistent manipulation of the levels in Photoshop CS and by measuring the signal in the lower retina, excluding the inner limiting membrane, in Image J image processing [Abramoff M D, et al. 2004 *Biophotonics Intl.* 11(7): 36-42].

Increased expression of GFAP in the Müller cell body of the inner retina following light treatment was observed relative to control eyes not exposed to light, for each injection condition (FIG. 30 panel A, arrows). Quantification of GFAP signal in the inner retina showed significantly increased GFAP in PEG-POD~GDNF injected eyes relative to control eyes treated with buffer (p<0.05) (FIG. 30 panel A). The level of GDNF expression in cells transduced by the PEG-POD~GDNF nanoparticles may consequently have been sufficient to activate Müller glia in the retina. These data show that GDNF mediated rescue in a light induced model of retinal degeneration.

What is claimed is:

1. A method for delivery of a therapeutic agent to a cell or a tissue or for transduction into the cell or cells of the tissue, the method comprising:
providing the therapeutic agent conjugated or linked to at least one copy of an amino acid sequence comprising: SEQ ID NO:1, SEQ ID NO:2, SEQ ID NO: 12, SEQ ID NO: 13, SEQ ID NO: 14, SEQ ID NO: 15, SEQ ID NO: 16, or SEQ ID NO: 17, wherein the amino acid sequence is effective for delivery to the cell or transduction into the cell of the therapeutic agent; and contacting the cell or tissue with the therapeutic agent conjugated or linked to the amino acid sequence, wherein the therapeutic agent is delivered to or transduced into the cell or the cells of the tissue, wherein the cell or the tissue is ocular.

2. The method according to claim 1, wherein the cell or the tissue is in culture.

3. The method according to claim 1, wherein the cell or the tissue is in vivo.

4. A method for delivery of a therapeutic agent to a cell or a tissue or for transduction into the cell or cells of the tissue, the method comprising:
providing the therapeutic agent conjugated or linked to at least one copy of an amino acid sequence selected from the group consisting of: SEQ ID NO:1, SEQ ID NO:2, SEQ ID NO: 12, SEQ ID NO: 13, SEQ ID NO: 14, SEQ ID NO: 15, SEQ ID NO: 16, or SEQ ID NO: 17, wherein the amino acid sequence is effective for delivery to the cell or transduction into the cell of the therapeutic agent;
formulating the conjugated or linked therapeutic agent as a medicament for diagnosing, prognosing, or treating a condition in a mammalian subject; and
contacting the cell or tissue with the therapeutic agent conjugated or linked to the amino acid sequence, wherein the therapeutic agent is delivered to or transduced into the cell or the cells of the tissue, wherein contacting the cell or the tissue comprises administering the therapeutic agent conjugated or linked to the amino acid sequence to the subject by an intravitreal route.

5. A method for delivery of a therapeutic agent into cells or tissue of an eye, the method comprising:
providing a PEGylated peptide for overall delivery (POD) comprising at least one copy of an amino acid sequence comprising: SEQ ID NO:1, SEQ ID NO:2, SEQ ID NO: 12, SEQ ID NO: 13, SEQ ID NO: 14, SEQ ID NO: 15, SEQ ID NO: 16, or SEQ ID NO: 17, wherein the amino acid sequence is effective for delivery to or transduction into the cells of the therapeutic agent;

mixing the PEGylated POD and the therapeutic agent, thereby forming a PEGylated POD-therapeutic agent complex; and contacting the cells or tissue with the complex, wherein the therapeutic agent is transduced into the cells or the tissue of the eye; and, observing reduced retinal degeneration in the cells or the tissue of the eye in comparison to uncontacted cells.

6. The method according to claim 5, wherein contacting the cells or the tissue of the eye comprises contacting in vivo.

7. The method according to claim 5, wherein contacting the cells or the tissue of the eye comprises contacting in vitro.

8. The method according to claim 5, wherein prior to mixing, the method further comprises preparing a cDNA nucleotide sequence encoding the therapeutic agent amino acid sequence.

9. The method according to claim 8, wherein the cDNA nucleotide sequence encodes a protein that is a neurotrophic factor selected from a group consisting of glial cell line-derived neurotrophic Factor (GDNF).

10. The method according to claim 5, wherein observing reduced retinal degeneration further comprises determining eye function by electroretinography.

\* \* \* \* \*

SEQUENCE LISTING

```
<160> NUMBER OF SEQ ID NOS: 17

<210> SEQ ID NO 1
<211> LENGTH: 35
<212> TYPE: PRT
<213> ORGANISM: Artificial Sequence
<220> FEATURE:
<223> OTHER INFORMATION: The peptide was designed and synthesized

<400> SEQUENCE: 1

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala
        35

<210> SEQ ID NO 2
<211> LENGTH: 11
<212> TYPE: PRT
<213> ORGANISM: Artificial Sequence
<220> FEATURE:
<223> OTHER INFORMATION: The peptide was designed and synthesized

<400> SEQUENCE: 2

Gly Gly Gly Ala Arg Lys Lys Ala Ala Lys Ala
1               5                   10

<210> SEQ ID NO 3
<211> LENGTH: 32
<212> TYPE: PRT
<213> ORGANISM: Artificial sequence
```

```
<220> FEATURE:
<223> OTHER INFORMATION: The peptide was designed and synthesized

<400> SEQUENCE: 3

Ala Arg Lys Lys Ala Ala Lys Ala Ala Arg Lys Lys Ala Ala Lys Ala
1               5                   10                  15

Ala Arg Lys Lys Ala Ala Lys Ala Ala Arg Lys Lys Ala Ala Lys Ala
            20                  25                  30

<210> SEQ ID NO 4
<211> LENGTH: 8
<212> TYPE: PRT
<213> ORGANISM: Artificial sequence
<220> FEATURE:
<223> OTHER INFORMATION: The peptide was designed and synthesized

<400> SEQUENCE: 4

Ala Arg Lys Lys Ala Ala Lys Ala
1               5

<210> SEQ ID NO 5
<211> LENGTH: 107
<212> TYPE: PRT
<213> ORGANISM: Artificial sequence
<220> FEATURE:
<223> OTHER INFORMATION: The peptide was designed and synthesized

<400> SEQUENCE: 5

Gly Cys Cys Ala Cys Cys Ala Thr Gly Gly Cys Thr Cys Gly Thr Ala
1               5                   10                  15

Ala Gly Ala Ala Gly Gly Cys Thr Cys Thr Ala Ala Gly Gly Cys
            20                  25                  30

Thr Gly Cys Cys Cys Gly Cys Ala Ala Gly Ala Ala Gly Gly Cys Thr
                35                  40                  45

Gly Cys Cys Ala Ala Gly Cys Cys Gly Cys Ala Cys Gly Ala Ala
    50                  55                  60

Ala Gly Ala Ala Gly Gly Cys Ala Gly Cys Ala Ala Ala Gly Gly Cys
65                  70                  75                  80

Gly Gly Cys Thr Cys Gly Thr Ala Ala Gly Ala Ala Gly Gly Cys Thr
                85                  90                  95

Gly Cys Cys Ala Ala Gly Gly Cys Gly Thr Cys
                100                 105

<210> SEQ ID NO 6
<211> LENGTH: 113
<212> TYPE: PRT
<213> ORGANISM: Artificial sequence
<220> FEATURE:
<223> OTHER INFORMATION: The peptide was designed and synthesized

<400> SEQUENCE: 6

Ala Ala Thr Thr Gly Ala Cys Gly Cys Thr Thr Gly Gly Cys Ala
1               5                   10                  15

Gly Cys Cys Thr Thr Cys Thr Thr Ala Cys Gly Ala Gly Cys Cys Gly
            20                  25                  30

Cys Cys Thr Thr Thr Gly Cys Thr Gly Cys Cys Thr Thr Cys Thr Thr
                35                  40                  45

Thr Cys Gly Thr Gly Cys Gly Gly Cys Cys Thr Thr Gly Gly Ala Ala
    50                  55                  60

Gly Cys Cys Thr Thr Cys Thr Thr Gly Cys Gly Gly Gly Cys Ala Gly
65                  70                  75                  80
```

Cys Cys Thr Thr Ala Gly Cys Ala Gly Cys Cys Thr Thr Cys Thr Thr
                85                  90                  95

Ala Cys Gly Ala Gly Cys Cys Ala Thr Gly Gly Thr Gly Gly Cys Gly
            100                 105                 110

Cys

<210> SEQ ID NO 7
<211> LENGTH: 25
<212> TYPE: PRT
<213> ORGANISM: Artificial sequence
<220> FEATURE:
<223> OTHER INFORMATION: The peptide was designed and synthesized

<400> SEQUENCE: 7

Cys Gly Ala Thr Cys Ala Thr Cys Ala Thr Cys Ala Cys Cys Ala Thr
1               5                   10                  15

Cys Ala Cys Cys Ala Thr Thr Gly Ala
            20                  25

<210> SEQ ID NO 8
<211> LENGTH: 27
<212> TYPE: PRT
<213> ORGANISM: Artificial sequence
<220> FEATURE:
<223> OTHER INFORMATION: The peptide was designed and synthesized

<400> SEQUENCE: 8

Cys Gly Cys Gly Thr Cys Ala Ala Thr Gly Gly Thr Gly Ala Thr Gly
1               5                   10                  15

Gly Thr Gly Ala Thr Gly Ala Thr Gly Ala Thr
            20                  25

<210> SEQ ID NO 9
<211> LENGTH: 87
<212> TYPE: DNA
<213> ORGANISM: Artificial sequence
<220> FEATURE:
<223> OTHER INFORMATION: The nucleotide was designed and synthesized

<400> SEQUENCE: 9
cgccaagctt gctcgtaaga aggctgctaa ggctgcccgc aagaaggccg ccaaggccgc    60
acgaaagaag gcagcgaagg cgtgagc                                       87

<210> SEQ ID NO 10
<211> LENGTH: 89
<212> TYPE: DNA
<213> ORGANISM: Artificial sequence
<220> FEATURE:
<223> OTHER INFORMATION: The nucleotide was designed and synthesized

<400> SEQUENCE: 10
ggccgctcac gccttcgctg ccttctttcg tgcggccttg gcggccttct tgcgggcagc    60
cttagcagcc ttcttacgag caagcttgg                                     89

<210> SEQ ID NO 11
<211> LENGTH: 36
<212> TYPE: PRT
<213> ORGANISM: Artificial Sequence
<220> FEATURE:
<223> OTHER INFORMATION: The peptide was designed and synthesized

<400> SEQUENCE: 11

Cys Gly Gly Gly Ala Arg Lys Lys Ala Ala Lys Ala Ala Arg Lys Lys
1               5                   10                  15

Ala Ala Lys Ala Ala Arg Lys Lys Ala Ala Lys Ala Ala Arg Lys Lys
                20                  25                  30

Ala Ala Lys Ala
        35

<210> SEQ ID NO 12
<211> LENGTH: 19
<212> TYPE: PRT
<213> ORGANISM: Artificial Sequence
<220> FEATURE:
<223> OTHER INFORMATION: This sequences was designed and synthesized.

<400> SEQUENCE: 12

Gly Gly Gly Ala Arg Lys Lys Ala Ala Lys Ala Ala Arg Lys Lys Ala
1               5                   10                  15

Ala Lys Ala

<210> SEQ ID NO 13
<211> LENGTH: 27
<212> TYPE: PRT
<213> ORGANISM: Artificial Sequence
<220> FEATURE:
<223> OTHER INFORMATION: This sequence was designed and synthesized.

<400> SEQUENCE: 13

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala
            20                  25

<210> SEQ ID NO 14
<211> LENGTH: 43
<212> TYPE: PRT
<213> ORGANISM: Artificial Sequence
<220> FEATURE:
<223> OTHER INFORMATION: This sequence was designed and synthesized.

<400> SEQUENCE: 14

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala Ala Arg Lys Lys Ala Ala Lys Ala
        35                  40

<210> SEQ ID NO 15
<211> LENGTH: 51
<212> TYPE: PRT
<213> ORGANISM: Artificial Sequence
<220> FEATURE:
<223> OTHER INFORMATION: This sequence was designed and synthesized.

<400> SEQUENCE: 15

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala Ala Arg Lys Lys Ala Ala Lys Ala Ala Arg Lys Lys Ala
        35                  40                  45

Ala Lys Ala

```
<210> SEQ ID NO 16
<211> LENGTH: 59
<212> TYPE: PRT
<213> ORGANISM: Artificial Sequence
<220> FEATURE:
<223> OTHER INFORMATION: This sequence was designed and synthesized.

<400> SEQUENCE: 16

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala Ala Arg Lys Lys Ala Ala Lys Ala Ala Arg Lys Lys Ala
        35                  40                  45

Ala Lys Ala Ala Arg Lys Lys Ala Ala Lys Ala
    50                  55

<210> SEQ ID NO 17
<211> LENGTH: 67
<212> TYPE: PRT
<213> ORGANISM: Artificial Sequence
<220> FEATURE:
<223> OTHER INFORMATION: This sequence was designed and synthesized.

<400> SEQUENCE: 17

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala Ala Arg Lys Lys Ala Ala Lys Ala Ala Arg Lys Lys Ala
        35                  40                  45

Ala Lys Ala Ala Arg Lys Lys Ala Ala Lys Ala Ala Arg Lys Lys Ala
    50                  55                  60

Ala Lys Ala
65
```